US007718625B2

(12) United States Patent
Eichler et al.

(10) Patent No.: US 7,718,625 B2
(45) Date of Patent: May 18, 2010

(54) POLYNUCLEOTIDES TARGETED AGAINST THE EXTENDED 5'-UTR REGION OF ARGININOSUCCINATE SYNTHASE AND USES THEREOF

(75) Inventors: Duane C. Eichler, Wesley Chapel, FL (US); Larry P. Solomonson, Lutz, FL (US); Laura C. Pendleton, Valrico, FL (US)

(73) Assignee: University of South Florida, Tampa, FL (US)

( * ) Notice: Subject to any disclaimer, the term of this patent is extended or adjusted under 35 U.S.C. 154(b) by 51 days.

(21) Appl. No.: 11/341,177

(22) Filed: Jan. 27, 2006

(65) Prior Publication Data

US 2006/0166922 A1 Jul. 27, 2006

Related U.S. Application Data

(60) Provisional application No. 60/647,750, filed on Jan. 27, 2005.

(51) Int. Cl.
*A01N 43/04* (2006.01)
*A61K 31/70* (2006.01)
*C07H 21/04* (2006.01)

(52) U.S. Cl. .................................. 514/44; 536/24.5
(58) Field of Classification Search ................ 536/24.5; 514/44
See application file for complete search history.

(56) References Cited

U.S. PATENT DOCUMENTS

| 4,987,071 | A | 1/1991 | Cech et al. |
| 5,093,246 | A | 3/1992 | Cech et al. |
| 5,116,742 | A | 5/1992 | Cech et al. |
| 6,506,559 | B1 | 1/2003 | Fire et al. |
| 2004/0137471 | A1* | 7/2004 | Vickers et al. ............... 435/6 |
| 2004/0192626 | A1* | 9/2004 | McSwiggen et al. ......... 514/44 |
| 2006/0068405 | A1* | 3/2006 | Diber et al. .................. 435/6 |

FOREIGN PATENT DOCUMENTS

| WO | WO 99/32619 A1 | 7/1999 |
| WO | WO 01/75164 A2 | 10/2001 |

OTHER PUBLICATIONS

Paddison et al. Methods Mol Biol. 2004; 265:85-100).*
Brasse-Lagnel et al. The Journal of Biological Chemistry 278:52504-52510, 2003.*
Hammond et al. (Nature, 2001, vol. 2, pp. 110-119).*
Ambion (http://www.ambion.com/techlib/misc/siRNA_finder.html, retrieved on Dec. 18, 2007), siRNA Converter and RNA Oligo Calculator, $2^{nd}$ result with GenBank NM_054012.*
Brasse-Lagnel et al. (The Journal of Biological Chemistry 278:52504-52510, 2003).*
Ambion (Oct. 2002) TechNotes 9(5) Selecting siRNA Sequences to Incorporate into the pSilencer Vectors. [online], [retrieved on Nov. 5, 2008] using Internet <URL:http://www.ambion.com>.*
Bagheri, S. et al. "Ribozymes in the Age of Molecular Therapeutics", *Curr. Mol. Med.*, Aug. 2004, 4(5):489-506.
Bartel, D. and Szostak, J.W. "Isolation of New Ribozymes from a Large Pool of Random Sequences", *Science* 261:1411-1418 (1993).
Beaudet, A.L. et al. "The Human Argininosuccinate Synthetase Locus and Citrullinemia", *Adv. Hum. Genet.*, 15:161-196, (1986).
Bonetta, L. "RNAi: Silencing Never Sounded Better", *Nature Methods*, Oct. 2004, 1(1):79-86.
Bredt, D.S. and Snyder, S.H. "Nitric Oxide: A Physiologic Messenger Molecule", *Annu. Rev. Biochem.*, 1994, 63:175-195.
Brusilow, S.W. and Horwich, A.L., The Molecular and Metabolic Basis of Inherited Disease, eds., Scriver, C.R., Beaudet, A.L., Sly, W.S., & Valle, D. (McGraw-Hill, New York), pp. 1187-1232, 1995.
Cohen, N.S. and Kuda, A. "Argininosuccinate Synthetase and Argininosuccinate Lyase are Localized Around Mitochondria: An Immunocytochemical Study", *J. Cell. Biochem.*, 1996, 60:334-340.
Dennis, J.A. et al. "Molecular Definition of Bovine Argioniosuccinate Synthetase Deficiency", *Proc Natl Acad Sci USA*, 1989, 86:7947-7951.
Elbashir, S.M. et al. "Duplexes of 21-Nucleotide RNAs Mediate RNA Interference in Cultured Mammalian Cells", *Nature* 411:494-98 (2001).
Fire, A. et al. "Potent and Specific Genetic Interference by Double-Stranded RNA in *Caenorhabditis elegans*", *Nature* 391:806-11 (1998).
Flam, B.R. et al. "Caveolar Localization of Arginine Regeneration Enzymes, Argininosuccinate Synthase, and Lyase, with Endothelial Nitric Oxide Synthase", *Nitric Oxide*, 2001, 5:187-197.
Freytag, S.O. et al. "Molecular Structures of Human Argininosuccinate Synthetase Pseudogenes", *J. Biol. Chem.*, 1984, 259:3160-3166.
Gaba, A. et al. "Physical Evidence for Distinct Mechanisms of Translational Control by Upstream Open Reading Frames", *Embo. J.*, 2001, 20:6453-6463.
GenBank Accession No. BC063146, Jan. 6, 2006.
GenBank Accession No. NM_007494, Dec. 11, 2005.
GenBank Accession No. NM_054012, Oct. 18, 2005.
Goligorsky, M.S. and Gross, S.S. "The Ins and Outs of Endothelial Dysfunction: Much Ado about NO-Thing", *Drug News Perspect.*, 2001, 14:133-142.
Goodwin, B.L. et al. "Argininosuccinate Synthase Expression is Required to Maintain Nitric Oxide Production and Cell Viability in Aortic Endothelial Cells", *J. Biol. Chem.*, 2004, 279:18353-18360.

(Continued)

*Primary Examiner*—Brian Whiteman
(74) *Attorney, Agent, or Firm*—Saliwanchik, Lloyd & Saliwanchik

(57) ABSTRACT

The present invention is based in part on the discovery that the upstream open reading frame (uORF) in the extended 5'-untranslated region (5'-UTR) argininosuccinate synthase (AS) mRNA species is functional, and when functional, limits overall AS expression as well as nitric oxide (NO) production. Thus, the extended 5'-UTR AS mRNA species is a mechanism for regulating AS expression and NO production, and provides a target for the treatment of pathophysiological conditions associated with vascular endothelial dysfunction and characterized by impairment of NO production, such as heart failure, hypertension, hypercholesterolemia, atherosclerosis, and diabetes.

23 Claims, 22 Drawing Sheets

OTHER PUBLICATIONS

Gow, A.J. and Ischiropoulos, H. "Nitric Oxide Chemistry and Cellular Signaling", *J. Cell. Physiol.*, 2001, 187:277-282.

Grassi, G. et al. "Therapeutic Potential of Hammerhead Ribozymes in the Treatment of Hyper-Proliferative Diseases", *Curr. Pharm. Biotechnol.*, Aug. 2004, 5(4):369-386.

Harborth, J. et al. "Identification of Essential Genes in Cultured Mammalian Cells Using Small Interfering RNAs", *J. Cell Sci.*, 2001, 114:4557-65.

Haseloff, J. and Gerlach, W. "Simple RNA Enzymes with New and Highly Specific Endoribonuclease Activities", *Nature*, 1988, 334:585-591.

Helene, C. et al. "Control of Gene Expression by Triple Helix-Forming Oligonucleotides", *Ann. N.Y. Acad. Sci.*, 1992, 660:27-36.

Helene, C. "The Anti-Gene Strategy: Control of Gene Expression by Triplex-Forming-Oligonucleotides", *Anticancer Drug Des.*, 1991, 6:569-84.

Hellermann, G.R. et al. "Stimulation of Receptor-Mediated Nitric Oxide Production by Vanadate", *Arterioscler Thromb Vasc Biol*, 2000, 20:2045-2050.

Hendry, P. et al., Redesigned and Chemically-Modified Hammerhead Ribozymes with Improved Activity and Serum Stability, *BMC Chem. Biol.*, Dec. 2004, 4(1):1.

Jinno, Y. et al. "Novel Structure of the 5' End Region of the Human Argininosuccinate Sythetase Gene", *J. Biochem.*, 1985, 98:1395-1403.

Kashani-Sabet, M. "Non-Viral Delivery of Ribozymes for Cancer Gene Therapy", *Expert Opin. Biol. Ther.*, Nov. 2004, 4(11):1749-1755.

Kozak, M. "Initiation of Translation in Prokaryotes and Eukaryotes", *Gene*, 1999, 234:187-208.

Kozak, M. "Structural Features in Eukaryotic mRNAs That Modulate the Initiation of Translation", *J. Biol. Chem.*, 1991, 266:19867-19870.

Lee, B. et al. "Hepatocyte Gene Therapy in a Large Animal: A Neonatal Bovine Model of Citrullinemia", *Proc. Natl. Acad. Sci. USA*, 1999, 96:3981-3986.

Maher, L.J. "DNA Triple-Helix Formation: An Approach to Artificial Gene Repressors?" *Bioassays*, 1992, 14:807-15.

Maxwell, A.J. "Mechanisms of Dysfunction of the Nitric Oxide Pathway in Vascular Diseases", *Nitric Oxide*, 2002, 6:101-124.

Morris, D.R. and Geballe, A.P. "Upstream Open Reading Frames as Regulators of mRNA Translation", *Mol. Cell. Biol.*, 2000, 20:8635-8642.

Morris, S.M., Jr. "Regulation of Enzymes of Urea and Arginine Synthesis", *Annu. Rev. Nutr.*, 1992, 12:81-101.

Newton, D.C. et al. "Translational Regulation of Human Neuronal Nitric-Oxide Synthase by an Alternatively Spliced 5'-Untranslated Region Leader Exon", *J. Biol. Chem.*, 2003, 278:636-644.

Parola, A.L. and Kobilka, B.K. "The Peptide Product of a 5' Leader Cistron in the $\beta_2$ Adrenergic Receptor mRNA Inhibits Receptor Synthesis", *J. Biol. Chem.*, 1994, 269:4497-4505.

Pendleton, L.C. et al. "Novel regulation of endothelial argininosuccinate synthase and nitric oxide synthase by an As uORF" presented at the IUBMB/ASBMB Meeting, Jun. 12-16, 2004 in Boston, MA.

Pendleton, L.C. et al. "Endothelial Argininosuccinate Synthase mRNA 5'-Untranslated Region Diversity", *J. Biol. Chem.*, 2002, 277:25363-25369.

Pendleton, L.C. et al. "Regulation of Endothelial Argininosuccinate Synthase Expression and NO Production by an Upstream Open Reading Frame", *J. Biol. Chem.*, 2005, 280(25):24252-24260.

Saur, D. et al. "Complex Regulation of Human Neuronal Nitric-Oxide Synthase Exon 1c Gene Transcription", *J. Biol. Chem.*, 2002, 277:25798-25814.

Sharma, R. and Davidoff, M.N. "Oxidative Stress and Endothelial Dysfunction in Heart Failure", *Congest. Heart Fail.*, 2002, 8:165-172.

Sharp, P.A. "RNAi and Double-Strand RNA", *Genes Dev.*, 1999, 13:139-41.

Sofowora, G. et al. "In-Vivo Effects of Glu298Asp Endothelial Nitric Oxide Synthase Polymorphism", *Pharmacogenetics*, 2001, 11:809-814.

Solomonson, L. et al. "The Caveolar Nitric Oxide Synthase/Arginine Regeneration System for NO Production in Endothelial Cells", *J. Exp. Biol.*, 2003, 206:2083-2087.

Soutschek, J. et al. "Therapeutic Silencing of an Endogenous Gene by Systemic Administration of Modified siRNAs", *Nature*, 2004, 432:173-178.

Su, T-S. et al. "Molecular Analysis of Argininosuccinate Synthetase Deficiency in Human Fibroblasts", *J. Clin. Invest.*, 1982, 70:1334-1339.

Surh, L.C. et al. "Molecular Characterization of the Murine Argininosuccinate Synthetase Locus", *Gene*, 1991, 99:181-189.

Vallance, P. and Chan, N. "General Cardiology: Endothelial Function and Nitric Oxide: Clinical Relevance", *Heart*, 2001, 85:342-50.

Wang, Y. et al. "RNA Diversity Has Profound Effects on the Translation of Neuronal Nitric Oxide Synthase", *PNAS*, 1999, 96:12150-12155.

Xie, L. and Gross, S.S. "Argininosuccinate Synthetase Overexpression in Vascular Smooth Muscle Cells Potentiates Immunostimulant-Induced NO Production", *J. Biol. Chem.*, 1997, 272:16624-16630.

Elbashir, S.M. et al. "Analysis of gene function in somatic mammalian cells using small interfering RNAs" *Methods*, 2002, pp. 199-213, vol. 26.

Mittal, V. "Improving the Efficiency of RNA Interference in Mammals" *Nature Reviews/Genetics*, pp. 355-365, May 2004, vol. 5.

Protocols & Applications Guide, 2RNA Interference, Aug. 2005, cover page and pp. 2-1-2-18.

Applied Biosystems, Technical Bulletin #506, siRNA Design Guidelines, pp. 1-8, accessed Sep. 9, 2008.

\* cited by examiner

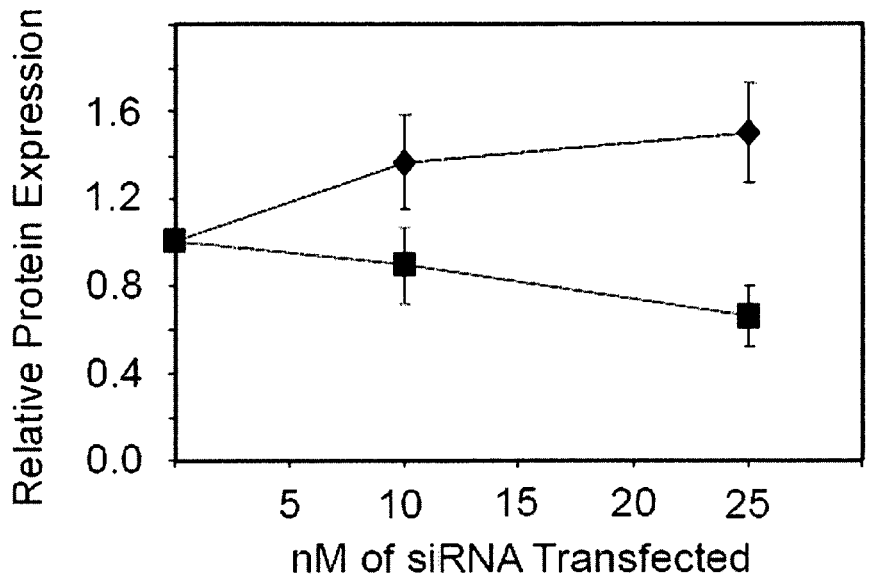

FIG. 9C

|  | ↓ 92 nt 5'-UTR | | ↓ 66 nt 5'-UTR |
|---|---|---|---|

Bovine  ~~~~CCCTGC CCCCCGGCCC CGA|GCTTATA ACC|CG|GGATG
Human   CCGGCCCTGC CCCCGGGCCC TGT|GCTTATA ACC|TG|GGATG
Mouse   TTCCTGCCCC CCCCAGGCCC TGT|GCTTATA ACC|CT|GGATG ↓ 43 nt 5'-UTR Bovine  CGCGCCGAAA CCCGCCCTGC TCCGCCGACT GCTGCCGCCG
Human   GGCACCCCTG CCAGT<u>CCTGC TCTGCCGCCT GCCACCGCTG</u>
Mouse   CGCGCCTCTC TC<u>AGCCCTCT GCCGCCGTCT GCCACTGCGC</u>

↓ START

Bovine  CTGGTCAC.C CGTCACGATG TCCGGCAAA
Human   <u>CCCG.AGC.C C</u>GACGCTATG TCCAGCAAA
Mouse   <u>CTGGGCTCAC TG</u>ACAAGATG TCCAGCGGC

FIG. 10

DNA sequence of target site
RNA target
Hairpin siRNA
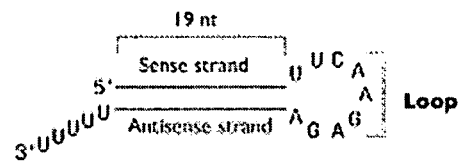
FIG. 11
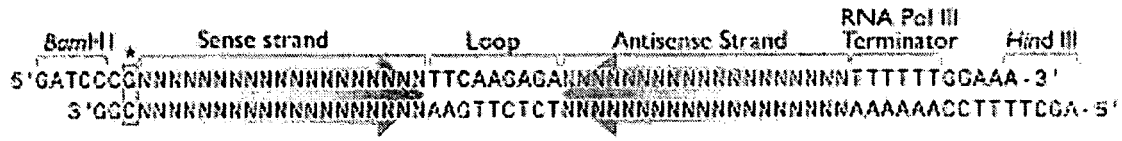
FIG. 12

```
  1  cccgccacgt gtccccggtc accggccctg cccccgggcc ctgtgcttat aacctgggat
 61  gggcacccct gccagtcctg ctctgccgcc tgccaccgct gcccgagccc gacgctatgt
```

↑ Position -66 relative to AS AUG

↑ Position -43 relative to AS AUG

↑ AS AUG

FIG. 14

```
   1 cccgccacgt gtccccggtc accggccctg ccccgggcc ctgtgcttat aacctgggat
  61 gggcacccct gccagtcctg ctctgccgcc tgccaccgct gcccgagccc gacgctatgt
 121 ccagcaaagg ctccgtggtt ctggcctaca gtggcggcct ggacacctcg tgcatcctcg
 181 tgtggctgaa ggaacaaggc tatgacgtca ttgcctatct ggccaacatt ggccagaagg
 241 aagacttcga ggaagccagg aagaaggcac tgaagcttgg ggccaaaaag gtgttcattg
 301 aggatgtcag cagggagttt gtggaggagt tcatctggcc ggccatccag tccagcgcac
 361 tgtatgagga ccgctacctc ctgggcacct ctcttgccag gccctgcatc gcccgcaaac
 421 aagtggaaat cgcccagcgg gaggggcca agtatgtgtc ccacggcgcc acaggaaagg
 481 ggaacgatca ggtccggttt gagctcagct gctactcact ggccccccag ataaaggtca
 541 ttgctccctg gaggatgcct gaattctaca accggttcaa gggccgcaat gacctgatgg
 601 agtacgcaaa gcaacacggg attcccatcc cggtcactcc caagaacccg tggagcatgg
 661 atgagaacct catgcacatc agctacgagg ctggaatcct ggagaacccc aagaaccaag
 721 cgcctccagg tctctacacg aagacccagg acccagccaa agcccccaac acccctgaca
 781 ttctcgagat cgagttcaaa aaggggtcc ctgtgaaggt gaccaacgtc aaggatggca
 841 ccacccacca gacctccttg gagctcttca tgtacctgaa cgaagtcgcg ggcaagcatg
 901 gcgtgggccg tattgacatc gtggagaacc gcttcattgg aatgaagtcc gaggtatct
 961 acgagacccc agcaggcacc atcctttacc atgctcattt agacatcgag gccttcacca
1021 tggaccggga agtgcgcaaa atcaaacaag gcctgggctt gaaatttgct gagctggtgt
1081 ataccggttt ctggcacagc cctgagtgtg aatttgtccg ccactgcatc gccaagtccc
1141 aggagcgagt ggaagggaaa gtgcaggtgt ccgtcctcaa gggccaggtg tacatcctcg
1201 gccgggagtc cccactgtct ctctacaatg aggagctggt gagcatgaac gtgcagggtg
1261 attatgagcc aactgatgcc accgggttca tcaacatcaa ttccctcagg ctgaaggaat
1321 atcatcgtct ccagagcaag gtcactgcca aatagacccg tgtacaatga ggagctgggg
1381 cctcctcaat ttgcagatcc cccaagtaca ggcgctaatt gttgtgataa tttgtaattg
1441 tgacttgttc tccccggctg gcagcgtagt ggggctgcca ggccccagct ttgttccctg
1501 gtccccctga agcctgcaaa cgttgtcatc gaagggaagg gtgggggca gctgcggtgg
1561 ggagctataa aaatgacaat taaagagac actagtcttt tatttctaaa aaaaaaaaa
1621 aaaaaaaaa a
```

FIG. 17

```
   1 gcttataacc ctggatgcgc gcctctctca gccctgctcc gccgtctgcc actgccgcct
  61 gggctcactg agtggttcat ctggccagga aagcagacta cacggactcc agggacctgt
 121 acctataatc caagacaaga tgtccagcaa gggctctgtg gttctggcct acagtggtgg
 181 cctggacacc tcctgcatcc tcgtgtggct gaaggaacaa ggctatgatg tcatcgccta
 241 cctggccaac attggccaga aggaagactt tgaggaagcc aggaagaagg cgctgaagct
 301 tggggccaaa aaggtgttca ttgaggatgt gagcaaggaa tttgtggaag agttcatctg
 361 gcctgctgtc cagtccagtg cactctacga ggaccgctat ctcctgggca cctctctcgc
 421 caggccttgc atagctcgca gacaggtgga gattgcccag cgtgaagggg ccaagtatgt
 481 gtctcacggc gccacgggaa aggggaatga ccaggtccgc tttgagctca cctgctactc
 541 actggcaccc cagattaagg tcatcgctcc ctggaggatg cctgagtttt acaaccggtt
 601 caagggccga aatgatctga tggagtatgc aaagcaacac ggaatcccca tccctgtcac
 661 ccccaagagc ccctggagta tggatgaaaa cctcatgcac atcagctatg aggctgggat
 721 cctggaaaac cccaagaatc aagcacctcc gggtctctac acaaaaactc aggaccctgc
 781 caaagcaccc aacagcccag atgtccttga gatagaattc aaaaaagggg tccctgtgaa
 841 ggtgaccaac atcaaagatg gcacaacccg caccacatcc ctggaactct tcatgtacct
 901 gaacgaagtt gcgggcaagc acggagtggg tcgcattgac atcgtggaga accgcttcat
 961 tggaatgaag tcccgaggta tctacgagac cccagcaggg accatccttt accacgctca
1021 tttagacata gaggccttca cgatggatcg ggaagtacgc aaaatcaagc agggcctggg
1081 cctcaaattc gcagagctcg tatacacagg tttctggcac agccctgaat gtgaatttgt
1141 tcgccactgt atccagaagt cccaggagcg ggtagaaggg aaggtgcagg tgtctgtctt
1201 caagggccaa gtgtacatcc tcggtcggga gtctccactt tcactctaca atgaagagct
1261 ggtgagcatg aacgtacagg gcgactatga gccatcgac gccactggct tcatcaatat
1321 caactcgctc aggctgaagg agtaccatcg ccttcagagc aaggtcactg ccaaatagac
1381 cctgacaaag aggagcgggc ctccccactc tgcagctctc ccaggcttca gcattaattg
1441 ttgtgataaa tttgtaattg tagcttgttc tccaccacct gactggggct gctgtgtccc
1501 ccccgccccc ccacagcctt tgttccctgg tccctatag cctacaaaag tggtcatcga
1561 agggaaggga gggtggcggg cagctgcaga agcataaaa tgacaattaa aagaagttac
1621 attagtcttt aaaaaaaaaa aaaaa
```

FIG. 18

```
   1 ggggccccca ggccctgtgc ttataaccct ggatgcgcgc ctctcccggt cctgctccgc
  61 tgttcgccac tgccgcctgg gctcactgag tggttcaccc ggccaggaag acagactacg
 121 gactccaggg acctgtagct acaatccaag acaagatgtc cagcaagggc tctgtggttc
 181 tggcctacag tggtggtctg gacacctcct gcatcctcgt gtggctgaag gaacaaggct
 241 atgatgtcat cgcctacctg gccaacattg gccagaagga agactttgag gaagccagga
 301 agaaggcact gaagcttggg gccaaaaagg tgttcattga ggatgtaagc aaggagtttg
 361 tggaagagtt catctggcct gctgtccagt ccagtgcact ctatgaggac cgctatctcc
 421 taggcacctc tctcgccagg ccttgcatag ctcgcaaaca agtggaaatt gcccagcgcg
 481 aaggggccaa gtatgtgtct cacggcgcca cggggaaggg caatgaccag gtccgctttg
 541 agctcacctg ctactcgtta gcaccccaga ttaaggtcat cgcccctgg aggatgcccg
 601 agttttacaa ccggttcaag ggccgaaatg atttgatgga atacgcaaag caacatggaa
 661 tccccatccc tgtcaccccc aagagcccct ggagcatgga tgagaacctt atgcacatca
 721 gctacgaggc tggaatcctg gaaaacccca agaaccaagc acctccaggt ctctacacaa
 781 aaactcagga ccctgccaaa gcacccaaca cccagatgt ccttgagata gaattcaaaa
 841 aaggggtccc tgtgaaggtg accaacgtca agatggcac tacccacagc acatccttgg
 901 acctcttcat gtacctgaat gaagttgcgg gcaagcatgg agtagggcgc attgacatcg
 961 tggagaaccg cttcattgga atgaagtccc ggggtatcta cgagacccca gcagggacca
1021 tcctttacca cgctcattta gacatagagg ccttcaccat ggatcgggaa gtacgcaaaa
1081 tcaagcaggg cctgggcctc aaattcgcag agctcgtata caccggtttc tggcacagcc
1141 ctgaatgtga atttgttcgc cactgcatcg acaagtccca ggaacgggtg gaaggaaagg
1201 tgcaggtatc tgtcttcaag ggccaggtgt acatccttgg ccgggagtct ccactttcac
1261 tatacaatga agagctggtg agcatgaacg tacagggtga ctatgaaccc attgatgcca
1321 ccggcttcat caatatcaac tcgctcaggc tgaaggagta ccatcgcctt cagagcaagg
1381 tcaccgccaa ataccgtg acaaagagc gcgggcctcc ccgctctgca gctctcccag
1441 gctccagcat taattgttgt gataaatttg taattgtagc ttgttctcct accacctgac
1501 tggggctgct gtgccccccc tcacctcccc cccacccaca ggctttgttc cctggtcccc
1561 tatagcctac aaaagtggtc atcgaaggga aggggggtg gcaggcagct gcagaaagcg
1621 cgtaaaatga caattaaaag aagttacatt agtaaaaaaa ataaaaaaaa aaaaaaaaaa
1681 aaaaaaaaaa aaaa
```

FIG. 19

SEQUENCE LISTING

```
<160> NUMBER OF SEQ ID NOS: 35

<210> SEQ ID NO 1
<211> LENGTH: 21
<212> TYPE: RNA
<213> ORGANISM: Artificial Sequence
<220> FEATURE:
<223> OTHER INFORMATION: interfering RNA sequence targeting bovine
      extended 5'-UTR AS mRNA

<400> SEQUENCE: 1
cccgggaugc gcgccgaaau u                                              21

<210> SEQ ID NO 2
<211> LENGTH: 23
<212> TYPE: DNA
<213> ORGANISM: Artificial Sequence
<220> FEATURE:
<223> OTHER INFORMATION: left primer ASL-11MFS

<400> SEQUENCE: 2
cacccgtcac gaatgtccgg caa                                            23

<210> SEQ ID NO 3
<211> LENGTH: 23
<212> TYPE: DNA
<213> ORGANISM: Artificial Sequence
<220> FEATURE:
<223> OTHER INFORMATION: left primer ASL-48MFS

<400> SEQUENCE: 3
aacccgccct agctccgccg act                                            23

<210> SEQ ID NO 4
<211> LENGTH: 20
<212> TYPE: DNA
<213> ORGANISM: Artificial Sequence
```

```
<220> FEATURE:
<223> OTHER INFORMATION: right primer ASR429

<400> SEQUENCE: 4
gagcgatgac cttgatctgt                                              20

<210> SEQ ID NO 5
<211> LENGTH: 27
<212> TYPE: DNA
<213> ORGANISM: Artificial Sequence
<220> FEATURE:
<223> OTHER INFORMATION: left primer ASL59MStop

<400> SEQUENCE: 5
tcctcgtgtg gcaaaaggag caaggct                                      27

<210> SEQ ID NO 6
<211> LENGTH: 26
<212> TYPE: DNA
<213> ORGANISM: Artificial Sequence
<220> FEATURE:
<223> OTHER INFORMATION: right primer ASR168MStop

<400> SEQUENCE: 6
ggccccaagc ttttgcgcct tcttcc                                       26

<210> SEQ ID NO 7
<211> LENGTH: 36
<212> TYPE: DNA
<213> ORGANISM: Artificial Sequence
<220> FEATURE:
<223> OTHER INFORMATION: left primer LucASL-66

<400> SEQUENCE: 7
agaaagctta cccgggatgg aagacgccaa aaacat                            36

<210> SEQ ID NO 8
<211> LENGTH: 63
<212> TYPE: DNA
<213> ORGANISM: Artificial Sequence
<220> FEATURE:
<223> OTHER INFORMATION: left primer LucASL-92

<400> SEQUENCE: 8
agaaagcttc cctgcccccc ggccccgagc ttataacccg ggatggaaga cgccaaaaac   60
ata                                                                63

<210> SEQ ID NO 9
<211> LENGTH: 20
<212> TYPE: DNA
<213> ORGANISM: Artificial Sequence
<220> FEATURE:
<223> OTHER INFORMATION: right primer RTLuc1R

<400> SEQUENCE: 9
cacctcgata tgtgcatctg                                              20

<210> SEQ ID NO 10
<211> LENGTH: 30
<212> TYPE: DNA
<213> ORGANISM: Artificial Sequence
<220> FEATURE:
<223> OTHER INFORMATION: left primer ASL-92BamHI
```

```
<400> SEQUENCE: 10
agtcggatcc ccctgccccc cggccccgag                              30

<210> SEQ ID NO 11
<211> LENGTH: 30
<212> TYPE: DNA
<213> ORGANISM: Artificial Sequence
<220> FEATURE:
<223> OTHER INFORMATION: left primer ASL-43BamHI

<400> SEQUENCE: 11
agtcggatcc gccctgctcc gccgactgct                              30

<210> SEQ ID NO 12
<211> LENGTH: 33
<212> TYPE: DNA
<213> ORGANISM: Artificial Sequence
<220> FEATURE:
<223> OTHER INFORMATION: right primer ASR73EcoRI

<400> SEQUENCE: 12
tgcagaattc ccgccacacg aggatgcagg agg                          33

<210> SEQ ID NO 13
<211> LENGTH: 24
<212> TYPE: DNA
<213> ORGANISM: Artificial Sequence
<220> FEATURE:
<223> OTHER INFORMATION: primer uORFfsleft

<400> SEQUENCE: 13
accccgggat gcgcccgaaa cccg                                    24

<210> SEQ ID NO 14
<211> LENGTH: 24
<212> TYPE: DNA
<213> ORGANISM: Artificial Sequence
<220> FEATURE:
<223> OTHER INFORMATION: primer uORFfsright

<400> SEQUENCE: 14
cagaattccc gcccacacga ggat                                    24

<210> SEQ ID NO 15
<211> LENGTH: 34
<212> TYPE: DNA
<213> ORGANISM: Artificial Sequence
<220> FEATURE:
<223> OTHER INFORMATION: primer uORFdnsAUG

<400> SEQUENCE: 15
gctggtcacc cgtcacgaat gccggcaaag gctc                         34

<210> SEQ ID NO 16
<211> LENGTH: 39
<212> TYPE: DNA
<213> ORGANISM: Artificial Sequence
<220> FEATURE:
<223> OTHER INFORMATION: primer uORFupsStop

<400> SEQUENCE: 16
gctggtcacc cgtcacgatg tccggcatag gctccgtgg                    39
```

<210> SEQ ID NO 17
<211> LENGTH: 31
<212> TYPE: DNA
<213> ORGANISM: Artificial Sequence
<220> FEATURE:
<223> OTHER INFORMATION: primer GFPleft

<400> SEQUENCE: 17
agtcggcggc cgccgccaca tgagcaaggg c                            31

<210> SEQ ID NO 18
<211> LENGTH: 24
<212> TYPE: DNA
<213> ORGANISM: Artificial Sequence
<220> FEATURE:
<223> OTHER INFORMATION: primer GFPright

<400> SEQUENCE: 18
ctagagcggc cgcacttgta cagc                                    24

<210> SEQ ID NO 19
<211> LENGTH: 21
<212> TYPE: RNA
<213> ORGANISM: Artificial Sequence
<220> FEATURE:
<223> OTHER INFORMATION: scrambled control for AS siRNA sequence

<400> SEQUENCE: 19
acagagggac ucgcccgcgu u                                       21

<210> SEQ ID NO 20
<211> LENGTH: 20
<212> TYPE: DNA
<213> ORGANISM: Artificial Sequence
<220> FEATURE:
<223> OTHER INFORMATION: primer beta-actin forward

<400> SEQUENCE: 20
gaggcatcct gaccctcaag                                         20

<210> SEQ ID NO 21
<211> LENGTH: 20
<212> TYPE: DNA
<213> ORGANISM: Artificial Sequence
<220> FEATURE:
<223> OTHER INFORMATION: primer beta-actin reverse

<400> SEQUENCE: 21
tccatgtcgt cccagttggt                                         20

<210> SEQ ID NO 22
<211> LENGTH: 21
<212> TYPE: RNA
<213> ORGANISM: Artificial Sequence
<220> FEATURE:
<223> OTHER INFORMATION: siRNA targeting human extended 5'-UTR AS mRNA

<400> SEQUENCE: 22
aacccgggau gcgcgccgaa a                                       21

<210> SEQ ID NO 23
<211> LENGTH: 64
<212> TYPE: DNA
<213> ORGANISM: Artificial Sequence
<220> FEATURE:
<223> OTHER INFORMATION: sense strand of a siRNA targeting human
      extended 5'-UTR AS mRNA

<400> SEQUENCE: 23 gatccgccc ggatgcgcgc cgaaattcaa gagatttcgg cgcgcatccc gggttttttg    60
gaaa                                                                 64

<210> SEQ ID NO 24
<211> LENGTH: 64
<212> TYPE: DNA
<213> ORGANISM: Artificial Sequence
<220> FEATURE:
<223> OTHER INFORMATION: anti-sense strand of a siRNA targeting human
      extended 5'-UTR AS mRNA

<400> SEQUENCE: 24
agcttttcca aaaaacccgg gatgcgcgcc gaaatctctt gaatttcggc gcgcatcccg    60
ggcg                                                                 64

<210> SEQ ID NO 25
<211> LENGTH: 21
<212> TYPE: DNA
<213> ORGANISM: Homo sapiens
<220> FEATURE:
<221> NAME/KEY: misc_feature
<222> LOCATION: (1)..(21)
<223> OTHER INFORMATION: target sequence within human extended 5'-UTR AS

<400> SEQUENCE: 25
aacctgggat gggcacccct g                                              21

<210> SEQ ID NO 26
<211> LENGTH: 212
<212> TYPE: RNA
<213> ORGANISM: Bos taurus
<220> FEATURE:
<221> NAME/KEY: misc_feature
<222> LOCATION: (1)..(212)
<223> OTHER INFORMATION: 5' leader sequence of endothelial AS mRNA,
      including target site for interfering RNA

<400> SEQUENCE: 26
cccugccccc cggccccgag cuuauaaccc gggaugcgcg ccgaaacccg cccugcuccg    60
ccgacugcug ccgccgcugg ucacccguca cgaugccgg caaaggcucc gugguucugg   120
ccuacagugg gggccuggac accuccugca uccucgugug gcugaaggag caaggcuaug   180
acgucauugc cuaccuggcc aacaucggcc ag                                 212

<210> SEQ ID NO 27
<211> LENGTH: 104
<212> TYPE: DNA
<213> ORGANISM: Bos taurus

<400> SEQUENCE: 27
ccctgccccc cggccccgag cttataaccc gggatgcgcg ccgaaacccg ccctgctccg    60
ccgactgctg ccgccgctgg tcacccgtca cgatgtccgg caaa                   104

<210> SEQ ID NO 28
<211> LENGTH: 107
<212> TYPE: DNA
<213> ORGANISM: Homo sapiens

<400> SEQUENCE: 28
ccggccctgc cccgggccc tgtgcttata acctgggatg ggcacccctg ccagtcctgc    60
tctgccgcct gccaccgctg cccgagcccg acgctatgtc cagcaaa                107

```
<210> SEQ ID NO 29
<211> LENGTH: 109
<212> TYPE: DNA
<213> ORGANISM: Mus musculus

<400> SEQUENCE: 29
ttcctgcccc cccaggcccc tgtgcttata accctggatg cgcgcctctc tcagccctct    60
gccgccgtct gccactgcgc ctgggctcac tgacaagatg tccagcggc               109

<210> SEQ ID NO 30
<211> LENGTH: 65
<212> TYPE: DNA
<213> ORGANISM: Artificial Sequence
<220> FEATURE:
<223> OTHER INFORMATION: bottom portion of the pSILENCER 2.1-U6neo
      vector map
<220> FEATURE:
<221> NAME/KEY: misc_feature
<222> LOCATION: (4)..(22)
<223> OTHER INFORMATION: n is a, c, g, or t
<220> FEATURE:
<221> NAME/KEY: misc_feature
<222> LOCATION: (32)..(50)
<223> OTHER INFORMATION: n is a, c, g, or t

<400> SEQUENCE: 30
ggcnnnnnnn nnnnnnnnnn nnaagttctc tnnnnnnnnn nnnnnnnnnn aaaaaaccctt   60 ttcga                                                                65

<210> SEQ ID NO 31
<211> LENGTH: 65
<212> TYPE: DNA
<213> ORGANISM: Artificial Sequence
<220> FEATURE:
<223> OTHER INFORMATION: top portion of the pSILENCER 2.1-U6neo vector
      map
<220> FEATURE:
<221> NAME/KEY: misc_feature
<222> LOCATION: (8)..(26)
<223> OTHER INFORMATION: n is a, c, g, or t
<220> FEATURE:
<221> NAME/KEY: misc_feature
<222> LOCATION: (36)..(54)
<223> OTHER INFORMATION: n is a, c, g, or t

<400> SEQUENCE: 31
gatcccgnnn nnnnnnnnnn nnnnnnttca agagannnnn nnnnnnnnnn nnnntttttt    60
ggaaa                                                                65

<210> SEQ ID NO 32
<211> LENGTH: 120
<212> TYPE: DNA
<213> ORGANISM: Homo sapiens

<400> SEQUENCE: 32
cccgccacgt gtccccggtc accggccctg ccccgggcc ctgtgcttat aacctgggat     60
gggcacccct gccagtcctg ctctgccgcc tgccaccgct gcccgagccc gacgctatgt   120

<210> SEQ ID NO 33
<211> LENGTH: 1631
<212> TYPE: DNA
<213> ORGANISM: Homo sapiens
```

<400> SEQUENCE: 33

```
cccgccacgt gtccccggtc accggccctg cccccgggcc ctgtgcttat aacctgggat      60
gggcacccct gccagtcctg ctctgccgcc tgccaccgct gcccgagccc gacgctatgt     120
ccagcaaagg ctccgtggtt ctggcctaca gtggcggcct ggacacctcg tgcatcctcg     180
tgtggctgaa ggaacaaggc tatgacgtca ttgcctatct ggccaacatt ggccagaagg     240
aagacttcga ggaagccagg aagaaggcac tgaagcttgg ggccaaaaag gtgttcattg     300
aggatgtcag cagggagttt gtggaggagt tcatctggcc ggccatccag tccagcgcac     360
tgtatgagga ccgctacctc ctgggcacct ctcttgccag ccctgcatc gcccgcaaac      420
aagtggaaat cgcccagcgg gaggggccca agtatgtgtc ccacggcgcc acaggaaagg     480
ggaacgatca ggtccggttt gagctcagct gctactcact ggccccccag ataaaggtca     540
ttgctccctg gaggatgcct gaattctaca accggttcaa gggccgcaat gacctgatgg     600
agtacgcaaa gcaacacggg attcccatcc cggtcactcc caagaacccg tggagcatgg     660
atgagaacct catgcacatc agctacgagg ctggaatcct ggagaacccc aagaaccaag     720
cgcctccagg tctctacacg aagacccagg acccagccaa agcccccaac accccctgaca    780
ttctcgagat cgagttcaaa aaggggtcc ctgtgaaggt gaccaacgtc aaggatggca      840
ccacccacca gacctccttg gagctcttca tgtacctgaa cgaagtcgcg ggcaagcatg     900
gcgtgggccg tattgacatc gtggagaacc gcttcattgg aatgaagtcc gaggtatct     960
acgagacccc agcaggcacc atcctttacc atgctcattt agacatcgag gccttcacca    1020
tggaccggga agtgcgcaaa atcaaacaag gcctgggctt gaaatttgct gagctggtgt    1080
ataccggttt ctggcacagc cctgagtgtg aatttgtccg ccactgcatc gccaagtccc    1140
aggagcgagt ggaagggaaa gtgcaggtgt ccgtcctcaa gggccaggtg tacatcctcg    1200
gccgggagtc cccactgtct ctctacaatg aggagctggt gagcatgaac gtgcagggtg    1260
attatgagcc aactgatgcc accgggttca tcaacatcaa ttccctcagg ctgaaggaat    1320
atcatcgtct ccagagcaag gtcactgcca aatagacccg tgtacaatga ggagctgggg    1380
cctcctcaat ttgcagatcc cccaagtaca ggcgctaatt gttgtgataa tttgtaattg    1440
tgacttgttc tccccggctg gcagcgtagt ggggctgcca ggcccagct tgttccctg      1500
gtcccctga agcctgcaaa cgttgtcatc gaagggaagg gtgggggca gctgcggtgg      1560
ggagctataa aaatgacaat taaaagagac actagtcttt tatttctaaa aaaaaaaaaa    1620
aaaaaaaaa a                                                          1631
```

<210> SEQ ID NO 34
<211> LENGTH: 1645
<212> TYPE: DNA
<213> ORGANISM: Mus musculus

<400> SEQUENCE: 34

```
gcttataacc ctggatgcgc gcctctctca gccctgctcc gccgtctgcc actgccgcct      60
gggctcactg agtggttcat ctggccagga aagcagacta cacggactcc agggacctgt    120
acctataatc caagacaaga tgtccagcaa gggctctgtg ttctggcct acagtggtgg     180
cctggacacc tcctgcatcc tcgtgtggct gaaggaacaa ggctatgatg tcatcgccta    240
cctggccaac attggccaga aggaagactt tgaggaagcc aggaagaagg cgctgaagct    300
tggggccaaa aaggtgttca ttgaggatgt gagcaaggaa tttgtggaag agttcatctg    360
gcctgctgtc cagtccagtg cactctacga ggaccgctat ctcctgggca cctctctcgc    420
```

```
caggccttgc atagctcgca gacaggtgga gattgcccag cgtgaagggg ccaagtatgt      480
gtctcacggc gccacgggaa aggggaatga ccaggtccgc tttgagctca cctgctactc      540
actggcaccc cagattaagg tcatcgctcc ctggaggatg cctgagtttt acaaccggtt      600
caagggccga aatgatctga tggagtatgc aaagcaacac ggaatcccca tccctgtcac      660
ccccaagagc ccctggagta tggatgaaaa cctcatgcac atcagctatg aggctgggat      720
cctggaaaac cccaagaatc aagcacctcc gggtctctac acaaaaactc aggaccctgc      780
caaagcaccc aacagcccag atgtccttga datagaattc aaaaaagggg tccctgtgaa      840
ggtgaccaac atcaaagatg cacaacccg caccacatcc ctggaactct tcatgtacct      900
gaacgaagtt gcgggcaagc acggagtggg tcgcattgac atcgtggaga accgcttcat      960
tggaatgaag tcccgaggta tctacgagac cccagcaggg accatccttt accacgctca     1020
tttagacata gaggccttca cgatggatcg ggaagtacgc aaaatcaagc agggcctggg     1080
cctcaaattc gcagagctcg tatacacagg tttctggcac agccctgaat gtgaatttgt     1140
tcgccactgt atccagaagt cccaggagcg ggtagaaggg aaggtgcagg tgtctgtctt     1200
caagggccaa gtgtacatcc tcggtcggga gtctccactt tcactctaca atgaagagct     1260
ggtgagcatg aacgtacagg gcgactatga gcccatcgac gccactggct tcatcaatat     1320
caactcgctc aggctgaagg agtaccatcc ccttcagagc aaggtcactg ccaaatagac     1380
cctgacaaag aggagcgggc ctccccactc tgcagctctc ccaggcttca gcattaattg     1440
ttgtgataaa tttgtaattg tagcttgttc tccaccacct gactgggct gctgtgtccc      1500 ccccgccccc ccacagcctt tgttccctgg tcccctatag cctacaaaag tggtcatcga     1560
agggaaggga gggtggcggg cagctgcaga aagcataaaa tgacaattaa agaagttac      1620 attagtcttt aaaaaaaaaa aaaaa                                           1645
```

<210> SEQ ID NO 35
<211> LENGTH: 1694
<212> TYPE: DNA
<213> ORGANISM: Rattus norvegicus

<400> SEQUENCE: 35

```
ggggccccca ggccctgtgc ttataaccct ggatgcgcgc ctctcccggt cctgctccgc       60
tgttcgccac tgccgcctgg gctcactgag tggttcaccc ggccaggaag acagactacg      120
gactccaggg acctgtagct acaatccaag acaagatgtc cagcaagggc tctgtggttc      180
tggcctacag tggtggtctg gacacctcct gcatcctcgt gtggctgaag gaacaaggct      240
atgatgtcat cgcctacctg gccaacattg gccagaagga agactttgag gaagccagga      300
agaaggcact gaagcttggg gccaaaaagg tgttcattga ggatgtaagc aaggagtttg      360
tggaagagtt catctggcct gctgtccagt ccagtgcact ctatgaggac cgctatctcc      420
taggcacctc tctcgccagg ccttgcatag ctcgcaaaca agtggaaatt gcccagcgcg      480
aaggggccaa gtatgtgtct cacggcgcca cggggaaggg caatgaccag gtccgctttg      540
agctcacctg ctactcgtta gcaccccaga ttaaggtcat cgcccctgg aggatgcccg      600 agttttacaa ccggttcaag ggccgaaatg atttgatgga atacgcaaag caacatggaa      660
tccccatccc tgtcaccccc aagagcccct ggagcatgga tgagaacctt atgcacatca      720
gctacgaggc tggaatcctg gaaaacccca gaaccaagc acctccaggt ctctacacaa      780
aaactcagga ccctgccaaa gcacccaaca ccccagatgt ccttgagata gaattcaaaa      840 aagggggtccc tgtgaaggtg accaacgtca agatggcac tacccacagc acatccttgg      900
```

-continued

```
acctcttcat gtacctgaat gaagttgcgg gcaagcatgg agtagggcgc attgacatcg    960
tggagaaccg cttcattgga atgaagtccc ggggtatcta cgagacccca gcagggacca   1020
tcctttacca cgctcattta gacatagagg ccttcaccat ggatcgggaa gtacgcaaaa   1080
tcaagcaggg cctgggcctc aaattcgcag agctcgtata caccggtttc tggcacagcc   1140
ctgaatgtga atttgttcgc cactgcatcg acaagtccca ggaacgggtg gaaggaaagg   1200
tgcaggtatc tgtcttcaag ggccaggtgt acatccttgg ccgggagtct ccactttcac   1260
tatacaatga agagctggtg agcatgaacg tacagggtga ctatgaaccc attgatgcca   1320
ccggcttcat caatatcaac tcgctcaggc tgaaggagta ccatcgcctt cagagcaagg   1380
tcaccgccaa atagaccgtg acaaagaggc gcgggcctcc ccgctctgca gctctcccag   1440
gctccagcat taattgttgt gataaatttg taattgtagc ttgttctcct accacctgac   1500
tggggctgct gtgccccccc tcacctcccc cccacccaca ggctttgttc cctggtcccc   1560
tatagcctac aaaagtggtc atcgaaggga agggggggtg gcaggcagct gcagaaagcg   1620
cgtaaaatga caattaaaag aagttacatt agtaaaaaaa ataaaaaaaa aaaaaaaaa    1680 aaaaaaaaaa aaaa                                                     1694
```

POLYNUCLEOTIDES TARGETED AGAINST THE EXTENDED 5'-UTR REGION OF ARGININOSUCCINATE SYNTHASE AND USES THEREOF

CROSS-REFERENCE TO RELATED APPLICATION

The present application claims the benefit of U.S. Provisional Application Ser. No. 60/647,750, filed Jan. 27, 2005, which is hereby incorporated by reference herein in its entirety, including any figures, tables, nucleic acid sequences, amino acid sequences, and drawings.

BACKGROUND OF THE INVENTION

Nitric oxide (NO) synthesized from arginine by endothelial nitric oxide synthase (eNOS) is a potent vasodilator and a critical modulator of blood flow and blood pressure. In addition, it mediates vasoprotective actions through inhibiting smooth muscle proliferation, platelet aggregation, and leukocyte adhesion (Bredt, D. S. and Snyder, S. H. *Annu. Rev. Biochem.*, 1994, 63:175-195; Gow, A. J. and Ischiropoulos, H. *J. Cell. Physiol.*, 2001, 187:277-282; Vallance, P. and Chan, N. *Heart,* 2001, 85:342-50). Under pathophysiological conditions associated with endothelial dysfunction, such as heart failure (Sharma, R. and Davidoff, M. N. *Congest. Heart Fail.*, 2002, 8:165-172), hypertension, hypercholesterolemia, atherosclerosis (Maxwell, A. J. *Nitric Oxide,* 2002, 6:101-124), and diabetes (Goligorsky, M. S. and Gross, S. S. *Drug News Perspect.*, 2001, 14:133-142), the ability to produce NO seems to be impaired. One suggested reason for this impairment has been the reduced availability of the substrate arginine, despite saturating levels of intracellular and extracellular arginine.

The present inventors have previously shown that, under normal conditions, the essential arginine available for NO production is derived from the recycling of citrulline back to arginine, catalyzed by two enzymes, argininosuccinate synthase (AS) and argininosuccinate lyase (AL) (Flam, B. R. et al. *Nitric Oxide,* 2001, 5:187-197; Pendleton, L. C. et al. *J. Biol. Chem.*, 2002, 277:25363-25369; Goodwin, B. L. et al. *J. Biol. Chem.*, 2004, 279:18353-18360). Although these two enzymes have been studied extensively in the liver where they participate in the urea cycle (Morris, S. M., Jr. *Annu. Rev. Nutr.*, 1992, 12:81-101), it was not until the discovery of NO that their function in non-hepatic tissue was clarified.

Because AS catalyzes the rate-limiting step in the citrulline-NO cycle (Xie, L. and Gross, S. S. *J. Biol. Chem.*, 1997, 272:16624-16630), the present inventors' initial studies have focused on the molecular basis for the functional role of endothelial AS. Endothelial and hepatic AS appear to have the same primary structure (Pendleton, L. C. et al. *J. Biol. Chem.*, 2002, 277:25363-25369; Freytag, S. O. et al. *J. Biol. Chem.*, 1984, 259:3160-31662), but differ in cellular location and level of expression (Flam, B. R. et al. *Nitric Oxide,* 2001, 5:187-197; Pendleton, L. C. et al. *J. Biol. Chem.*, 2002, 277: 25363-25369). Hepatic urea cycle AS and AL are associated with the mitochondria (Cohen, N. S. and Kuda, A. J *Cell. Biochem.*, 1996, 60:334-340), while in endothelial cells, AS and AL co-localize with eNOS in caveolae (Flam, B. R. et al. *Nitric Oxide,* 2001, 5:187-197).

AS expression in liver also differs from AS expression in endothelial cells as demonstrated by the diversity of 5'-UTR AS mRNA species in endothelial cells (Pendleton, L. C. et al. *J. Biol. Chem.*, 2002, 277:25363-25369). Three transcription initiation sites identified in endothelial cells result in overlapping 5'-UTR regions of 92, 66 and 43 nucleotides (nt). The longer forms make up ~7% of the total AS message, with the shortest 43 nt 5'-UTR AS mRNA being the predominant species in endothelial cells, and the only detectable form found in liver. The extended 92 and 66 nt 5'-UTR AS mRNAs contain an out-of-frame, upstream overlapping ORF that is terminated by a stop codon 70 nt past the in-frame start codon for the downstream ORF encoding AS. Previously, the present inventors reported that in vitro translation of AS mRNA containing the extended 5'-UTRs was suppressed compared to the shortest and most predominant 43 nt 5'-UTR AS mRNA species (Pendleton, L. C. et al. *J. Biol. Chem.*, 2002, 277:25363-25369). Moreover, it was also showed that the translational efficiency of the extended 5'-UTR AS mRNA species was restored to short form levels when the uAUG was mutated to AAG, thus eliminating the uORF (Pendleton, L. C. et al. *J. Biol. Chem.*, 2002, 277:25363-25369).

Upstream ORFs can act as cis-acting factors affecting the translation of a downstream ORF in a variety of ways (Morris, D. R. and Geballe, A. P. *Mol. Cell. Biol.*, 2000, 20:8635-8642). In higher eukaryotes, initiation of translation generally occurs at the first AUG that resides in a favorable context. When the first AUG context is suboptimal, a portion of the scanning ribosomes may continue past the first AUG and initiate translation downstream at subsequent AUGs via leaky scanning (Kozak, M. *Gene,* 1999, 234:187-208). In this context, a significant number of eukaryotic mRNAs have now been reported that contain one or more upstream ORFs shown to affect the translational efficiency of the main, downstream ORF (Morris, D. R. and Geballe, A. P. *Mol. Cell. Biol.*, 2000, 20:8635-8642). Depending on conditions such as intercistronic length and secondary structure, scanning ribosomes, upon initiation at the uAUG, can either translate the uORF and reinitiate downstream or stall on the mRNA during elongation, thus preventing initiation at other sites (Morris, D. R. and Geballe, A. P. *Mol. Cell. Biol.*, 2000, 20:8635-8642). In other cases, partial translation of the nascent peptide prevents downstream re-initiation by interaction of the peptide with a protein or RNA in the ribosome preventing termination from proceeding efficiently (Gaba, A. et al. *Embo. J.*, 2001, 20:6453-6463). Another less common event is for the uORF to be translated and for the peptide product to affect translation of the downstream cistron via a trans mechanism (Parola, A. L. and Kobilka, B. K. *J. Biol. Chem.*, 1994, 269:4497-4505).

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., *Nature* 391:806-11 (1998); Sharp, *Genes Dev.* 13:139-41 (1999); Elbashir et al. *Nature* 411:494-98 (2001); Harborth et al., *J. Cell Sci.* 114:4557-65 (2001)). RNAi is mediated by double-stranded polynucleotides as also described hereinbelow, for example, double-stranded RNA (dsRNA), having sequences that correspond to exonic sequences encoding portions of the polypeptides for which expression is compromised. RNAi reportedly is not effected by double-stranded RNA polynucleotides that share sequence identity with intronic or promoter sequences (Elbashir et al., 2001). RNAi pathways have been best characterized in *Drosophila* and *Caenorhabditis elegans*, but "small interfering RNA" (siRNA) polynucleotides that interfere with expression of specific polynucleotides in higher eukaryotes such as mammals (including humans) have also been considered (e.g., Tuschl, 2001 *Chembiochem.* 2:239-245;

Sharp, 2001 *Genes Dev.* 15:485; Bernstein et al., 2001 *RNA* 7:1509; Zamore, 2002 *Science* 296:1265; Plasterk, 2002 *Science* 296:1263; Zamore 2001 *Nat. Struct. Biol.* 8:746; Matzke et al., 2001 *Science* 293:1080; Scadden et al., 2001 *EMBO Rep.* 2:1107).

According to a current non-limiting model, the RNAi pathway is initiated by ATP-dependent, cleavage of long dsRNA into double-stranded fragments of about 18-27 (e.g., 19, 20, 21, 22, 23, 24, 25, 26, etc.) nucleotide base pairs in length, called small interfering RNAs (siRNAs) (see review by Hutvagner et al., *Curr. Opin. Gen. Dev.* 12:225-32 (2002); Elbashir et al., 2001; Nyknen et al., *Cell* 107:309-21 (2001); Zamore et al., *Cell* 101:25-33 (2000)). In Drosophila, an enzyme known as "Dicer" cleaves the longer double-stranded RNA into siRNAs; Dicer belongs to the RNase III family of dsRNA-specific endonucleases (WO 01/68836; Bernstein et al., *Nature* 409:363-66 (2001)). Further, according to this non-limiting model, the siRNA duplexes are incorporated into a protein complex, followed by ATP-dependent unwinding of the siRNA, which then generates an active RNA-induced silencing complex (RISC) (WO 01/68836). The complex recognizes and cleaves a target RNA that is complementary to the guide strand of the siRNA, thus interfering with expression of a specific protein (Hutvagner et al., supra).

In *C. elegans* and *Drosophila*, RNAi may be mediated by long double-stranded RNA polynucleotides (WO 99/32619; WO 01/75164; Fire et al., 1998; Clemens et al., *Proc. Natl. Acad. Sci. USA* 97:6499-6503 (2000); Kisielow et al., *Biochem. J.* 363:1-5 (2002); see also WO 01/92513 (RNAi-mediated silencing in yeast)). In mammalian cells, however, transfection with long dsRNA polynucleotides (i.e., greater than 30 base pairs) leads to activation of a non-specific sequence response that globally blocks the initiation of protein synthesis and causes mRNA degradation (Bass, *Nature* 411:428-29 (2001)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., *Genes Dev.* 15:188-200 (2001)); Harborth et al., *J. Cell Sci.* 114:4557-65 (2001); Carthew et al., *Curr. Opin. Cell Biol.* 13:244-48 (2001); Mailand et al., *Nature Cell Biol.* Advance Online Publication (Mar. 18, 2002); Mailand et al. 2002 *Nature Cell Biol.* 4:317).

siRNA polynucleotides may offer certain advantages over other polynucleotides known to the art for use in sequence-specific alteration or modulation of gene expression to yield altered levels of an encoded polypeptide product. These advantages include lower effective siRNA polynucleotide concentrations, enhanced siRNA polynucleotide stability, and shorter siRNA polynucleotide oligonucleotide lengths relative to such other polynucleotides (e.g., antisense, ribozyme or triplex polynucleotides). By way of a brief background, "antisense" polynucleotides bind in a sequence-specific manner to target nucleic acids, such as mRNA or DNA, to prevent transcription of DNA or translation of the mRNA (see, e.g., U.S. Pat. Nos. 5,168,053; 5,190,931; 5,135,917; 5,087,617; see also, e.g., Clusel et al., 1993 *Nuc. Acids Res.* 21:3405-11, describing "dumbbell" antisense oligonucleotides). "Ribozyme" polynucleotides can be targeted to any RNA transcript and are capable of catalytically cleaving such transcripts, thus impairing translation of mRNA (see, e.g., U.S. Pat. Nos. 5,272,262; 5,144,019; and 5,168,053, 5,180, 818, 5,116,742 and 5,093,246; U.S. Ser. No. 2002/193579). "Triplex" DNA molecules refers to single DNA strands that bind duplex DNA to form a colinear triplex molecule, thereby preventing transcription (see, e.g., U.S. Pat. No. 5,176,996, describing methods for making synthetic oligonucleotides that bind to target sites on duplex DNA). Such triple-stranded structures are unstable and form only transiently under physiological conditions. Because single-stranded polynucleotides do not readily diffuse into cells and are therefore susceptible to nuclease digestion, development of single-stranded DNA for antisense or triplex technologies often requires chemically modified nucleotides to improve stability and absorption by cells. siRNAs, by contrast, are readily taken up by intact cells, are effective at interfering with the expression of specific polynucleotides at concentrations that are several orders of magnitude lower than those required for either antisense or ribozyme polynucleotides, and do not require the use of chemically modified nucleotides.

BRIEF SUMMARY OF THE INVENTION

The present invention is based in part on the discovery that two mRNA variants of argininosuccinate synthase (AS) with different 5'-untranslated regions (5'UTRs) contain upstream open reading frame (uORF) that function to suppress expression of endogenous AS. It is now well established that AS catalyzes the rate-limiting step essential for recycling of citrulline back to arginine in order to maintain nitric oxide (NO) production. Furthermore, specific silencing of the uORF AS mRNAs results in the up-regulation of endogenous AS, as well as the production of NO by endothelial cells. Thus, the extended 5'-UTR AS mRNA species is a mechanism for regulating AS expression and NO production, and provides a target for the treatment of disorders associated with vascular endothelial dysfunction and characterized by impairment of NO production, such as heart failure, hypertension, hypercholesterolemia, atherosclerosis, and diabetes.

The present invention provides a method for increasing AS activity by specifically targeting the AS sequence in the extended 5'-UTR AS mRNA, representing positions −47 to −65 nt. In one aspect, the present concerns a method for increasing AS expression by administering a polynucleotide specific for the extended 5'-UTR AS mRNA to a subject, wherein the polynucleotide interferes with expression of the uORF by reducing its expression in a sequence-specific manner, to yield reduced levels of the long forms of AS mRNA and increased levels of AS. Because AS catalyzes the rate-limiting step in the citrulline-NO cycle, the polynucleotide also increases cellular production of NO. Thus, the method of the invention is useful in the treatment of human or non-human animal subjects suffering from, or at risk of developing, disorders associated with vascular endothelial dysfunction and characterized by impairment of NO production, such as heart failure, hypertension, hypercholesterolemia, atherosclerosis, and diabetes. In addition, the method of the invention is useful in the treatment of human or non-human animal subjects suffering from, or at risk of developing, disorders associated with argininosuccinate synthetase deficiency, such as citrullinemia and/or hyperammonemia.

In another aspect, the present invention provides a polynucleotide specific for the extended 5'-UTR AS mRNA region, relative to the first nucleotide of the translation start codon for the AS open reading frame, wherein the polynucleotide interferes with expression of the upstream open reading frame (uORF) of the extended 5'UTR AS mRNA species. Preferably, the polynucleotide is a silencing double stranded ribonucleic acid (RNA) sequence, also called a small interfering RNA (siRNA) that causes degradation of the targeted RNA. Thus, in one embodiment, the polynucleotide is a double stranded ribonucleic acid (dsRNA) that inhibits expression of the uORF of the extended 5'-UTR AS. In a specific embodiment, the 5'UTR is a nucleotide sequence of NM_054012 (Human), NM_007494 (Mouse), or BC063146 (Rat), wherein a first strand of the dsRNA is substantially identical 19 to 49 consecutive nucleotides of the 5'UTR disclosed in Pendleton et al. (*J. Biol. Chem.*, 2002, 277:25363-25369), which is incorporated herein by reference, and a second strand of the dsRNA is substantially complementary to the first. In another embodiment, the polynucleotide is a double-stranded ribonucleic acid (dsRNA) comprising a first strand of nucleotides that is substantially identical to 19 to 25 consecutive nucleotides of the 5'UTR disclosed in Pendleton et al. (*J. Biol. Chem.*, 2002, 277: 25363-25369), and a second strand that is substantially complementary to the first strand. In another embodiment, the polynucleotide is a double-stranded ribonucleic acid (dsRNA) comprising a first strand of nucleotides including the sequence 5'-CCC GGG AUG CGC GCC GAA AUU 3' (SEQ ID NO:1) (Pendleton et al., *J. Biol. Chem.*, 2002, 277: 25363-25369), and a second strand of nucleotides comprising a sequence substantially complementary to the first.

In another embodiment, the polynucleotide of the invention is a dsRNA comprising a first strand of nucleotides of at least 16 nucleotides sufficiently complementary to a target region of the uORF of an extended 5'UTR AS mRNA sequence to direct target-specific RNA interference (RNAi), and a second strand of nucleotides of at least 16 nucleotides substantially complementary to the first strand. In a further embodiment, the first strand is fully complementary to the target region of the extended 5'-UTR AS mRNA sequence. In another embodiment, the dsRNA further comprises a loop formation comprising 4-11 nucleotides that connects the first and second strands. In a specific embodiment, the first and second strands each comprise 16, 17, 18, 19, 20, 21, 22, 23, 24, or 25 nucleotides. In another specific embodiment, the first and second strands each consist of 16, 17, 18, 19, 20, 21, 22, 23, 24, or 25 nucleotides.

In other embodiments, the polynucleotide of the invention is an antisense nucleic acid sequence (e.g., a single stranded oligonucleotide) that is complementary to a target region within the uORF of the extended 5'UTR AS mRNA, which binds to the target region and inhibits translation. The antisense oligonucleotide may be DNA or RNA, or comprise synthetic analogs of ribo-deoxynucleotides. Thus, the antisense oligonucleotide reduces endogenous expression of the uORF of the extended 5'UTR AS mRNA species. In one embodiment, the antisense oligonucleotide consists of 8 nucleotides complementary to contiguous nucleotides within the extended 5'UTR AS mRNAs. In other embodiments, the oligonucleotide has a length of 9, 10, 11, 12, 13, 14, 15, or 16 nucleotides.

In other embodiments, the polynucleotide of the invention is an RNA molecule having enzymatic activity (a ribozyme) that inhibits expression of the uORF of the extended 5'UTR AS. In one embodiment, the ribozyme comprises a 5'-end flanking region having 4-50 nucleotides and being complementary to a 3'-end target region within the uORF of the extended 5'UTR AS RNA; a stem-loop region, comprising a stem portion having 2-12 nucleotide pairs and a loop portion comprising at least 2 unpaired nucleotides; and a 3'-end flanking region having 4-50 nucleotides and being complementary to a 5'end target site on the substrate RNA.

For the polynucleotides of the subject invention (e.g., siRNA, antisense oligonucleotides, and ribozymes), the target region within the uORF of the extended 5'UTR AS may represent any position between −44 and −66. In one embodiment, the target region within the uORF of the extended 5'UTR AS is nucleotide position −47 to −65 (as shown in FIG. 1), relative to the first nucleotide of the start codon.

Other aspects of the invention include vectors (e.g., viral vectors, expression cassettes, plasmids) comprising or encoding polynucleotides of the subject invention (e.g., siRNA, antisense nucleic acids, and ribozymes), and host cells genetically modified with polynucleotides or vectors of the subject invention. In one embodiment, the vector comprises a polynucleotide and an expression control sequences that directs production of a transcript that hybridizes under physiological conditions to a target region within the extended 5'UTR AS mRNA. In one embodiment, the host cell is an endothelial cell, such as a vascular endothelial cell.

Another aspect of the invention includes a method for identifying an agent that modulates expression of extended 5'-UTR AS mRNA, comprising contacting a sample comprising 5'-UTR AS mRNA with a test agent; and determining whether the test agent modulates expression of the 5'-UTR AS mRNA. Another aspect of the invention includes a method for identifying an agent that increases NO production, comprising contacting a sample comprising 5'UTR AS mRNA with a test agent; and determining whether the test agent modulates expression of the 5'-UTR AS mRNA, wherein a reduction of 5'-UTR AS mRNA expression is indicative of an agent that increases NO production. Optionally, the latter method further comprises determining the level of NO protein or NO mRNA in the sample subsequent to the contacting of the sample and test agent. In both of the aforementioned methods, the sample can be a cell (such as a vascular endothelial cell), tissue, or organ. In both of the aforementioned methods, the test agent can be, for example, a small molecule, mineral, polypeptide, amino acid, hormone, polynucleotide (such as an interfering RNA, anti-sense oligonucleotide, or ribozyme), lipid, carbohydrate, vitamin, or co-enzyme.

BRIEF DESCRIPTION OF THE DRAWINGS

FIGS. 9A-9C show the effect of silencing of the extended 5'-UTR AS mRNAs on endothelial AS expression. BAEC were transiently transfected with siRNA specific for the 92 and 66 nt 5'-UTR species of AS mRNA (♦) and a scrambled negative control siRNA (■). Total RNA was isolated and AS mRNA was detected by real time RT-PCR. Primer sets were designed to specifically amplify the 66 and 92 nt 5'-UTR species, shown in FIG. 9A, or total AS message, shown in FIG. 9B. Equal amounts of protein were separated by SDS-PAGE and standard western blotting was performed using anti-AS and anti-GAPDH antibodies. Quantitation of AS protein expression, normalized to GAPDH, from four separate experiments is shown in FIG. 9C.

FIG. 10 shows extended 5'-UTR sequence comparisons. To determine the possible genomic origin of the endothelial-specific AS 5'-UTR species, these sequences were compared with the 5'-UTR and genomic 5'-flanking regions from human and mouse (Jinno Y. et al., *J. Biochem.* (Tokyo), 98:1395-1403; and Surh L. C. et al., *Gene*, 1991, 99:181-189; each of which are incorporated herein by reference in their entirety). Comparison of the 43-nt bovine AS mRNA 5'-UTR with exon 1 from human and mouse AS gene sequences demonstrated 72% and 64% homology, respectively. When a comparison was made of the 92-nt 5'UTR from endothelial AS mRNA with the 5'-flanking genomic sequence from human and mouse, the percentage of homology increased to 78% and 71%, respectively. A sequence of 10 nt surrounding the TATTA box was identical in all three species. Importantly, the upstream AUG found in the extended 5'-TUR AS mRNAs from bovine endothelial cells was distinctly identified in the 5'-flanking genomic regions of both human and mouse AS genes. FIG. 10 shows sequences from bovine AS mRNA 5'-UTRs (SEQ ID NO:27) compared with genomic AS 5'-flanking regions and 5'-UTRs from human (SEQ ID NO:28) and mouse (SEQ ID NO:29). Bovine transcription start sites as well as the translational start codon are indicated by an arrow and a label above the sequence. The underlined sequence denotes human and mouse exon 1. Boxed areas indicate sequence with 100% homology between the three species (reproduced from Pendleton, L. C. et al. *J. Biol. Chem.*, 2002, 277:25363-25369).

FIG. 11 shows a schematic of a typical hairpin siRNA produced by an siRNA expression cassette and its relationship to the RNA target sequence (AMBION website).

FIG. 12 shows an insert design for pSILENCER 2.0-U6 and pSILENCER 3.0-Hi (AMBION website) (SEQ ID NOs: 30-3 1). The insert design is usable with the pSILENCER 2.0-U6, 2.1-U6, 3.0-H1, and 3.1-H1 expression vectors and contains the appropriate overhanging 5' ends for directional cloning into these plasmids.

FIG. 14 shows a portion of the human sequence (SEQ ID NO:32) for AS 5'-UTR extended form from GenBank accession no. NM_054012, which is incorporated herein by reference in its entirety.

FIG. 17 shows the human sequence of AS (SEQ ID NO:33).

FIG. 18 shows the mouse sequence of AS (SEQ ID NO:34).

FIG. 19 shows the rat sequence of AS (SEQ ID NO:35).

BRIEF DESCRIPTION OF THE SEQUENCES

Figure 1:
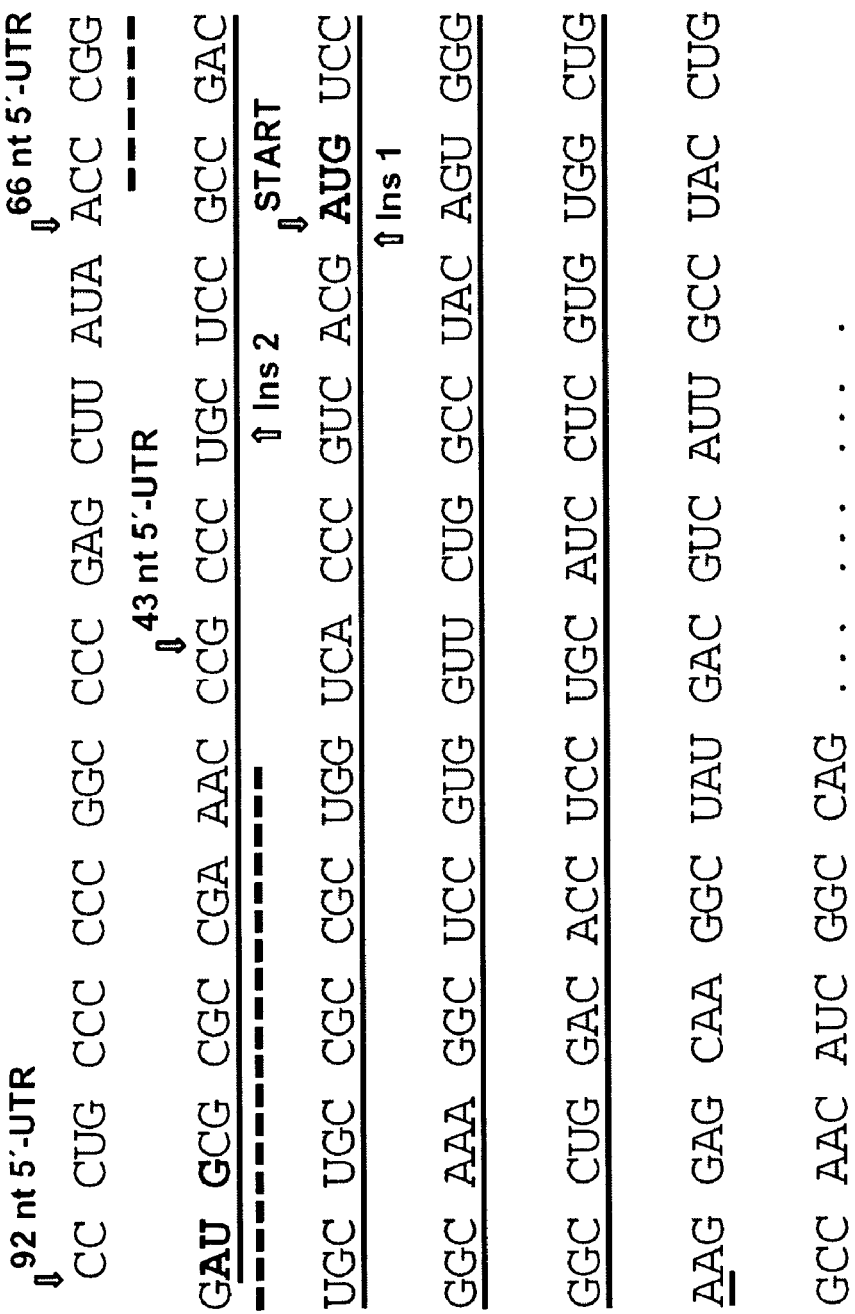
FIG. 1 shows the diverse 5' leader sequence of endothelial AS mRNA (SEQ ID NO:26). The three endothelial AS transcription start sites are indicated by arrows and labeled. The AS AUG and the upstream out-of-frame AUG are in bold type. The upstream AUG and the uORF are underlined. Insertion mutation sites are marked by arrows and labeled Ins 1 and Ins 2. The site of the RNA duplex designed to knock down the extended 5'-UTR forms of the AS mRNA is underlined by a dashed line.

SEQ ID NO:1 is an interfering RNA sequence targeting bovine extended 5'-UTR AS mRNA.
SEQ ID NO:2 is the left primer ASL-11MFS.
SEQ ID NO:3 is the left primer ASL-48MFS.
SEQ ID NO:4 is the right primer ASR429.
SEQ ID NO:5 is the left primer ASL59MStop.
SEQ ID NO:6 is the right primer ASR168MStop.
SEQ ID NO:7 is the left primer LucASL-66.
SEQ ID NO:8 is the left primer LucASL-92.
SEQ ID NO:9 is the right primer RTLuc1R.
SEQ ID NO:10 is the left primer ASL-92BamHI.
SEQ ID NO:11 is the left primer ASL-43BamHI.
SEQ ID NO:12 is the right primer ASR73EcoRI.
SEQ ID NO:13 is the primer uORFfsleft.
SEQ ID NO:14 is the primer uORFfsright.
SEQ ID NO:15 is the primer uORFdnsAUG.
SEQ ID NO:16 is the primer uORFupsStop.
SEQ ID NO:17 is the primer GFPleft.
SEQ ID NO:18 is the primer GFPright.
SEQ ID NO:19 is a scrambled control for AS siRNA sequence.
SEQ ID NO:20 is the primer β-actin forward.
SEQ ID NO:21 is the primer β-actin reverse.
SEQ ID NO:22 is a siRNA targeting human extended 5'-UTR AS mRNA.
SEQ ID NO:23 is the sense strand of a siRNA targeting human extended 5'-UTR AS mRNA.
SEQ ID NO:24 is the anti-sense strand of a siRNA targeting human extended 5'-UTR AS mRNA.
SEQ ID NO:25 is a target sequence within the human AS 5'-UTR extended form (GenBank accession no. NM_054012).
SEQ ID NO:26 is the 5' leader sequence of endothelial AS mRNA, including target site for interfering RNA (FIG. 1).
SEQ ID NO:27 contains regions of bovine AS mRNA 5'-UTR (FIG. 10).
SEQ ID NO:28 contains regions of human AS mRNA 5'-UTR (FIG. 10).
SEQ ID NO:29 contains regions of mouse AS mRNA 5'-UTR (FIG. 10).
SEQ ID NO:30 is the bottom portion of the pSILENCER 2.1-U6neo vector map (FIG. 12).
SEQ ID NO:31 is the top portion of the pSILENCER 2.1-U6neo vector map (FIG. 12).
SEQ ID NO:32 is a portion of the human sequence for AS 5'-UTR extended form.
SEQ ID NO:33 is the human sequence of AS.
SEQ ID NO:34 is the mouse sequence of AS.
SEQ ID NO:35 is the rat sequence of AS.

DETAILED DESCRIPTION OF THE INVENTION

Argininosuccinate synthase (AS) catalyzes the rate-limiting step in the recycling of citrulline to arginine, which in endothelial cells, is coupled to the production of nitric oxide (NO). Previous work from the present inventors has established that endothelial AS mRNA can be initiated from multiple start sites, generating mRNA variants with different 5'-untranslated regions (5'-UTRs). The function of these individual mRNA variants is not known. Although one of the 5'-UTRs is predominant, representing greater than 90% of the total AS mRNA, two other extended 5'-UTR forms of message, resulting from upstream initiations, contain an out-of-frame, upstream open-reading-frame (uORF). In this study, the function of the extended 5'-UTRs of AS mRNA was investigated. Single base insertions to place the uORF in-frame, and mutations to extend the uORF, demonstrated functionality, both in vitro with AS constructs and in vivo with luciferase constructs. Over-expression of the uORF, suppressed endogenous AS expression, while specific silencing of the uORF AS mRNAs resulted in the upregulation of AS and NO production. Interestingly, the precise sequence (or the length of the uORF-encoded peptide) is important for its trans effect on overall AS expression, consistent with the idea that the translation product itself contributes to the regulation, rather than ribosomal recruitment to its initiation codon. In conclusion, the uORF in the extended, overlapping 5'-UTR AS mRNA species limits AS expression, providing a novel mechanism for regulating NO production in endothelial cells by limiting the availability of arginine.

Based at least in part on the above findings, the present invention relates to methods of increasing the activity of AS and, consequently, increasing NO production. In one aspect, the invention provides a method for reducing expression of the upstream open-reading-frame (uORF) of the extended 5'-untranslated regions (5'-UTRs) of AS in a subject by administering to the subject an effective amount of a polynucleotide, such as an siRNA, an antisense nucleotide sequence or strand, and/or a ribozyme, which selectively interferes with expression of the uORF of the extended 5'-UTRs of AS.

Another aspect of the invention includes a method for identifying an agent that modulates expression of extended 5'-UTR AS mRNA, comprising contacting a sample comprising 5'-UTR AS mRNA with a test agent; and determining whether the test agent modulates expression of the 5'-UTR AS mRNA. Another aspect of the invention includes a method for identifying an agent that increases NO production, comprising contacting a sample comprising 5'UTR AS mRNA with a test agent; and determining whether the test agent modulates expression of the 5'-UTR AS mRNA, wherein a reduction of 5'-UTR AS mRNA expression is indicative of an agent that increases NO production. Optionally, the latter method further comprises determining the level of NO protein or NO mRNA in the sample subsequent to the contacting of the sample and test agent.

In both of the aforementioned identification methods, the sample can be a cell (such as a vascular endothelial cell), tissue, or organ. The cells can be any cells that contain the uORF of the extended 5'-UTR AS mRNA. In one embodiment, the cells are endothelial cells. In another embodiment, the cells are vascular endothelial cells. The cells may be primary cells, cultured cells, cells of a cell line, etc.

In both of the aforementioned identification methods, the test agent can be, for example, a small molecule, mineral, polypeptide, amino acid, hormone, polynucleotide (such as an interfering RNA, anti-sense oligonucleotide, or ribozyme), lipid, carbohydrate, vitamin, or co-enzyme.

In both of the aforementioned identification methods, the steps of determining whether there has been a modulation (change, up or down) in expression of the uORF of the extended 5'-UTR AS mRNA, or modulation in the production of NO, can be performed in a variety of different ways, including those described in the Examples herein. Numerous suitable techniques are known for analyzing gene expression. For example, gene expression can be determined directly by assessing protein expression of cells. Protein expression can be detected using immunological techniques, e.g., using antibodies that specifically bind the protein in assays such as immunofluorescence or immunohistochemical staining and analysis, enzyme-linked immunosorbent assay (ELISA), radioimmunoassay (RIA), immunoblotting (e.g., Western blotting), and like techniques. Expression also be determined by directly or indirectly measuring the amount of mRNA in a cellular sample using known techniques such as Northern blotting and PCR-based methods such as competitive quantitative reverse transcriptase PCR (Q-RT-PCR). Other suitable methods may also be employed.

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine.

The term "nucleotide" refers to a nucleoside having one or more phosphate groups joined in ester linkages to the sugar moiety. Exemplary nucleotides include nucleoside monophosphates, diphosphates and triphosphates.

The terms "polynucleotide" and "nucleic acid molecule" are used interchangeably herein and refer to a polymer of nucleotides joined together by a phosphodiester linkage between 5' and 3' carbon atoms. Polynucleotides of the subject invention include, for example, siRNA, antisense nucleic acids (antisense oligonucleotides), aptamers, ribozymes (catalytic RNA), and triplex-forming oligonucleotides (i.e., antigene).

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog" or "nucleic acid analog", also referred to herein as an altered nucleotide/nucleic acid or modified nucleotide/nucleic acid refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. For example, locked nucleic acids (LNA) are a class of nucleotide analogs possessing very high affinity and excellent specificity toward complementary DNA and RNA. LNA oligonucleotides have been applied as antisense molecules both in vitro and in vivo (Jepsen J. S. et al., *Oligonucleotides*, 2004, 14(2): 130-146).

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "operably-linked" or "operatively-linked" refers to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for an siRNA will typically have its own operably-linked promoter sequence.

The term "vector" is used to refer to any molecule (e.g., nucleic acid, plasmid, cationic lipid molecule, or virus) used to transfer coding information (e.g., a polynucleotide of the invention) to a host cell. The term "expression vector" refers to a vector that is suitable for use in a host cell (e.g., a subject's cell) and contains nucleic acid sequences which direct and/or control the expression of exogenous nucleic acid sequences. Expression includes, but is not limited to, processes such as transcription, translation, and RNA splicing, if introns are present.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

As used herein, the term "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

As used herein, the term "mismatch" refers to a basepair consisting of noncomplementary bases, e.g., not normal complementary G:C, A:T or A:U base pairs.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines, in an organism.

A gene "involved in" or "associated with" a disorder includes a gene, the normal or aberrant expression or function of which affects or causes a disease or disorder or at least one symptom of the disease or disorder. For example, impaired NO production in endothelial cells is associated with heart failure, hypertension, hypercholesterolemia, atherosclerosis, and diabetes. The polynucleotides, genetic constructs, pharmaceutical compositions, and methods of the invention are useful in increasing expression of AS in cells (e.g., endothelial cells) in vitro or in vivo, consequently causing increased NO production. Thus, the polynucleotides, genetic constructs, pharmaceutical compositions, and methods of the invention are useful in the treatment of human or non-human animal subjects suffering from, or at risk of developing, disorders associated with impaired NO production. In addition, the polynucleotides, genetic constructs, pharmaceutical compositions, and methods of the invention are useful in the treatment of human or non-human animal subjects suffering from, or at risk of developing, disorders associated with argininosuccinate synthetase deficiency, such as citrullinemia and/or hyperammonemia (see, for example, Beaudet, A. L., et al., *Adv. Hum. Genet.*, 15:161-196, (1986); Brusilow, S. W. & Horwich, A. L., The Molecular and Metabolic Basis of Inherited Disease, eds., Scriver, C. R., Beaudet, A. L., Sly, W. S., & Valle, D. (McGraw-Hill, New York), pp. 1187-1232, 1995; Tsung-Sheng, S. et al., *J. Clin. Invest.*, 70:1334-1339, 1982; Dennis, J. A. et al., *Proc. Natl. Acad. Sci. USA*, 86:7947-7951, 1989; and Lee, B. et al., *Proc. Natl. Acad Sci. USA*, 96:3981-3986, 1999).

The methods of the invention may include further steps. In some embodiments, a subject with the relevant condition or disease (e.g., disorders associated with impaired AS and/or NO production) is identified or a patient at risk for the condition or disease is identified. A patient may be someone who has not been diagnosed with the disease or condition (diagnosis, prognosis, and/or staging) or someone diagnosed with disease or condition (diagnosis, prognosis, monitoring, and/or staging), including someone treated for the disease or condition (prognosis, staging, and/or monitoring). Alternatively, the person may not have been diagnosed with the disease or condition but suspected of having the disease or condition based either on patient history or family history, or the exhibition or observation of characteristic symptoms.

As used herein, an "effective amount" of polynucleotide (e.g., an interfering RNA, an antisense nucleotide sequence or strand, and/or a ribozyme, which selectively interferes with expression of the uORF of the extended 5'-UTRs of AS) is that amount effective to bring about the physiological changes desired in the cells to which the polynucleotide is administered in vitro (e.g., ex vivo) or in vivo. The term "therapeutically effective amount" as used herein, means that amount of polynucleotide (e.g., an siRNA, an antisense oligonucleotide, and/or a ribozyme, which selectively interferes with expression of the uORF of the extended 5'-UTRs of AS), alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention of the symptoms of the disease or disorder being treated. Preferably, suppression of expression of the uORF of the extended 5'-UTRs of AS results in increased nitric oxide (NO).

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

RNA Interference

RNAi is an efficient process whereby double-stranded RNA (dsRNA, also referred to herein as siRNAs or ds siRNAs, for double-stranded small interfering RNAs) induces the sequence-specific degradation of targeted mRNA in animal and plant cells (Hutvagner and Zamore, *Curr. Opin. Genet. Dev.*: 12, 225-232 (2002); Sharp, *Genes Dev.*, 15:485-490 (2001)). In mammalian cells, RNAi can be triggered by 21-nucleotide (nt) duplexes of small interfering RNA (siRNA) (Chiu et al., *Mol. Cell.* 10:549-561 (2002); Elbashir et al., *Nature* 411:494-498 (2001)), or by micro-RNAs (miRNA), functional small-hairpin RNA (shRNA), or other dsRNAs which can be expressed in vivo using DNA templates with RNA polymerase III promoters (Zeng et al., *Mol. Cell* 9:1327-1333 (2002); Paddison et al., *Genes Dev.* 16:948-958 (2002); Lee et al., *Nature Biotechnol.* 20:500-505 (2002); Paul et al., *Nature Biotechnol.* 20:505-508 (2002); Tuschl, T., *Nature Biotechnol.* 20:440-448 (2002); Yu et al., *Proc. Natl. Acad. Sci. USA* 99(9):6047-6052 (2002); McManus et al., *RNA* 8:842-850 (2002); Sui et al., *Proc. Natl. Acad. Sci. USA* 99(6):5515-5520 (2002)), each of which are incorporated herein by reference in their entirety.

The scientific literature is replete with reports of endogenous and exogenous gene expression silencing using siRNA, highlighting their therapeutic potential (Gupta, S. et al. *PNAS*, 2004, 101:1927-1932; Takaku, H. *Antivir Chem. Chemother*, 2004, 15:57-65; Pardridge, W. M. *Expert Opin. Biol. Ther.*, 2004, 4:1103-1113; Zheng, B. J. *Antivir. Ther.*, 2004, 9:365-374; Shen, W. G. *Chin. Med. J. (Engl)*, 2004, 117:1084-1091; Fuchs, U. et al. *Curr. Mol. Med.*, 2004, 4:507-517; Wadhwa, R. et al. *Mutat. Res.*, 2004, 567:71-84; Ichim, T. E. et al. *Am. J. Transplant*, 2004, 4:1227-1236; Jana, S. et al. *Appl. Microbiol. Biotechnol.*, 2004, 65:649-657; Ryther, R. C. et al. *Gene Ther.*, 2005, 12:5-11; Chae, S-S. et al., *J. Clin. Invest.*, 2004, 114:1082-1089; Fougerolles, A. et al., Methods Enzymol., 2005, 392:278-296), each of which is incorporated herein by reference in its entirety. Therapeutic silencing of endogenous genes by systemic administration of siRNAs has been described in the literature (Kim B. et al., *American Journal of Pathology*, 2004, 165:2177-2185; Soutschek J. et al., *Nature*, 2004, 432:173-178; Pardridge W. M., *Expert Opin. Biol. Ther.*, Jul 4, 2004(7): 1103-1113), each of which is incorporated herein by reference in its entirety.

Accordingly, the invention includes such interfering RNA molecules that are targeted to the uORF in the extended, overlapping 5'-UTR AS mRNA species. The interfering RNA molecules are capable, when suitably introduced into or expressed within a cell that otherwise expresses the uORF in the extended, overlapping 5'-UTR AS mRNA species, of suppressing expression of the uORF in the extended, overlapping 5'-UTR AS mRNA by RNAi. The interfering RNA may be a double stranded siRNA. As the skilled person will appreciate, and as explained further herein, an siRNA molecule may include a short 3' DNA sequence also. Alternatively, the nucleic acid may be a DNA (usually double-stranded DNA) which, when transcribed in a cell, yields an RNA having two complementary portions joined via a spacer, such that the RNA takes the form of a hairpin when the complementary portions hybridize with each other. In a mammalian cell, the hairpin structure may be cleaved from the molecule by the enzyme DICER, to yield two distinct, but hybridized, RNA molecules.

Reduction (suppression) of expression results in a decrease of the extended 5'-UTR AS mRNA. For example, in a given cell, the suppression of the extended 5'-UTR AS mRNA by administration of a polynucleotide (e.g., interfering RNA, antisense oligonucleotide, or ribozyme) results in a decrease in the quantity of 5'-UTR AS mRNA relative to an untreated cell. Suppression may be partial. Preferred degrees of suppression are at least 50%, more preferably one of at least 60%, 70%, 80%, 85%, or 90%. A level of suppression between 90% and 100% is generally considered a "silencing" of expression. Where an increase in cellular production of nitric oxide (NO) is desired, the level of suppression is sufficient to increase NO.

In one embodiment, the invention provides an interfering RNA that is capable, when suitable introduced or expressed within a cell that otherwise expresses the uORF in the extended, overlapping 5'-UTR AS mRNA species, suppresses its expression by RNAi, wherein the interfering RNA is generally targeted to the sequence AACCTGGGATGGGCAC-CCCTG (SEQ ID NO:25). In a specific embodiment, interfering RNA comprises sequence AAC CCG GGA UGC GCG CCG AAA (SEQ ID NO:22). By the term "generally targeted" it is intended that the polynucleotide targets a sequence that overlaps with SEQ ID NO: 25 or other designated target sequence. In particular, the polynucleotide may target a sequence in the uORF in the extended, overlapping 5'-UTR AS mRNA that is slightly longer or shorter than SEQ ID NO:25 (preferably from 17-23 nucleotides in length), but is otherwise identical to SEQ ID NO:25.

It is expected that perfect identity/complementarity between the interfering RNA of the invention and the target sequence, although preferred, is not essential. Accordingly, the interfering RNA may include a single mismatch compared to the mRNA of the human uORF in the extended, overlapping 5'-UTR AS. It is expected, however, that the presence of even a single mismatch is likely to lead to reduced efficiency, so the absence of mismatches is preferred. When present, 3' overhangs may be excluded from the consideration of the number of mismatches.

The term "complementarity" is not limited to conventional base pairing between nucleic acid consisting of naturally occurring ribo- and/or deoxyribonucleotides, but also includes base pairing between mRNA and nucleic acids of the invention that include non-natural nucleotides.

siRNA Molecules

Short interfering RNAs (siRNAs) induce the sequence-specific suppression or silencing (i.e., reducing expression which may be to the extent of partial or complete inhibition) genes by the process of RNAi. Thus, siRNA is the intermediate effector molecule of the RNAi process. The nucleic acid molecules (polynucleotides) or constructs of the invention include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of the uORF in the extended, overlapping 5'-UTR AS mRNA species, and the other strand is identical or substantially identical to the first strand. The dsRNA molecules of the invention can be chemically synthesized, or can be transcribed in vitro from a DNA template, or in vivo from, e.g., shRNA. The dsRNA molecules can be designed using any method known in the art, for instance, by using the following protocol:

1. Using any method known in the art, compare the potential targets to the appropriate genome database (human, mouse, rat, etc.) and eliminate from consideration any target sequences with significant homology to other coding sequences. One such method for sequence homology searches is known as BLAST, which is available at the National Center for Biotechnology Information (NCBI) web site of the National Institutes of Health. Also available on the NCBI webs site is the HomoloGene database, which is a publicly available system for automated detection of homologs among the annotated genes of several completely sequenced eukaryotic genomes and is readily utilized by those of ordinary skill in the art.

2. Select one or more sequences that meet your criteria for evaluation. Further general information regarding the design and use of siRNA can be found in "The siRNA User Guide," available at the web site of the laboratory of Dr. Thomas Tuschl at Rockefeller University.

3. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Other computational tools that may be used to select siRNAs of the present invention include the Whitehead siRNA selection Web Server from the bioinformatics group at the Whitehead Institute for Biomedical Research in Cambridge, Mass., and other disclosed in Yuan, B. et al. ("siRNA Selection Server: an automated siRNA oligonucleotide prediction server", *Nucleic Acids Research*, 2004, Vol. 32, W130-W134, Web Server issue) and Bonetta L. ("RNAi: Silencing never sounded better", *Nature Methods*, Oct. 1, 2004(1):79-86), each of which are incorporated by reference herein in their entirety.

The polynucleotides of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanoparticles); Fattal et al., *J. Control Release* 53(1-3):137-43 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232(2):404-10 (1995) (describes nucleic acids linked to nanoparticles).

The nucleic acid molecules of the present invention can also be labeled using any method known in the art; for instance, the nucleic acid compositions can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^3$H, $^{32}$P, or other appropriate isotope.

Because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

There are a number of companies that will generate interfering RNAs for a specific gene. Thermo Electron Corporation has launched a custom synthesis service for synthetic short interfering RNA (siRNA). Each strand is composed of 18-20 RNA bases and two DNA bases overhang on the 3' terminus. Dharmacon, Inc. provides siRNA duplexes using the 2'-ACE RNA synthesis technology. Qiagen uses TOM-chemistry to offer siRNA with individual coupling yields of over 99.5%.

siRNA Delivery for Longer-Term Expression

Synthetic siRNAs can be delivered into cells by methods known in the art, including cationic liposome transfection and electroporation. However, these exogenous siRNA generally show short term persistence of the silencing effect (4 to 5 days in cultured cells), which may be beneficial in certain embodiments. To obtain longer term suppression of AS expression and to facilitate delivery under certain circumstances, one or more siRNA duplexes, e.g., AS ds siRNA, can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence(s) under the control of a T7 promoter also make functional siRNAs when co-transfected into the cells with a vector expressing T7 RNA polymerase (Jacque (2002), supra). A single construct may contain multiple sequences coding for siRNAs, such as multiple regions of the uORF in the extended, overlapping 5'-UTR AS mRNA species, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci. USA* 99(22):14236-40 (2002)). In adult mice, efficient delivery of siRNA can be accomplished by the "high-pressure" delivery technique, a rapid injection (within 5 seconds) of a large volume of siRNA containing solution into animal via the tail vein (Liu (1999), supra; McCaffrey (2002), supra; Lewis, *Nature Genetics* 32:107-108 (2002)). Nanoparticles, liposomes and other cationic lipid molecules can also be used to deliver siRNA into animals. A gel-based agarose/liposome/siRNA formulation is also available (Jiamg M. et al., *Oligonucleotides,* 2004, Winter, 14(4):239-48).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of any translational product encoded by that mRNA in the cell or organism. The RNA precursors are typically nucleic acid molecules that individually encode either one strand of a dsRNA or encode the entire nucleotide sequence of an RNA hairpin loop structure.

Antisense

An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the uORF in the extended, overlapping 5'-UTR AS mRNA species. Antisense nucleic acid sequences and delivery methods are well known in the art (Goodchild J., *Curr. Opin. Mol. Ther.*, Apr. 6, 2004 (2):120-128; Clawson G. A. et al., *Gene Ther.*, Sep. 11, 2004 (17):1331-1341), which are incorporated herein by reference in their entirety. The antisense nucleic acid can be complementary to an entire coding strand of a target sequence, or to only a portion thereof (for example, the upstream open-reading-frame (uORF) of the extended 5'-UTRs of AS mRNA, disclosed in Pendleton et al. (*J. Biol. Chem.*, 2002, 277: 25363-25369), which is incorporated herein by reference, or a portion of the uORF of the extended 5'-UTRs of AS mRNA. In another embodiment, the antisense nucleic acid molecule is antisense to a "noncoding region" of the coding strand of a nucleotide sequence within the uORF in the overlapping 5'-UTR AS mRNA species. For example, the antisense oligonucleotide can be complementary to a region representing positions −47 to −65 nt of the extended 5'-UTR AS mRNA, as shown in FIG. 1. An antisense oligonucleotide can be, for example, about 7, 10, 15, 20, 25, 30, 35, 40, 45, 50, 55, 60, 65, 70, 75, 80, or more nucleotides in length.

An antisense nucleic acid sequence can be designed such that it is complementary to the entire uORF of the extended, overlapping 5'-UTR AS mRNA species, but can also be an oligonucleotide that is antisense to only a portion of the uORF. For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., systemically or locally by direct injection at a tissue site), or generated in situ such that they hybridize with or bind to cellular mRNA and/or genomic DNA encoding the uORF of the extended, overlapping 5'-UTR AS mRNA species to thereby inhibit expression of the uORF, which results in increased expression of the downstream ORF encoding AS. Alternatively, antisense nucleic acid molecules can be modified to target selected cells (such as endothelial cells and/or vascular endothelial cells) and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense oligonucleotide of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.,* 215:327-330 (1987)).

uORF expression can be inhibited by targeting nucleotide sequences complementary to the regulatory region of the uORF to form triple helical structures that prevent expression of the uORF in target cells. See generally, Helene, C. Anti-cancer Drug Des. 6:569-84 (1991); Helene, C. *Ann. N.Y. Acad. Sci.* 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. Ribozymes and methods for their delivery are well known in the art (Hendry P. et al., *BMC Chem. Biol.*, Dec. 4, 2004(1):1; Grassi G. et al., *Curr. Pharm. Biotechnol.*, Aug. 5, 2004(4):369-386; Bagheri S. et al., *Curr. Mol. Med*, Aug. 4, 2004(5):489-506; Kashani-Sabet M., *Expert Opin. Biol. Ther.*, Nov. 4, 2004(11):1749-1755), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for the uORF of an extended, overlapping 5'-UTR AS mRNA species can include one or more sequences complementary to the nucleotide sequence of a uORF of an extended, overlapping 5'-UTR AS mRNA species disclosed herein (e.g., positions −47 to 65 nt, as shown in FIG. 1), and a sequence having known catalytic sequence responsible for mRNA cleavage (see U.S. Pat. No. 5,093,246 or Haselhoff and Gerlach *Nature* 334:585-591 (1988)). For example, a derivative of a Tetrahymena L-19 IVS RNA can be constructed in which the nucleotide sequence of the active site is complementary to the nucleotide sequence to be cleaved in the mRNA encoded by a uORF of an extended, overlapping 5'-UTR AS mRNA species (see, e.g., Cech et al. U.S. Pat. No. 4,987,071; and Cech et al. U.S. Pat. No. 5,116,742). Alternatively, mRNA encoded by a uORF of an extended, overlapping 5'-UTR AS mRNA species can be used to select a catalytic RNA having a specific ribonuclease activity from a pool of RNA molecules (see, e.g., Bartel, D. and Szostak, J. W. *Science* 261:1411-1418 (1993)).

Nucleic Acid Targets

The nucleic acid targets of the antisense, RNAi, and ribozymes as described herein may be any uORF of an extended, overlapping 5'-UTR AS mRNA species, or a portion thereof. In some embodiments, the nucleic acid target is an mRNA of a uORF of an extended, overlapping 5'-UTR AS mRNA species, or a portion thereof.

The mRNA sequence of the uORF of the extended, overlapping 5'-UTR AS mRNA species can be any ortholog of the uORF, such as sequences substantially identical to human, mouse, rat, or bovine, or a portion of any of the foregoing, including but not limited to GenBank Accession Nos. NM_054012 (human), NM_0074494 (mouse), and BC063146 (rat). In some embodiments, the mRNA sequence of the uORF can be the bovine sequence disclosed in Pendleton et al. (*J. Biol. Chem.*, 2002, 277:25363-25369), which is incorporated herein by reference.

The term "ortholog" as used herein refers to a sequence which is substantially identical to a reference sequence. The term "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, at least 60%, at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* 48:444-453 (1970)) algorithm, which has been incorporated into the GAP program in the GCG software package (available at the official Accelrys web site), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at the official Accelrys web site), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other orthologs, e.g., family members or related sequences. Such searches can be performed using the NBLAST and XBLAST programs (version 2.0) of Altschul, et al. *J. Mol. Biol.* 215:403-10 (1990). BLAST nucleotide searches can be performed with the NBLAST program, score=100, word length=12, to obtain nucleotide sequences homologous to known uORFs of extended, overlapping 5'-UTR AS mRNA species of the invention. BLAST protein searches can be performed with the XBLAST program, score=50, word length=3, to obtain amino acid sequences homologous to known polypeptide products of uORFs of extended, overlapping 5'-UTR AS mRNA species. To obtain gapped alignments for comparison purposes, Gapped BLAST can be utilized as described in Altschul et al., *Nucleic Acids Res.* 25:3389-3402 (1997). When utilizing BLAST and Gapped BLAST programs, the default parameters of the respective programs (e.g., XBLAST and NBLAST) can be used (see the National Center for Biotechnology Information web site of the National Institutes of Health).

Orthologs can also be identified using any other routine method known in the art, such as screening a cDNA library, e.g., a human cDNA library, using a probe designed to identify sequences which are substantially identical to a reference sequence.

Pharmaceutical Compositions and Methods of Administration

The polynucleotides of the subject invention (e.g., siRNA molecules, antisense molecules, and ribozymes) can be incorporated into pharmaceutical compositions. Such compositions typically include the polynucleotide and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pennsylvania, Mack Publishing Company, 19$^{th}$ ed., 1995) describes formulations which can be used in connection with the subject invention.

A pharmaceutical composition is formulated to be compatible with its intended route of administration. Examples of routes of administration include parenteral, e.g., intravenous, intradermal, subcutaneous, oral (e.g., inhalation), topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polynucleotide of the invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the polynucleotides can be delivered -in the form of an aerosol spray from a pressurized container or dispenser which contains a suitable propellant, e.g., a gas such as carbon dioxide, or a nebulizer. Such inhalation methods and inhalant formulations include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

The polynucleotides can also be administered by transfection or infection using methods known in the art, including but not limited to the methods described in McCaffrey et al., *Nature* 418(6893):38-39 (2002) (hydrodynamic transfection); Xia et al., *Nature Biotechnol.* 20(10):1006-10 (2002)

(viral-mediated delivery); or Putnam, *Am. J. Health Syst. Pharm.* 53(2):151-160 (1996), erratum at *Am. J. Health Syst. Pharm.* 53(3):325 (1996).

The polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2):205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the polynucleotides are prepared with carriers that will protect the polynucleotide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811. A strategy for the compaction of short oligonucleotides into well-defined condensates may also be used to deliver the polynucleotides of the subject invention (Sarkar T. et al., *Nucleic Acids Research*, 2005, 33(1):143-151), which is incorporated herein by reference in its entirety.

In particular, suitable techniques for cellular administration of the polynucleotides of the invention both in vitro and in vivo are disclosed in the following articles:

General Reviews:
Borkhardt, A. *Cancer Cell*, 2002, 2:167-8; Hannon, G. J. *Nature*, 2002, 418:244-51; McManus, M. T. and Sharp, P. A. *Nat Rev Genet.*, 2002, 3:737-47; Scherr, M. et al. *Curr Med. Chem.*, 2003, 10:245-56; Shuey, D. J. et al. *Drug Discov Today*, 2002, 7:1040-6.

Systemic Delivery Using Liposomes:
Lewis, D. L. et al. *Nat Genet.*, 2002, 32:107-8; Paul, C. P. et al. *Nat Biotechnol.*, 2002, 20:505-8; Song, E. et al. *Nat Med.*, 2003, 9:347-51; Sorensen, D. R. et al. *J Mol Biol.*, 2003, 327:761-6.

Virus Mediated Transfer:
Abbas-Terki, T. et al. *Hum Gene Ther.*, 2002, 13:2197-201; Barton, G. M. and Medzhitov, R. *Proc Natl Acad Sci USA*, 2002, 99:14943-5; Devroe, E. and Silver, P. A. *BMC Biotechnol.*, 2002, 2:15; Lori, F. et al. *Am J Pharmacogenomics*, 2002, 2:245-52; Matta, H. et al. *Cancer Biol Ther.*, 2003, 2:206-10; Qin, X. F. et al. *Proc Natl Acad Sci USA*, 2003, 100:183-8; Scherr, M. et al. *Cell Cycle*, 2003, 2:251-7; Shen, C. et al. *FEBS Lett.*, 2003, 539:111-4.

Peptide Delivery:
Morris, M. C. et al. *Curr Opin Biotechnol.*, 2000, 11:461-6; Simeoni, F. et al. *Nucleic Acids Res.*, 2003, 31:2717-24.

Other technologies that may be suitable for delivery of polynucleotides of the invention such as interfering RNA to the target cells are based on nanoparticles or nanocapsules such as those described in U.S. Pat. Nos. 6,649,192B and 5,843,509B. Recent technologies that may be employed for selecting, delivering, and monitoring interfering RNA molecules include Raab, R. M. and Stephanopoulos, G. *Biotechnol. Bioeng*, 2004, 88:121-132; Huppi, K. et al. *Mol. Cell*, 2005, 17: 1-10; Spagnou, S. et al. *Biochemistry*, 2004, 43:13348-13356; Muratovska, A. and Eccles, M. R. *FEBS Lett.*, 2004, 558:63-68; Kumar, R. et al. *Genome Res.*, 2003, 13:2333-2340; Chen, A. A. et al. *Nucleic Acids Res.*, 2005, 33:e190; Dykxhoorn, D. M. et al. *Gene Ther.*, 2006, epub ahead of print; Rodriguez-Lebron, E. and Paulson, H. L. *Gene Ther.*, 2005, epub ahead of print; Pai, S. I. et al. *Gene Ther.*, 2005, epub ahead of print; Raoul, C. et al. *Gene Ther.*, 2005, epub ahead of print; Manfredsson, F. P. et al. *Gene Ther.*, 2005, epub ahead of print; Downward, J. *BMJ*, 2004, 328: 1245-1248.

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture assays. A dose can be formulated in animal models to achieve a circulating plasma concentration range that includes the IC50 (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

The compositions of the invention can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a polynucleotide can include a single treatment or can include a series of treatments.

The polynucleotides of the invention (e.g., interfering RNA, antisense oligonucleotide, or ribozyme) can be introduced (administered) into cells (such as mammalian cells) in vitro or in vivo using known techniques, as those described herein, to suppress gene expression. Similarly, genetic constructs (e.g., transcription vectors) containing DNA of the invention may be introduced into cells in vitro or in vivo using known techniques, as described herein, for transient or stable expression of RNA, to suppress gene expression. When administered to the cells in vivo, the polynucleotides of the invention can be administered to a subject systemically (e.g., intravenously), for example, or administered locally at the site of the cells (such as at the heart or vascular endothelium).

The cells in which the polynucleotides of the invention are introduced (administered) may be any cell containing the uORF of an extended, overlapping 5'-UTR AS mRNA species. The cells can be primary cells, cultured cells, cells of cell lines, etc. In one embodiment, the cells are endothelial cells. In another embodiment, the cells are vascular endothelial cells. In another embodiment, the cells are heart cells. In another embodiment, the cells are aortic endothelial cells.

Mammalian species which benefit from the disclosed methods include, but are not limited to, primates, such as humans, apes, chimpanzees, orangutans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein, the terms "subject", "patient", and "individual" are used interchangeably and intended to include such human and non-human mammalian species. Likewise, in vitro methods of the present invention can be carried out on cells of such mammalian species. Host cells comprising exogenous polynucleotides of the invention may be administered to the subject, and may, for example, be autogenic (use of one's own cells), allogenic (from one person to another), or transgenic or xenogenic (from one mammalian species to another mammalian species), relative to the subject.

The polynucleotides of the invention can be inserted into genetic constructs, e.g., viral vectors, retroviral vectors, expression cassettes, or plasmid viral vectors, e.g., using methods known in the art, including but not limited to those described in Xia et al., (2002), supra. Genetic constructs can be delivered to a subject by, for example, inhalation, orally, intravenous injection, local administration (see U.S. Pat. No. 5,328,470) or by stereotactic injection (see, e.g., Chen et al., *Proc. Natl. Acad Sci. USA* 91:3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotides of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brumnmelkamp et al., *Science* 296:550-553 (2002); Lee et al., (2002), supra; Miyagishi and Taira, *Nature Biotechnol.* 20:497-500 (2002); Paddison et al. (2002), supra; Paul (2002), supra; Sui (2002) supra; Yu et al. (2002), supra.

SiRNAs of the invention may be fused to other nucleotide molecules, or to polypeptides, in order to direct their delivery or to accomplish other functions. Thus, for example, fusion proteins comprising a siRNA oligonucleotide that is capable of specifically interfering with expression of the uORF of an extended 5'-UTR form of AS may comprise affinity tag polypeptide sequences, which refers to polypeptides or peptides that facilitate detection and isolation of the such polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (*Bio/Technology* 6:1204, 1988), or the XPRESS epitope tag (INVITROGEN, Carlsbad, Calif.). The affinity sequence may be a hexa-histidine tag as supplied, for example, by a pBAD/His (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

The present invention also relates to vectors and to constructs that include or encode polynucleotides of the present invention (e.g., siRNA), and in particular to "recombinant nucleic acid constructs" that include any nucleic acid such as a DNA polynucleotide segment that may be transcribed to yield extended 5'-UTR AS uORF-specific siRNA polynucleotides according to the invention as provided above; to host cells which are genetically engineered with vectors and/or constructs of the invention and to the production of siRNA polynucleotides, polypeptides, and/or fusion proteins of the invention, or fragments or variants thereof, by recombinant techniques. siRNA sequences disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements). These DNA polynucleotides are therefore encompassed within the contemplated invention, for example, to be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al., *Nat. Biotechnol.* 20:497-500 (2002); Lee et al., *Nat. Biotechnol.* 20:500-505 (2002); Paul et al., *Nat. Biotechnol.* 20:505-508 (2002); Grabarek et al., *BioTechniques* 34:73544 (2003); see also Sui et al., *Proc. Natl. Acad. Sci. USA* 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for an extended 5'-UTR AS uORF sequence may be transcribed under the control of a single promoter such that the siRNA polynucleotide forms a hairpin molecule (Paul et al., supra). In such an instance, the complementary strands of the siRNA specific sequences are separated by a spacer that comprises at least four nucleotides, but may comprise at least 5, 6, 7, 8, 9, 10, 11, 12, 14, 16, or 18 or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., *Science* 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

Polynucleotides of the invention can be expressed in mammalian cells, yeast, bacteria, or other cells under the control of appropriate promoters, providing ready systems for evaluation of siRNA polynucleotides that are capable of interfering with polypeptide expression as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor, N.Y., (2001).

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control sequence (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above.). A tissue-specific promoter allows preferential expression of the polynucleotide in a given target tissue, thereby avoiding expression in other tissues. For example, to express genes specifically in the heart, a number of cardiac-specific regulatory elements can be used. An example of a cardiac-specific promoter is the ventricular form of MLC-2v promoter (see, Zhu et al., *Mol. Cell Biol.* 13:4432-4444, 1993; Navankasattusas et al., *Mol. Cell Biol.* 12:1469-1479, 1992) or a variant thereof such as a 281 bp fragment of the native MLC-2v promoter (nucleotides −264 to +17, Genebank Accession No. U26708). Examples of other cardiac-specific promoters include alpha myosin heavy chain (Minamino et al., *Circ. Res.* 88:587-592, 2001) and myosin light chain-2 (Franz et al., *Circ. Res.* 73:629-638, 1993). Endothelial cell gene promoters include endoglin and ICAM-2. See Velasco et al., *Gene Ther.* 8:897-904, 2001. Liver-specific promoters include the human phenylalanine hydroxylase (PAH) gene promoters (Bristeau et al., *Gene* 274:283-291, 2001), hB1F (Zhang et al., *Gene* 273:239-249, 2001), and the human C-reactive protein (CRP) gene promoter (Ruther et al., *Oncogene* 8:87-93, 1993). Promoters that are kidney-specific include CLCN5 (Tanaka et al., *Genomics* 58:281-292, 1999), renin (Sinn et al., *Physical Genomics* 3:25-31, 2000), androgen-regulated protein, sodium-phosphate cotransporter, renal cytochrome P-450, parathyroid hormone receptor and kidney-specific cadherin. See *Am. J. Physiol. Renal Physiol.* 279:F383-392, 2000. An example of a pancreas-specific promoter is the pancreas duodenum homeobox 1 (PDX-1) promoter (Samara et al., *Mol. Cell Biol.* 22:4702-4713, 2002). A number of brain-specific promoters may be useful in the invention and include the thy-1 antigen and gamma-enolase promoters (Vibert et al., *Eur. J. Biochem.* 181:33-39, 1989), the glial-specific glial fibrillary acidic protein (GFAP) gene promoter (Cortez et al., *J. Neurosci. Res.* 59:39-46, 2000), and the human FGF1 gene promoter (Chiu et al., *Oncogene* 19:6229-6239, 2000). The GATA family of transcription factors have promoters directing neuronal and thymocyte-specific expression (see Asnagli et al., *J. Immunol.* 168:4268-4271, 2002).

In another aspect, the present invention relates to host cells containing the above described recombinant constructs. Host cells are genetically engineered/modified (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as E. coli, Streptomyces, Salmonella typhimurium; fungal cells, such as yeast; insect cells, such as Drosophila S2 and Spodoptera Sf9; animal cells, such as CHO, COS or 293 cells; adenoviruses; plant cells, or any suitable cell already adapted to in vitro propagation or so established de novo.

Various mammalian cell culture systems can also be employed to produce polynucleotides of the invention from recombinant nucleic acid constructs of the present invention. The invention is therefore directed in part to a method of producing a polynucleotide, such as an siRNA, by culturing a host cell comprising a recombinant nucleic acid construct that comprises at least one promoter operably linked to a polynucleotide of the invention that is specific for the uORF of an extended 5'-UTR AS. In certain embodiments, the promoter may be a regulated promoter as provided herein, for example a tetracycline-repressible promoter. In certain embodiments the recombinant expression construct is a recombinant viral expression construct as provided herein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986 Basic Methods in Molecular Biology), or other suitable technique.

The expressed polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

As used herein, the terms "administer", "introduce", "apply", "treat", "transplant", "implant", "deliver", and grammatical variations thereof, are used interchangeably to provide polynucleotides or vectors of the subject invention to target cells in vitro (e.g., ex vivo) or in vivo, or provide genetically modified (engineered) cells of the subject invention to a subject.

As used herein, the term "co-administration" and variations thereof refers to the administration of two or more agents simultaneously (in one or more preparations), or consecutively. For example, one or more types of genetically modified cells of the invention can be co-administered with other agents.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

The publication Pendleton L. C. et al., J. Biol. Chem., 2005, 280(25):24252-24260, is incorporated herein by reference in its entirety.

Materials and Methods

Cell Culture. Bovine aortic endothelial cells (BAEC) were cultured in Dulbecco's modified Eagle's medium (1 g/L glucose, MEDIATECH) supplemented with 10% fetal bovine serum (HYCLONE Laboratories), 100 units/ml penicillin and 100 µg/ml streptomycin (MEIATECH) at 37° C. and 5% $CO_2$.

Preparation of AS Constructs. Full-length AS cDNA was constructed to contain either the 92 nt or the 43 nt 5'-UTR, shown in FIG. 1, and subcloned into the vector pPDM-2 (EPICENTRE Technologies) as previously described (Pendleton, L. C. et al. J. Biol. Chem., 2002, 277:25363-25369). Mutations were created in the constructs by multiple rounds of PCR amplification using Pfu Turbo DNA Polymerase (STRATAGENE) in a reaction containing 1× Pfu reaction buffer (10 mM KCl, 10 mM $(NH_4)SO_4$, 20 mM Tris-HCl, pH 8.75, 2 mM $MgSO_4$, 0.1% Triton X-100, and 0.1 mg/ml BSA), 200 µM each dNTP, 50 pmol of each primer, 10 ng digested plasmid template and 2.5 units of Pfu Polymerase. PCR reactions consisted of 30 cycles at 95° C. for 1 minute, 50° C. for 1 minute and 72° C. for 2 minutes. In the 92 nt construct, single base insertions of A residues were made at positions −1 (Ins 1) and −39 (Ins 2) relative to the AS AUG (FIG. 1). These mutations placed the uAUG and the AS AUG in the same frame. A left primer containing the insertion in the center, either ASL-11MFS (5' CAC CCG TCA CGA ATG TCC GGC AA 3') (SEQ ID NO:2) for Ins 1 or ASL-48MFS (5' AAC CCG CCC TAG CTC CGC CGA CT 3') (SEQ ID NO:3) for Ins 2 were paired up with ASR429 (5' GAG CGA TGA CCT TGA TCT GT 3') (SEQ ID NO:4) to amplify a section of the 92 nt 5'-UTR construct (inserted bases are underlined). This PCR product was then used as a right primer and paired with ASL-92T7 (Pendleton, L. C. et al. *J. Biol. Chem.*, 2002, 277:25363-25369) to produce a fragment with the mutation in the center and the restriction sites Bam HI and Nar I on either end for cloning back into the pPDM-2 vector in place of the wild type fragment. Because the yield of product in the second round of PCR was typically very low, a third round of PCR was performed using the second round product as template, and using the primers ASL-92T7 and ASR429 to re-amplify the target fragment before restriction digestion and subcloning.

Mutations were also made in the 92 and 43 nt constructs to convert two uORF stop codons to lysine residues thereby extending the product encoded by the uORF from 4.5 kDa to 21 kDa. The two UGA codons at positions +70 and +153 relative to, but out-of-frame with, the AS AUG were changed to AAA codons. Primers ASL59MStop (5' TCC TCG TGT GGC AAA AGG AGC AAG GCT 3') (SEQ ID NO:5) and ASR168MStop (5' GGC CCC AAGCTTTTG CGC CTT CTT CC 3') (SEQ ID NO:6) were combined to amplify a fragment of AS that contained both of the stop mutations (mutated bases are underlined). This fragment was then used as a right primer in the same strategy used for the insertion mutations, followed by a third round PCR reaction using ASL-92T7 and ASR169MStop to enrich for the target fragment. Bam HI (incorporated in ASL-92T7) and Hind III (site marked by dashed underline in ASR168MStop primer) restriction enzymes were used to clone the mutated fragment into the AS 92 nt 5'-UTR plasmid. All constructs were verified by sequencing.

In Vitro Transcription/Translation. AS constructs were digested with Eco RV at a site past the 3'-end to prevent run-on transcription. Template DNAs were transcribed using T7 RNA polymerase with the addition of Ribo m$^7$G Cap Analog (PROMEGA) following the manufacturer's protocol recommended for m$^7$G cap incorporation. Transcribed RNA was DNase treated and purified using minispin G50 Sephadex (CPG) columns. The Flexi Rabbit Reticulocyte Lysate System (PROMEGA) was used for the translation reaction following the manufacturer's protocol, with the addition of 10 _Ci [$^{35}$S]-L-methionine (AMERSHAM PHARMACIA BIOTECH) and 500 ng capped RNA. KCl conditions were optimized to 40 mM. Translated proteins were separated by sodium dodecyl sulfate polyacrylamide gel electrophoresis (SDS-PAGE) on 10% Tris-HCl Ready Gels (BIO-RAD Laboratories). Gels were fixed in 50% methanol and 10% acetic acid for 30 minutes, followed by a second solution of 7% methanol, 7% acetic acid, 1% glycerol for 5 minutes, dried on a gel dryer for 2 hours, and exposed to film. Band intensities were quantitated using a Chemilmager 4400 (ALPHA INNOTECH).

Preparation of Luciferase Constructs. Luciferase reporter constructs were designed to include different sizes of the AS 5'-UTR cloned directly after the simian virus 40 promoter and before the start codon of the luciferase gene. One set of clones contained truncated forms of the 5'-UTR, the sequence spanning the region from either the −66 or −92 nt positions to the uAUG at position −57 relative to the AS AUG. Left primers LucASL-66 (5' AGA AAG CTT ACCCGGGATGGA AGA CGC CAA AAA CAT 3') (SEQ ID NO:7) and LucASL-92 (5' AGA AAG CTT CCCTGCCCCCCGGCCCCGAGCTT ATAACCCGGGATG GAA GAC GCC AAA AAC ATA 3') (SEQ ID NO:8) both contain a Hind III site on the 5'-end, AS 5'-UTR sequence (underlined), and the first 17 bases of the luciferase gene after the AUG on the 3'-end. These primers were combined with RTLuc1R (5' CAC CTC GAT ATG TGC ATC TG 3') (SEQ ID NO:9) to amplify a small fragment of the luciferase gene which was then cloned into pGL3Control vector (PROMEGA), using Hind III and Nar I, so that the various AS 5'-UTR segments replaced the luciferase 5'-UTR.

Another luciferase construct, described previously (Pendleton, L. C. et al. *J. Biol. Chem.*, 2002, 277:25363-25369), was designed to contain the entire 92 nt of the AS 5'-UTR in front of the luciferase gene. This construct was mutated, using the three round PCR method described in the preparation of AS constructs, to contain a single base insertion at position −39 (Ins 2 in FIG. 1). Similar to the AS Ins 2 mutation, this mutation put the AS uAUG and the luciferase AUG in frame. Constructs were verified by sequencing.

Luciferase Assays. BAEC to be used for transfections were plated at $6 \times 10^4$ cells per well in a 24 well plate, twenty-four hours prior to transfection. Control plasmids (PROMEGA) included pGL3Control as a positive control, pGL3Basic as a promoterless negative control, and pRL-TK, a Renilla expression vector, as an internal transfection control. Control, Basic, and experimental plasmids (200 ng each), and pRL-TK (50 ng) were transiently transfected into BAEC using Transit-LT1 (MIRUS) in serum free media. After 4.5 hours, media was replaced with media containing 10% serum and cells were cultured for 48 hours. Lysates generated with Passive lysis buffer (PROMEGA) were assayed for luciferase and Renilla activity using Promega's Dual-Luciferase Reporter Assay System according to the manufacturer's recommendations. Luciferase and Renilla activity were measured as relative light units using a luminometer (TURNER DESIGNS). Experiments were carried out three times in triplicate. Luciferase expression was normalized to Renilla activity. Passive lysis buffer lysates were separated by SDS-PAGE on 10% Tris-HCl Ready Gels (BIO-RAD Laboratories) and blotted onto Immobilon-P polyvinylidene difluoride membranes (MILLIPORE). Western blotting was performed as previously described (Pendleton, L. C. et al. *J. Biol. Chem.*, 2002, 277:25363-25369). The primary antibody used was anti-luciferase (CORTEX BIOCHEM) at a 1:500 dilution. The secondary antibody used was peroxidase-conjugated goat anti-mouse IgG (JACKSON IMMUNORESEARCH LABS) at a 1:50,000 dilution. Blots were visualized by chemiluminescence using ECL reagent (GE HEALTHCARE) and exposed to film. Band intensities were quantitated using a Chemilmager 4400.

Preparation and Transfection of Argininosuccinate Synthase Upstream Open Reading Frame (ASuORF) Constructs. For transfection studies with the ASuORF, AS sequences covering the region from −92 to +70 and −43 to +70 relative to the AS AUG were cloned into pcDNA 3.1/V5-His B expression vector (INVITROGEN). Primers ASL-92BamHI (5' AGT CGG ATC CCC CTG CCC CCC GGC CCC GAG 3') (SEQ ID NO:10) and ASL-43BamHI (5' AGT CGG ATC CGC CCT GCT CCG CCG ACT GCT 3') (SEQ ID NO:11) combined with ASR73EcoRI (5' TGC AGA ATT CCC GCC ACA CGA GGA TGC AGG AGG 3') (SEQ ID NO:12) were used to amplify this region. Both primers contained restriction sites designed for cloning into the pcDNA vector and the right primer also mutated out the uORF stop codon at position 72, thereby linking the uORF to the V5 and His tags in the vector (ASuORF). For a negative control, this same region was amplified from a previously described construct in which the uAUG at position −59 was mutated to AAG (Pendleton, L. C. et al. *J. Biol. Chem.*, 2002, 277:25363-25369), thereby rendering the AS uORF non-functional (AAGNegC). BAEC to be used for transfections were plated at $2 \times 10^5$ cells per well in a 12-well plate twenty-four hours prior to transfection.

Experimental plasmids, ASuORF, AAGNegC, and the empty vector (0.8, 1.6, and 2.4 μg each) were transiently transfected into BAEC using Lipofectamine 2000 (INVITROGEN) in serum free Opti-MEM I (INVITROGEN). After 4 hours, media was replaced with Dulbecco's modified Eagle's medium containing 10$ serum and cells were cultured for 24 hours.

Additional constructs of the AS uORF were used to investigate the effects of sequence and/or length of the uORF relative to its ability to suppress AS expression. Mutations were made that deleted a residue at position −53 and inserted a residue at position +69 relative to the AS AUG to cause a frameshift in the peptide sequence of the AS uORF. Primers uORFfsleft (5'-ACCCCGGGATGCGC/CCGAAACCCG-3') (SEQ ID NO:13) and uORFfsright (5'-CAGAATTC-CCGC<u>C</u>CACACGAGGAT-3') (SEQ ID NO:14) were used to amplify by PCR the mutated fragment. The deletion and insertion sites are marked by a slash and an underline, respectively. A SmaI site in the left primer and EcoRI site in the right primer were used to clone the fragment into the ASuORF expression vector in place of the wild-type fragment. Similarly, mutations were introduced to move the AS uORF start codon downstream to position +1 relative to the AS start codon and to move the AS uORF stop codon upstream to position +11. Using primers uORFdnsAUG (5'-GCTGGT-CACCCGTCACGA<u>AT</u>GCCGGCAAAGGCTC-3') (SEQ ID NO: 15) and uORFupsStop (5'-GCTGGTCACCCGTCAC-GATGTCCGGCA<u>TA</u>GGCTCCGTGG-3') (SEQ ID NO:16) combined with ASR73EcoRI, the mutated fragments were amplified and cloned using the BstEII site in the forward primers and the EcoRI site in the reverse primer. The dnsAUG (downstream AUG) mutation fragment was cloned into the AAGNegC construct that was lacking the normal uAUG. The upsStop (upstream stop) fragment was cloned into the wild-type ASuORF construct. BAEC were transfected as described in the previous section.

AS uORF constructs were developed that allowed the protein product to be easily resolved and visualized by SDS-PAGE analysis. Green fluorescent protein (GFP) was amplified from the pGreen Lantern plasmid (Invitrogen) using the primers GFPleft (5'-AGTCGGCGGCCGCCGCCACAT-GAGCAAGGGC-3') (SEQ ID NO:17) and GFPright (5'-CTAGAGCGGCCGCACTTGTACAGC-3') (SEQ ID NO:18). The left primer contained a NotI site for cloning and deleted a base between the NotI site and the AUG to place GFP and the AS uORF in-frame. The right primer also contained a NotI site for cloning and deleted a base at the GFP stop codon to mutate out the stop codon and also to put GFP in-frame with the V5 and His tags. GFP was cloned into the ASuORF construct at the NotI site between the uORF and the V5/His tags. GFP was also cloned into the uORFfs (frameshift) construct in the same manner. Constructs were verified by sequencing, and BAEC were transfected as described in the previous section.

RNA Duplex Preparation and Transfection. AMBION's SILENCER siRNA Construction Kit was used to synthesize 21-nucleotide RNA duplexes. Target sequences were chosen following the guidelines described by Tuschl et al. (Elbashir et al., *EMBO J.*, 2001, 20:6877-6888). The siRNA sequence specific to AS corresponded to bp −65 to −47 (FIG. 1) relative to the first nucleotide of the start codon: 5' CCC GGG AUG CGC GCC GAA Att 3' (SEQ ID NO: 1). A control siRNA was designed by scrambling the bases of the AS siRNA: 5'ACA GAG GGA CUC GCC CGC GUU 3' (SEQ ID NO:19). Both sequences were subjected to BLAST search to rule out homology to mRNAs encoding known proteins. Twenty-four hours prior to transfection, BAEC were seeded in a 24-well plate at $1\times10^5$ cells per well. Transfection of siRNA was carried out with TransIT-TKO (MIRUS) as described by the manufacturer. For each well, 10-25 nM siRNA duplex was combined with 3 μl liposome in serum free Dulbecco's modified Eagle's medium and applied to cells at 80-90% confluency. Cells were assayed 24 hr after transfection.

Cell Lysate Preparation and Immunoblotting. BAEC were trypsinized and then washed in ice cold phosphate-buffered saline (PBS) and resuspended in RIPA buffer (1% Nonidet P-40, 0.5% sodium deoxycholate, 0.1% SDS, 1× protease inhibitors (CALBIOCHEM) in PBS) by vigorous pipetting followed by brief vortexing. The lysate was incubated on ice for 30 minutes and the protein concentration was determined by BCA assay (PIERCE). Equal amounts (5-10 μg) of protein were resolved on 4-15% Tris-HCL Ready Gels and blotted onto Immobilon-P polyvinylidiene difluoride membranes. Western blotting was performed as previously described. Membranes were incubated with primary antibody, 1:2500 anti-AS (BD TRANSDUCTION LABS), 1:5000 anti-V5 (INVITROGEN), or 1:2000 anti-glyceraldehyde-3-phosphate dehydrogenase (NOVUS BIOLOGICALS). The secondary antibody used was peroxidase-conjugated goat anti-mouse or anti-rabbit IgG (JACKSON IMMUNORESEARCH LABS) at 1:50,000 dilution for all primary antibodies except β-actin, where the secondary antibody dilution was 1:75,000. Blots were visualized by chemiluminescence using ECL reagent and exposed to film.

RNA Isolation and Quantitative RT-PCR. Total RNA was isolated from BAEC by the method of Chomczynski and Sacchi (Chomczynski, P. and Sacchi, N., *Anal. Biochem.*, 1987, 162:156-159) using TriReagent (Molecular Research Center) according to the manufacturer's protocol. Pellet Paint Co-Precipitant (NOVAGEN) was added to help visualize the small RNA pellets. RNA was treated with DNase using the DNA-free kit (AMBION) and quantitated prior to reverse transcription with oligo (dT) primers using the Superscript First Strand cDNA synthesis kit (INVITROGEN) following the manufacturer's protocol. Real time quantitative PCR was performed as previously described using AS specific primer sets ASL228 and ASR278 for detecting all AS mRNA, and ASL-62 and ASR-12 for detecting the extended 5'-UTR forms of AS mRNA (Pendleton, L. C. et al. *J. Biol. Chem.*, 2002, 277:25363-25369). Results were normalized to β-Actin using primers βactin forward (5' GAG GCA TCC TGA CCC TCA AG 3') (SEQ ID NO:20) and β-actin reverse (5' TCC ATG TCG TCC CAG TTG GT 3') (SEQ ID NO:21).

Nitric Oxide Assay. Basal levels of nitrite were measured in the cell culture media twenty-four hours after transfection with siRNA as an indicator of cellular NO production using a fluorometric method (Misko, T. P. et al. *Anal. Biochem.*, 1993, 214:11-16). Twenty-four hours after transfection of the AS uORF overexpression constructs, BAEC were stimulated with 50 μM sodium orthovanadate and 0.5 μM A23187 calcium ionophore for two hours (Hellermann, G. R. et al. *Arterioscler. Thromb. Vasc. Biol.*, 2000, 20:2045-2050) and media was collected for the nitrite assay. Samples were read on a BMG FLUOstar Galaxy spectrofluorometer plate reader exciting at 360 nm and detecting emission at 405 nm. Cells were counted by trypan blue exclusion and data are presented as nitrite produced per $1\times10^6$ cells.

It should be understood that the examples and embodiments described herein are for illustrative purposes only and that various modifications or changes in light thereof will be

EXAMPLE 1

Figure 2A:
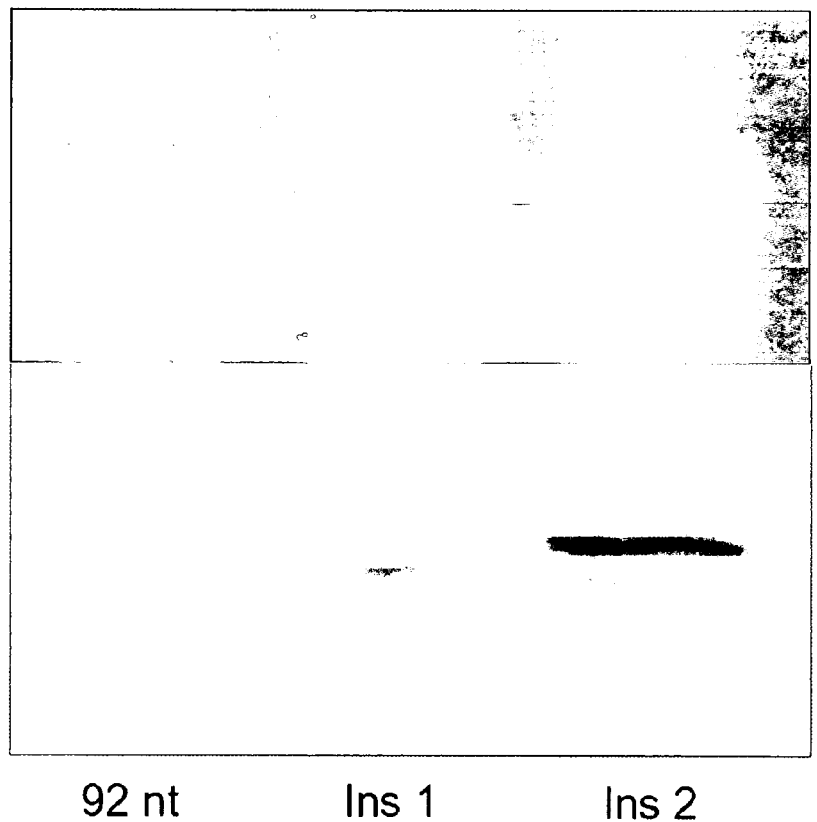
FIGS. 2A-2B show mutational analysis to determine the functionality of the uAUG of AS mRNA by in vitro transcription/translation. AS constructs containing the 92 nt 5'UTR (92 nt) and two single base insertion mutations (Ins 1 and Ins 2) that put the AS AUG and the uAUG in frame were transcribed and translated in vitro. Transcribed RNA was verified by agarose gel electrophoresis (FIG. 2A, top). Translated [35S]-L-methionine labeled proteins were separated by SDS PAGE, and gels were dried and exposed to film (FIG. 2A, bottom). The quantitation of the bands is shown in FIG. 2B. Expression levels are normalized to the 92 nt band.
Figure 2B:
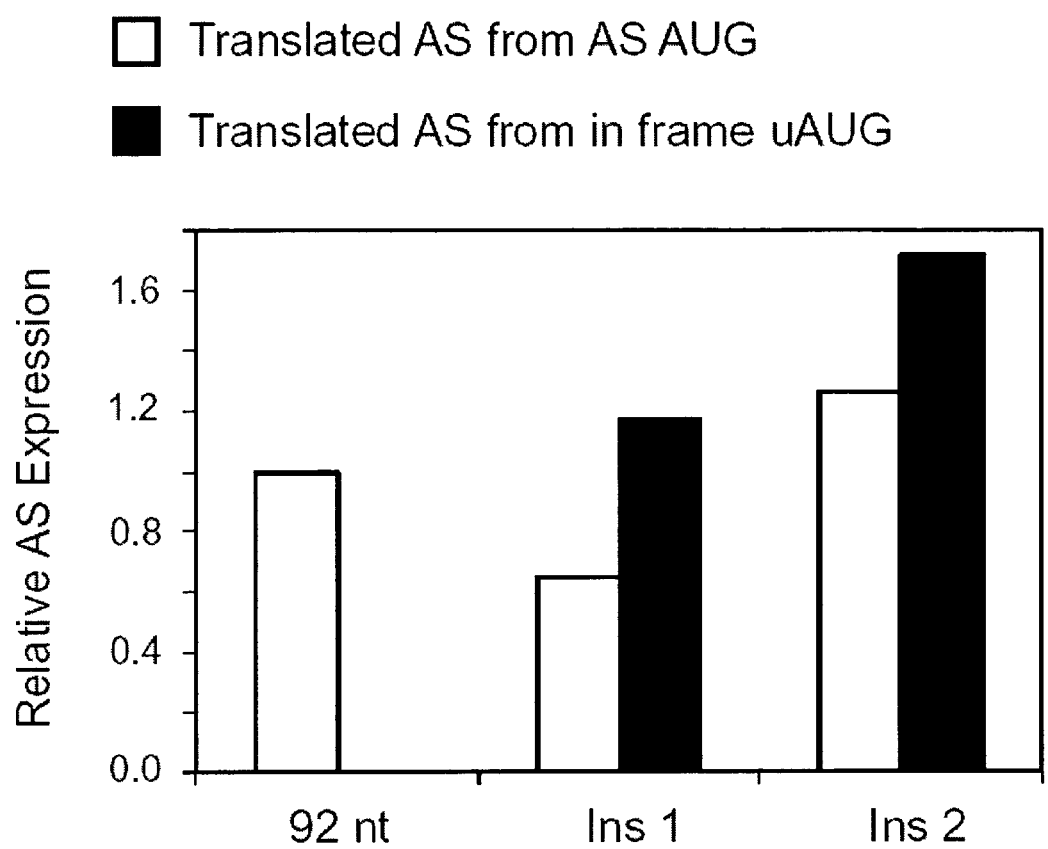

Functionality of the AS uAUG in an in vitro Transcription/Translation System Because the extended AS 5'-UTRs, containing an uAUG, were shown to act in cis to downregulate the translation of AS mRNA (Pendleton, L. C. et al. *J. Biol Chem.*, 2002, 277: 25363-25369), studies were carried out to determine whether the cis-effect was due to initiation at the uAUG and/or translation of the uORF. To examine the functionality of the uAUG in the extended 5'-UTR AS mRNAs, two different mutations were made in a full-length AS construct containing the 92 nt 5'-UTR. A single nucleotide was inserted between the uAUG and the downstream AS AUG, placing the uORF in-frame with the AS ORF so that initiation at either AUG would produce AS protein. One insertion was placed in close proximity to the AS AUG (Ins 1), while the other was placed more distal, 39 nt upstream from the AS AUG (Ins 2) as shown in FIG. 1. The two different nucleotide insertions were chosen such that secondary structure (folding pattern) of the RNA was predicted to be essentially the same for mutated and wild-type versions. Transcribed RNA from each construct was verified to be a single band by agarose gel electrophoresis and ethidium bromide staining (FIGS. 2A-2B). All constructs were transcribed and translated in vitro in the presence of L-[$^{35}$S]methionine. Translated products were separated on SDS-PAGE as shown in FIGS. 2A-2B. The wild-type AS 92 nt 5'-UTR construct yielded a single product of ~47 kDa, the expected size of AS (Dennis, J. A. et al. *Proc Natl Acad Sci USA*, 1989, 86:7947-7951). Both of the insertion mutant constructs yielded doublets of ~47 kDa and ~49 kDa, where the 49 kDa band represented the calculated size of the AS protein if translation was initiated using the uAUG. The amount of label observed in the ~47 kDa bands reflects not only the cis negative influence of the uORF as observed in the intact 92-nt extended AS mRNA, but also the relative efficiency of downstream initiation observed n the case of the two insertion mutations. In addition, the slight decrease in the Ins 1 ~47 kDa band may indicate the influence of an inserted nucleotide within the boundaries of the Kozak consensus sequence (Kozak, M., *J. Biol. Chem.*, 1991, 266:19867-19870) at the downstream AUG, diminishing the efficiency of translational initiation. Western blot analysis confirmed that both bands represented AS sequence (data not shown). For the Ins 1 mutation, quantitation of the two bands showed that initiation from the uAUG was 1.8 times greater than from the downstream AUG. For the Ins 2 mutation, the level of initiation from the uAUG was 1.4 times the level of the AS AUG. When the context of the uAUG was further altered by changing nucleotides −3 to A and +4 to G relative to the uAUG to better match a consensus Kozak sequence (Kozak, M. *J Biol Chem.*, 1991, 266:19867-19870), initiation of translation shifted almost entirely to the uAUG (data not shown). These results suggest that the cis-effects of the uAUG in the extended length 5'-UTR AS mRNAs resulted from its functional use, and that the low level of translation from the downstream AS AUG may result from leaky scanning (Kozak, M. *Gene*, 1999, 234:187-208) due to the moderately suboptimal context of the uAUG (Pendleton, L. C. et al. *J Biol Chem.*, 2002, 277: 25363-25369).

Figure 3A:
FIGS. 3A-3B show visualization of AS uORF expression in vitro by mutagenesis of uORF stop codons. AS constructs containing the 92 nt and 43 nt 5'-UTRs were mutated to extend the uORF from 4 to 21 kDa. Translated [$^{35}$S]-L-methionine labeled proteins were separated by SDS PAGE and gels were dried and exposed to film (FIG. 3A). The schematic in FIG. 3B shows the uORF stop codons, marked by X, that were mutated to lysine residues and the location of the new uORF stop codon.
Figure 3B:
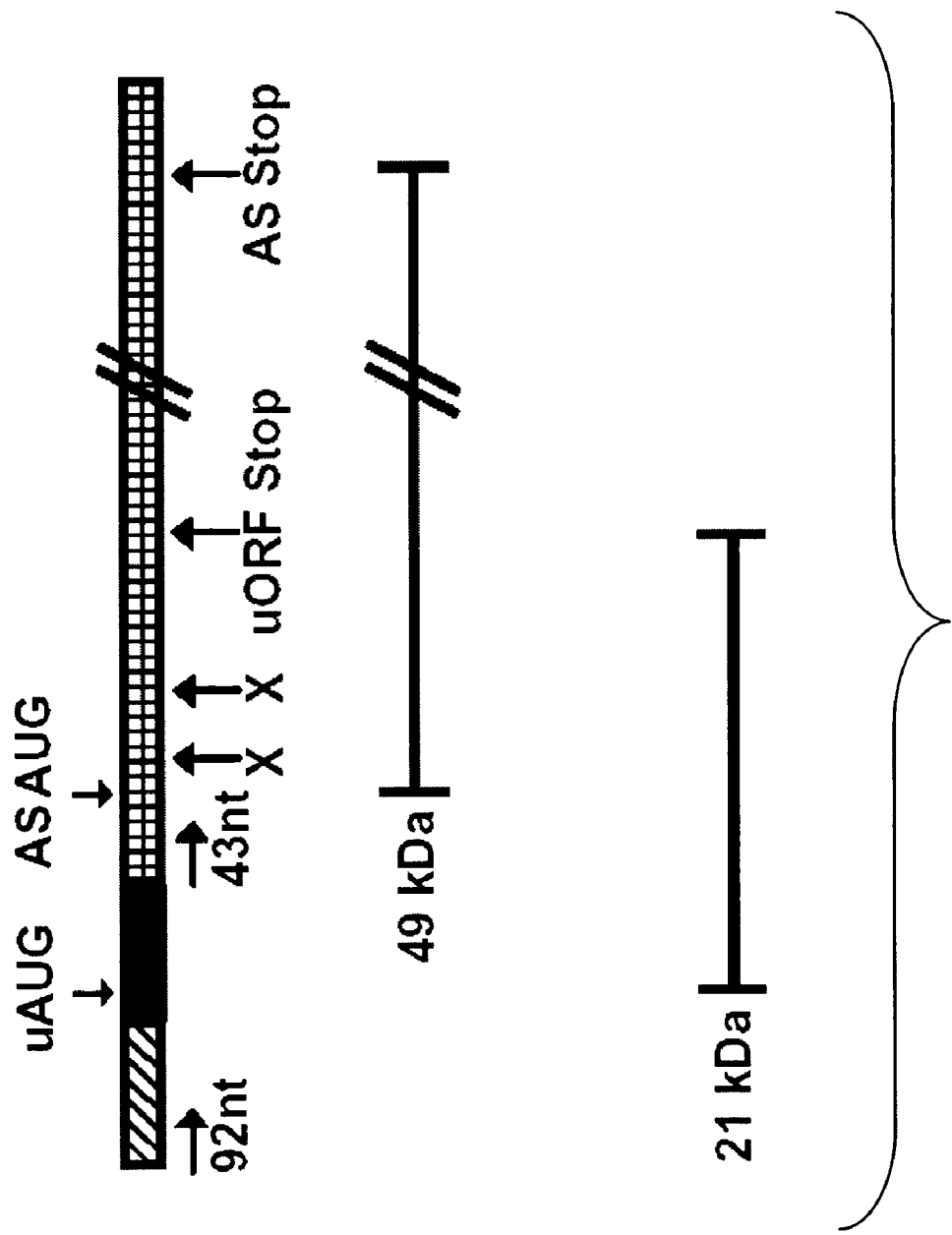

To demonstrate that the uORF was functional in its normal out-of-frame mode, two mutations were created in the full-length AS mRNA construct containing the 92 nt 5'-UTR. These mutations changed the first two stop codons in the uORF to lysine residues, thus extending the translation product of the out-of-frame uORF from an ~4 kDa to an ~21 kDa protein that could be easily visualized on SDS-polyacrylamide gel by [$^{35}$S]-L-methionine incorporation. To control for the effect of these mutations, which changed two leucines to glutamines in the downstream ORF encoding AS protein, the same mutations were introduced into the 43 nt 5'-UTR AS mRNA construct. All constructs were transcribed and translated in vitro in the presence of label, and the translated products were analyzed by SDS-PAGE analysis (FIGS. 3A-3B). Translation of the 43 nt 5'-UTR AS mRNA construct yielded a single band of the correct size (~47 kDa) for AS, showing that the mutations (two amino acid changes) did not affect translation. Translation of the 92 nt 5'-UTR AS mRNA construct, however, resulted in two L-[$^{35}$S]methionine labeled bands; an ~47 kDa and a second smaller protein product at ~21 kDa, demonstrating that the out-of-frame uORF is functional. The broad darkened region at about 30 kDa was considered to be unrelated to the in vitro translation of the extended 92-nt 5'-UTR AS mRNA species because it was most predominant in the translation of the 43-nt 5'-UTR AS mRNA. These results provide further evidence that ribosomes can translate the entire uORF rather than prevent the translation of the downstream ORF encoding AS by stalling at the uAUG (Morris, D. R. and A. P. Geballe *Mol Cell Biol.*, 2000, 20:8635-8642; Kozak, M. *J Biol Chem.*, 1991, 266: 19867-19870).

EXAMPLE 2

Figure 4A:
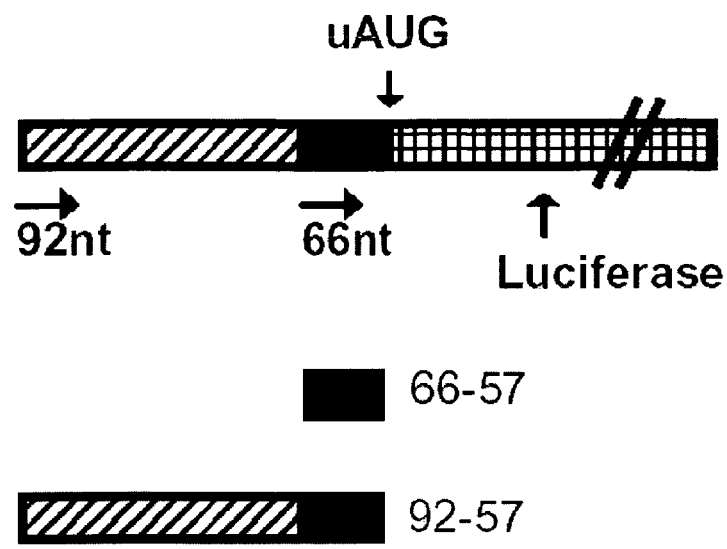
FIGS. 4A-4B show in vivo functionality of the AS uAUG when placed immediately upstream of a luciferase ORF. In order to direct expression of luciferase from the AS uAUG, AS 5'-UTR sequence spanning the region from either the 66 or 92 nt positions to the uAUG were cloned in front of luciferase in the pGL3 control vector to replace the luciferase 5'-UTR, shown in FIG. 4A. Constructs were transfected into BAEC. pGL3 Basic (Basic) was transfected as a negative control, pGL3 Control (Control) as a positive control and pRL-TK (Renilla) was co-transfected as an internal control. Luciferase activity was assayed 48 hours after transfection, and results were normalized to renilla activity, as shown in FIG. 4B. Error bars indicate the standard error of the mean from nine experiments.
Figure 4B:
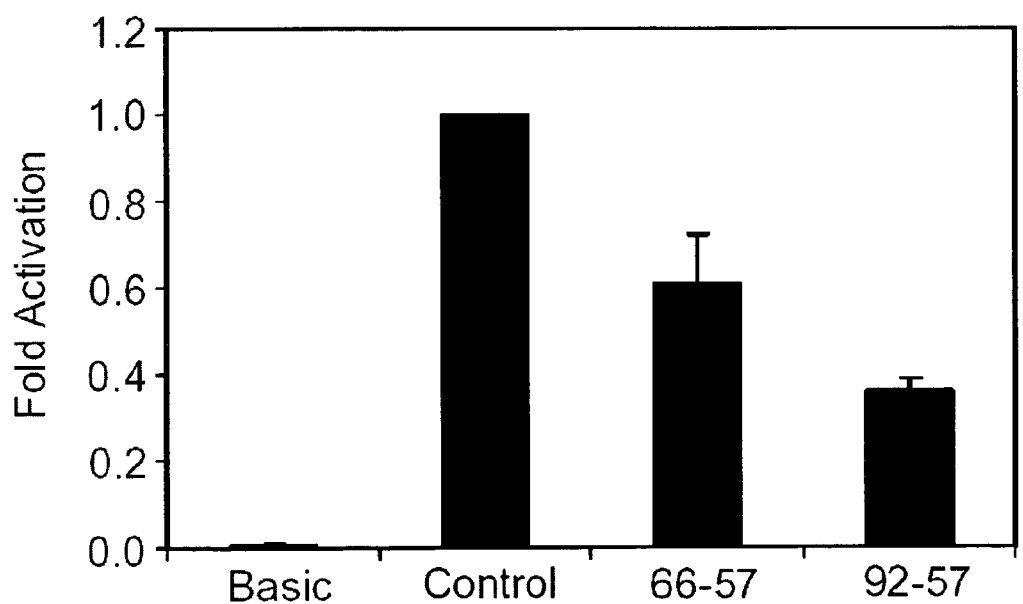

In vivo Functionality of the AS uAUG when Placed Immediately Upstream of a Luciferase ORF To demonstrate the functionality of the AS uAUG in endothelial cells, luciferase constructs were generated that replaced the luciferase 5'-UTR with forms of the extended AS 5'-UTRs, spanning the region from either the −66- or 92-nt positions to the uAUG. As shown in FIGS. 4A-4B, the construct containing the sequence from position −66 to −57 (the site of the uAUG) expressed luciferase activity at ~60% of control, while the −92- to −57-nt construct expressed luciferase activity at a lower level, ~36% of control. The fact that luciferase expression with the extended AS 5'-UTRs was lower that that of the control may reflect differences in the influence of the normal 5'-UTR versus the replacement AS 5'-UTRs. These results demonstrated that the uAUG is sufficient to support luciferase expression in endothelial cells.

EXAMPLE 3

Figure 5A:
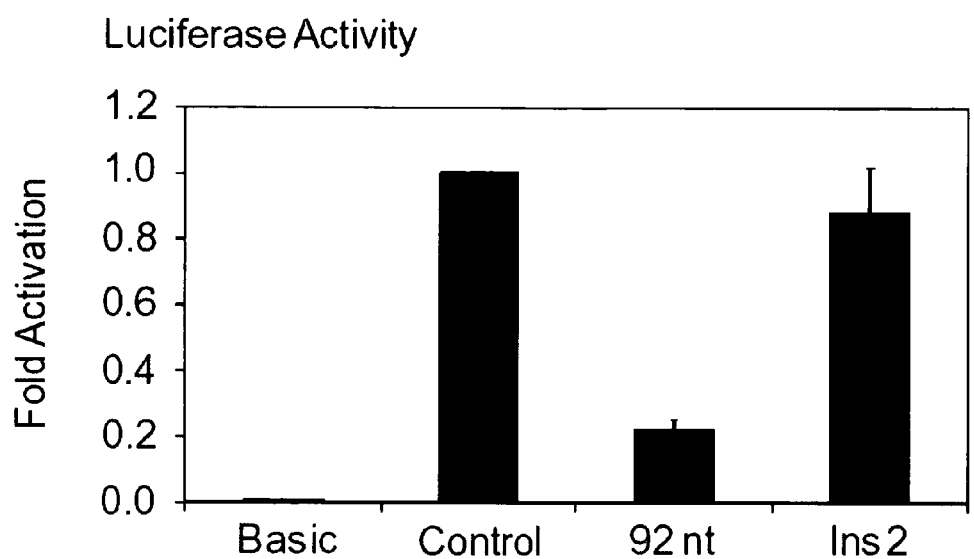
FIGS. 5A-5B show in vivo functionality of the AS uAUG in relation to a downstream luciferase ORF. A luciferase construct containing the entire 92 nt AS 5'-UTR in place of the luciferase 5'-UTR in pGL3 Control vector (92 nt) was constructed and mutated by inserting a single nucleotide at position −39 relative to the luciferase AUG (Ins 2) in order to put the uAUG and the luciferase AUG in frame. Constructs were transfected into BAEC. pGL3 Basic (Basic) was transfected as a negative control, pGL3 Control (Control) as a positive control and pRL-TK (Renilla) was co-transfected as an internal control. Luciferase activity, shown in FIG. 5A, was assayed 48 hours after transfection, and results were normalized to renilla activity. Error bars indicate the standard error of the mean from nine experiments. Equal amounts of cell lysate proteins were separated by SDS PAGE and standard western blotting was performed using anti-luciferase antibody, shown in FIG. 5B.
Figure 5B:
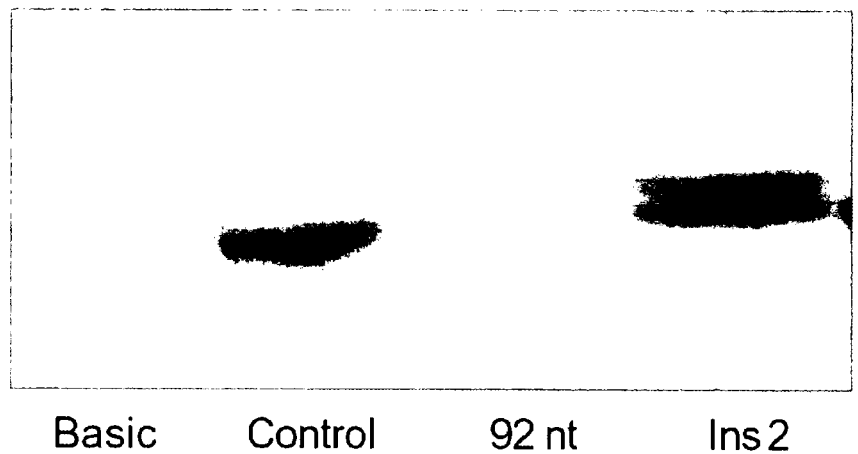

In vivo Functionality of the AS uAUG in Relation to a Downstream Luciferase ORF To determine the in vivo functionality of the AS uAUG in the presence of a downstream ORF, a full-length luciferase ORF construct was modified to contain the 92 nt AS 5'-UTR with the out-of-frame uAUG. An additional luciferase construct was generated that contained an Ins 2 mutation in the 92 nt AS 5'-UTR which positioned the AS upstream AUG and the downstream luciferase AUG in-frame. As shown in FIGS. 5A-5B, there was no significant difference in luciferase activity levels for the control construct and the insertion mutation (Ins 2) luciferase construct. However, the luciferase activity level for the 92-nt AS 5'-UTR luciferase construct containing an out-of-frame uAUG was approximately 20% of the control activity. Western blot analysis to follow luciferase protein levels showed a single band of ~61 kDa for the control construct and a barely detectable 61 kDa band for the 92 nt AS 5'-UTR/luciferase construct containing the out-of-frame uAUG. In contrast, the 92 nt AS 5'-UTR/luciferase construct with the Ins 2 mutation placing the uAUG in-frame, showed a doublet of ~61 and ~63 kDa. The 61-kDa protein corresponded to the luciferase ORF initiated from the downstream AUG, whereas the 63-kDa protein corresponded to a luciferase protein initiated from the in-frame uAUG in the 92-nt AS 5'-UTR Ins 2 construct. These results demonstrated that the uAUG in the extended 5'-UTR's of AS mRNA can function in the presence of a functional downstream ORF in endothelial cells.

EXAMPLE 4

Figure 6A:
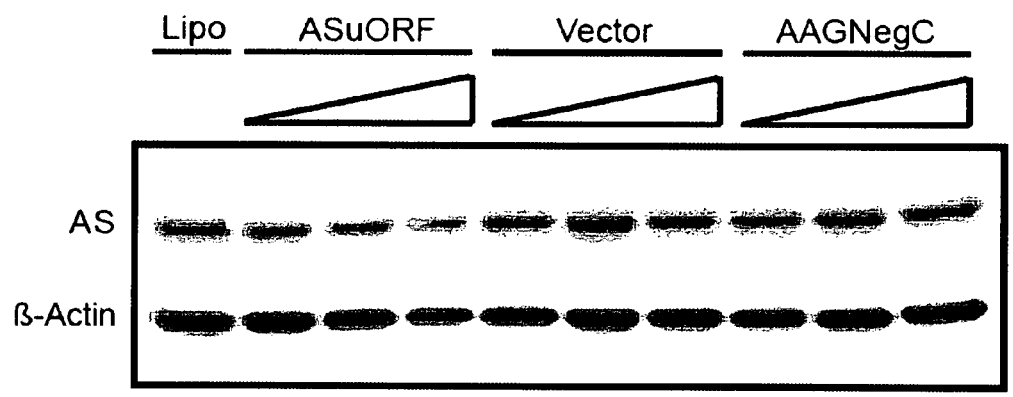
FIGS. 6A-6C show the effect of overexpression of the AS uORF on endothelial AS expression and NO production. The AS upstream open reading frame (ASuORF) was cloned into pcDNA3.1V5/His and transfected into BAEC. The ASuORF was compared to the AAGNegC construct where the uAUG is mutated to AAG, the empty vector (Vector) and a lipofectamine alone control (Lipo). Twenty-four hours after transfection, equal amounts of protein were separated by SDS-PAGE and standard Western blotting was performed using anti-AS and anti-β-Actin antibodies, shown in FIG. 6A. Quantitation of AS protein expression from three separate experiments, normalized to β-actin, is indicated as a fraction of the Lipofectamine alone control (FIG. 6B). Twenty-four hours after transfection, NO production was determined 2 hours after stimulation with 0.5 µM calcium ionophore and 50 µM sodium orthovanadate, shown in FIG. 6C. NO was measured as nitrite produced per $1 \times 10^6$ cells and normalized to lipofectamine alone levels.
Figure 6B:
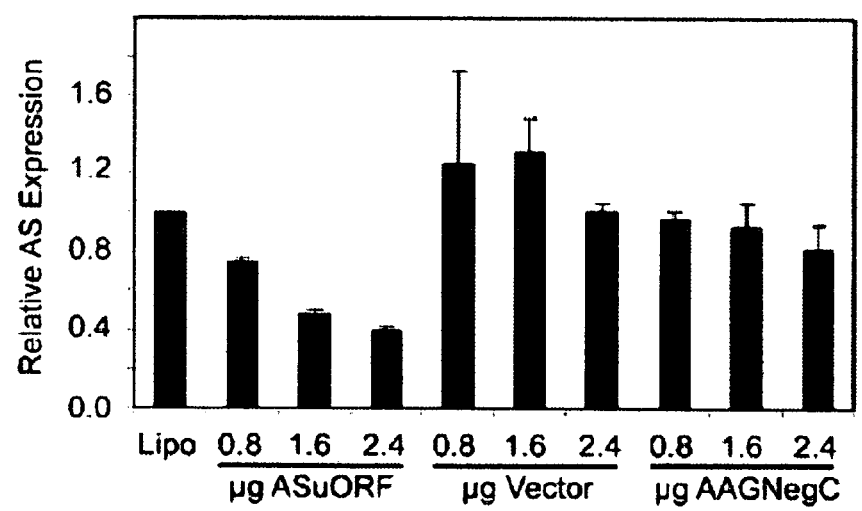
Figure 6C:
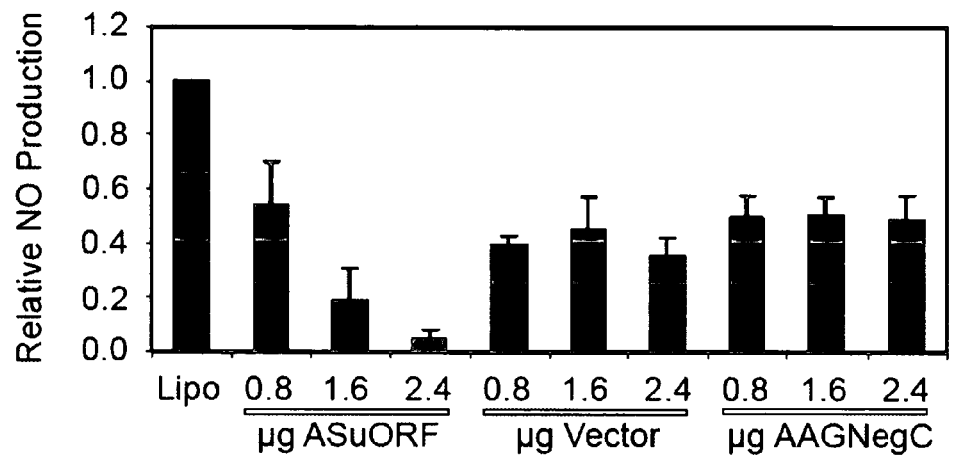

The Effect of Overexpression of the AS uORF on Endothelial AS Expression and NO Production To investigate possible trans-effects of the AS uORF, AS sequence from −92 to +70, relative to the AS AUG, was cloned into pcDNA3.1 vector so that the uORF was fused to a V5/His tag (ASuORF). For a negative control construct, the uAUG at position −59 was mutated to AAG, thereby rendering the AS uORF non-functional (AAGNegC). Equal amounts of protein from endothelial cells transfected with 0.8, 1.6, and 2.4 µg of ASuORF, AAGNegC, and vector plasmid DNA, along with a Lipofectamine-alone control, were analyzed by Western blot analysis with anti-V5 and anti-AS antibodies. The putative product of the uORF, approximately 7 kDa protein with the V5/His tag, could not be visualized by Western blotting with the V5 antibody. However, transfection of the AS uORF reduced endogenous AS protein levels, in a dose dependent fashion when compared to transfection reagent alone (FIGS. 6A-6C). Transfection of the pcDNA empty vector had no effect on endogenous AS protein levels, and the AS uORF negative control with the uAUG mutated to AAG had, at most, only a slight effect on AS expression. These results indicate that overexpression of the AS uORF elicited a profound trans-suppressive effect on endothelial AS expression. This suppression was not due to the presence of AS uORF-transfected RNA alone because overexpression of the mutation that deleted the uORF by converting the start codon to AAG (designed to be transcribed but not translated) had essentially no effect on AS expression.

The production of arginine by AS and AL in endothelial cells provides an essential source of arginine for NO production (Flam, B. R. et al. *Nitric Oxide*, 2001, 5:187-197; Goodwin, B. L. et al. *J Biol Chem.*, 2004, 279:18353-18360). To examine whether overexpression of the AS uORF and the accompanying decrease in AS protein had an effect on NO production, cells were stimulated twenty-fours after transfection with sodium orthovanadate and calcium ionophore (Hellermann, G. R. et al. *Arterioscler Thromb Vasc Biol*, 2000, 20:2045-2050). Aliquots were removed two hours after stimulation to measure nitrite as an indicator of cellular NO production. At the highest plasmid concentration of the ASuORF transfected, NO production was decreased to 5% of a control with Lipofectamine alone (FIGS. 6A-6C). Although the empty vector and the AAG mutant showed some negative effect relative to the Lipofectamine control, the magnitude and dose dependent decrease in NO production correlated significantly only with the loss of AS protein in AS uORF-treated cells. These results were also in keeping with those from previous work demonstrating the essential role of AS in endothelial NO production (Goodwin, B. L. et al. *J Biol Chem.*, 2004, 279:18353-18360), despite excessive levels of intracellular and extracellular arginine.

EXAMPLE 5

Requirement for AS uORF Sequence and Length for Suppression of Endothelial AS Protein Levels and NO Production To investigate whether sequence and/or length of the uORF are prerequisites for the trans-suppressive effects of the uORF on endogenous AS expression, we examined the overexpression of point mutation constructs with altered uORF structures. The first mutation was constructed with the initiation codon of the uORF left unchanged, but a deletion in the third codon and an insertion at the last codon caused a frameshift in the amino acid sequence. This frameshift mutation (uORFfs) yielded an ORF potentially encoding the same length peptide (44 amino acids), but where only the first two amino acids of the AS uORF were conserved. A second mutation was constructed with a new start codon for the AS uORF introduced 60 nucleotides downstream of the original, so as to potentially encode only 23 amino acids of the C terminus of the putative peptide (dnsAUG). A third mutation generated a construct where the stop codon was moved upstream in order to potentially encode 23 amino acids from the N terminus (upsStop) of the putative peptide.

Figure 7A:
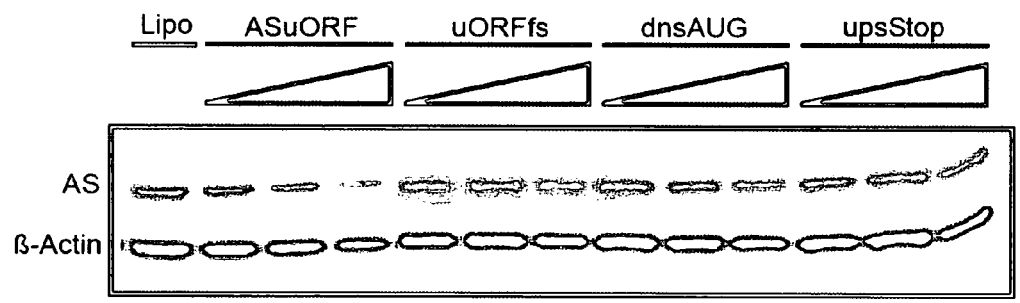
FIGS. 7A-7C demonstrate the requirement for AS uORF sequence and length for suppression of endothelial AS protein levels and NO production. Additional ASuORF pcDNA3.1V5/His constructs were prepared and transfected into BAEC and compared to the AS upstream open reading frame (ASuORF) construct and lipofectamine only (Lipo) control. The uORFfs construct was engineered to frameshift the entire sequence of the uORF so that only the first two amino acids were conserved, but the sequence length of 44 amino acids remained the same. The dnsAUG and upsStop constructs were designed to contain the C-terminal 23 amino acids and N-terminal 23 amino acids of the AS uORF respectively. Twenty-four hours after transfection, equal amounts of protein were separated by SDS-PAGE and standard Western blotting was performed using anti-AS and anti-β-Actin antibodies, shown in FIG. 7A. Quantitation of AS protein expression from three separate experiments, normalized to β-Actin, is indicated as a fraction of the Lipofectamine alone control, shown in FIG. 7B. Twenty-four hours after transfection, NO production was determined 2 hours after stimulation with 0.5 µM calcium ionophore and 50 µM sodium orthovanadate, shown in FIG. 7C. NO was measured as nitrite produced per $1 \times 10^6$ cells and normalized to lipofectamine only levels.
Figure 7B:
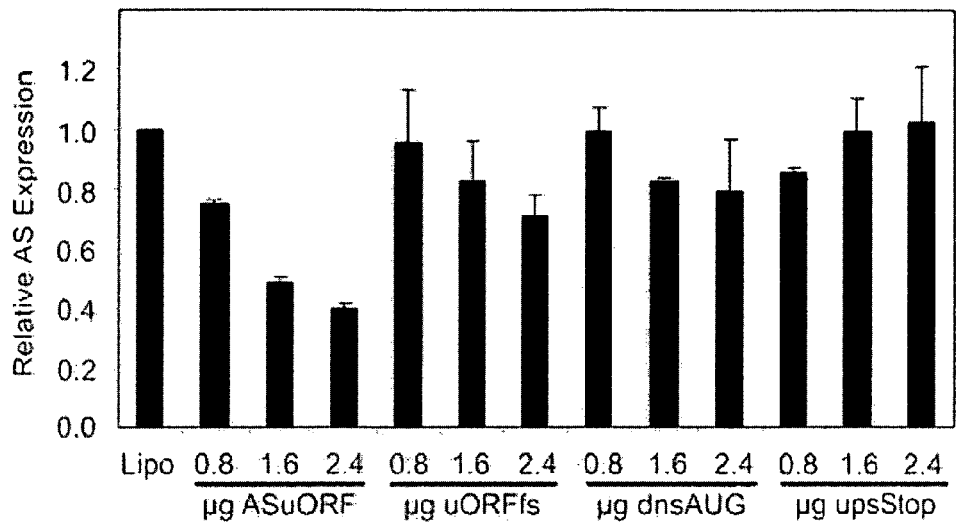
Figure 7C:
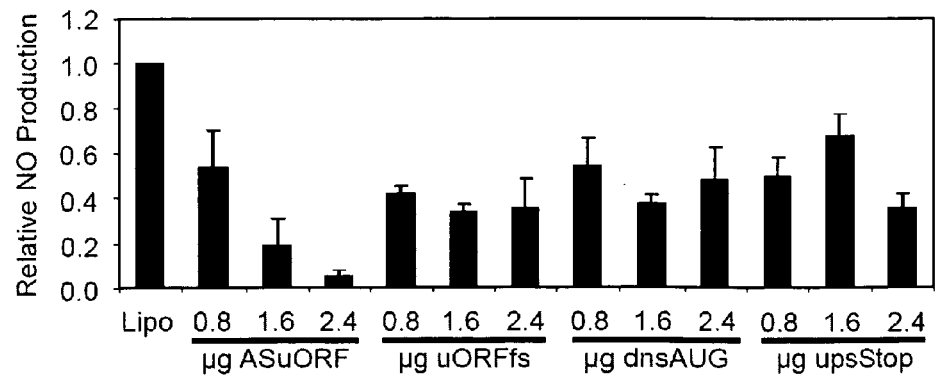

As shown in FIGS. 7A-7C, none of the mutated constructs showed the degree of suppression of AS expression or NO production exhibited by the wild-type AS uORF. These series of experiments demonstrated that both the sequence and the length of the AS uORF found in the extended 5'-UTR AS mRNAs are necessary to elicit negative trans effects on endothelial AS expression and NO production.

EXAMPLE 6

Regulation of AS Expression by the Translation Product of the AS uORF

Figure 8A:
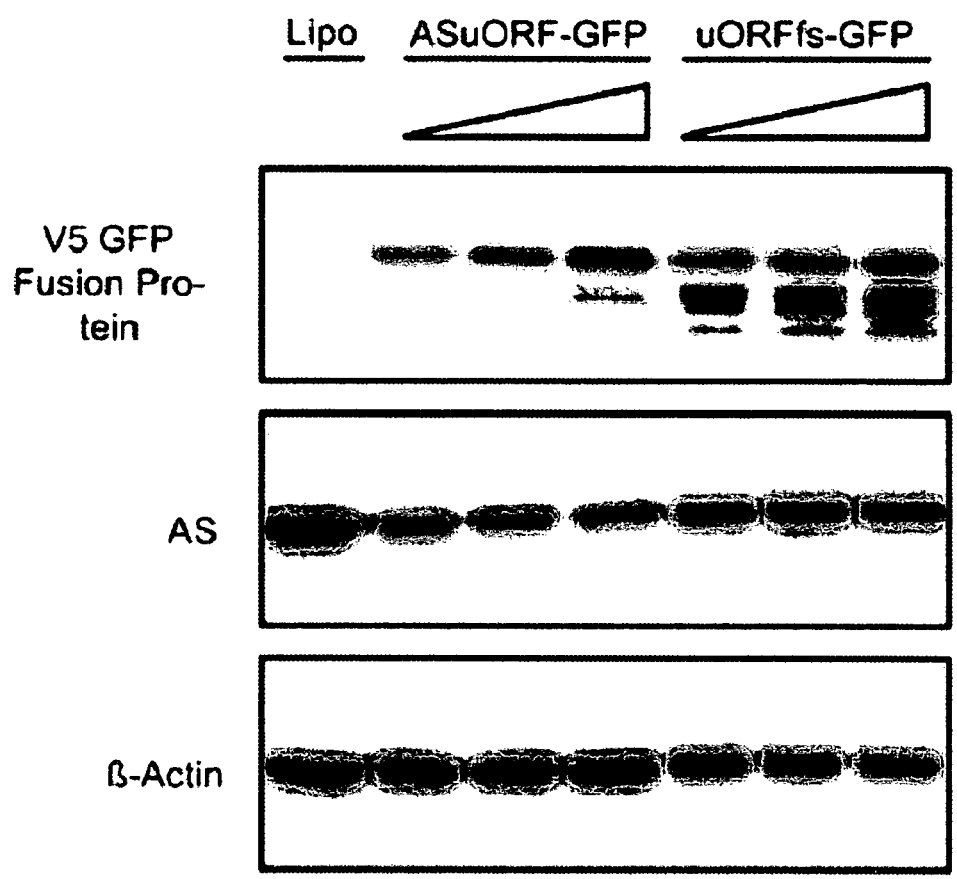
FIGS. 8A-8B show regulation of AS expression by the translation product of the AS uORF. An AS uORF construct was prepared in which GFP was cloned into the AsuORF pcDNA3.1/His construct between and in-frame with the AS uORF and the V5/His tags (ASuORF-GFP) was also inserted into the uORFfs (frameshift) construct (uORFfs-GFP). The GFP constructs were transfected into BAEC and compared with a Lipofectamine alone control (Lipo). Twenty-four hours after transfection, equal amounts of protein were separated by SDS-PAGE and standard Western blotting was performed using anti-V5, anti-AS, and anti-β-Actin antibodies, shown in FIG. 8A. Quantitation of AS protein expression, normalized to β-Actin, is indicated as a fraction of the Lipofectamine alone control, shown in FIG. 8B.
Figure 8B:
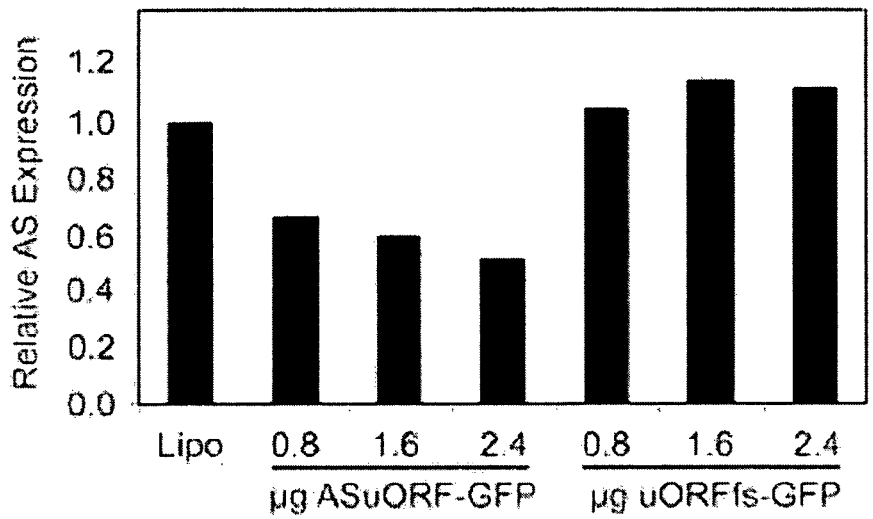

To demonstrate that the translation product of the AS uORF suppresses overall AS expression in endothelial cells and to facilitate detection of the translation product, the protein was tagged by cloning GFP between the AS uORF and the V5/His tags of the ASuORF pcDNA3.1/V5-His B construct. An additional construct involved GFP cloned into the AS uORF frameshift construct (uORFfs). Equal amounts of protein from lysates of endothelial cells transfected with 0.8, 1.6, and 2.4 µg of ASuORF-GFP and uORFfs-GFP, in addition to a Lipofectamine alone control, were analyzed by Western blot analysis. As shown in FIGS. 8A and 8B, a dose-dependent increase in the ASuORF-GFP-V5/His tag fusion protein (~37 kDa) directly correlated with a decrease in endogenous AS protein levels. Expression of the frameshift uORF construct, which produced a protein of equal size but different amino acid content, had no effect on AS protein levels. These results demonstrated that the protein encoded by the AS uORF mediates the negative trans effects on endothelial AS expression.

EXAMPLE 7

Figure 9A:
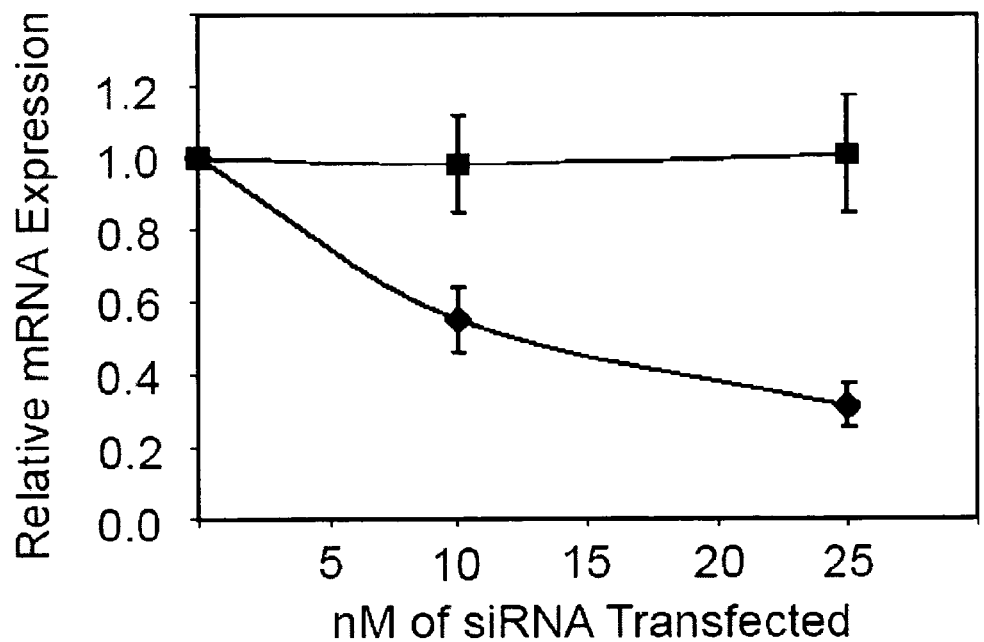
Figure 9B:
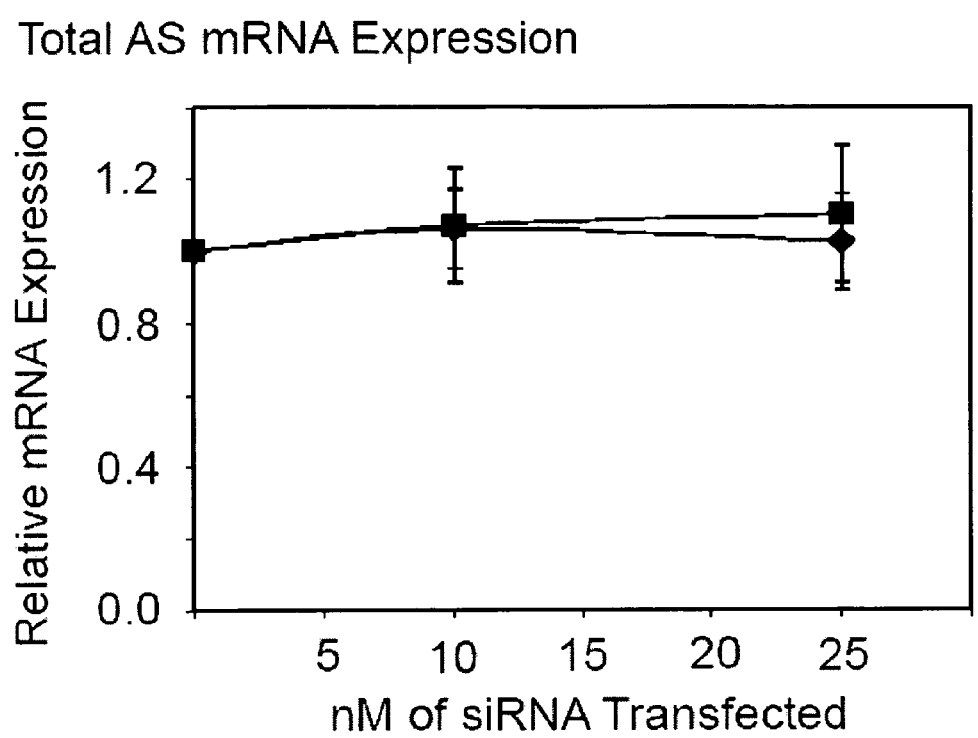

Effect of Silencing of the Extended 5'-UTR AS mRNAs on Endothelial AS Expression To further demonstrate the trans suppressive effect of the uORF on endothelial AS expression, an siRNA was designed to selectively knockdown the 92- and 66-nt 5'-UTR AS mRNA species. Analysis of AS mRNA in transfected endothelial cells by real-time reverse transcriptase-PCR (RT-PCR) demonstrated that a scrambled form of the siRNA (control) had no effect on the levels of the extended forms of AS mRNA. In contrast, an siRNA directed against the extended 5'-UTR AS mRNA species decreased both the 92- and 66-nt 5'-UTR AS mRNAs to ~20% of transfection reagent alone (FIGS. 9A-9C). Importantly, the level of total AS mRNA was essentially unaffected, consistent with the fact that the extended 5'-UTR forms of AS mRNA containing the uORF represent less than 7% of the total message. Equal amounts of protein from the extended AS 5'-UTR siRNA and from scrambled siRNA transfected endothelial cells were examined by Western blot analysis using anti-AS antibody. AS protein levels, normalized to glyceraldehyde-3-phosphate dehydrogenase (GAPDH) expression, were markedly increased in response to selective silencing of the 92- and 66-nt 5'-UTR AS mRNAs. An ~2.3-fold increase in expressed AS protein was seen compared to the scrambled siRNA at the 25 nM concentration of siRNA (FIGS. 9A-9C). These results suggest that the trans effects of the uORF found in the extended 5'-UTR AS mRNA forms are mediated post-transcriptionally, and most likely at the translational level.

EXAMPLE 8

Effect of Silencing of the Extended 5'-UTR AS mRNAs on NO Production

Based on the previous results demonstrating that AS expression levels are coordinately linked to the production of NO in endothelial cells, we examined whether the knockdown of the endogenous extended 5'-UTR AS mRNA species and the accompanying increase in AS protein has an effect on the NO produced in these cells. Aliquots of media were removed twenty-four hours after transfection of 25 nM siRNA specific for the extended AS 5'-UTR or a scrambled negative control siRNA, and nitrite as an indicator of cellular NO production was measured. As shown in Table 1, an ~2.2 fold increase in basal cellular NO produced (measured as nitrite) in the extended AS 5'-UTR siRNA treated cells was observed compared to the scrambled siRNA treated cells. This increase in NO production correlated closely with the increased expression of AS in response to the knockdown of extended 5'-UTR AS mRNA forms (FIGS. 9A-9C).

TABLE 1

Effect of silencing of the extended 5'-UTR AS mRNAs on NO production.

| Condition | Relative NO Produced |
|---|---|
| 25 nM scrambled siRNA | 1.00 |
| 25 nM siRNA | 2.2 ± 0.33 |

BAEC were transiently transfected with siRNA specific for the 92- and 66-nt 5'-UTR species of AS mRNA and a scrambled negative control siRNA. Basal NO production was determined over a twenty-four hour period. NO was measured as nitrite produced per $1 \times 10^6$ cells and normalized to scrambled siRNA levels.

We previously established that the recycling of citrulline to arginine is essential to provide the substrate arginine for NO production, even in the presence of saturating levels of intra- and extracellular arginine (Flam, B. R. et al. *Nitric Oxide,* 2001, 5:187-197; Goodwin, B. L. et al. *J Biol Chem,* 2004, 279:18353-18360). We demonstrate in this study that expression of the extended 5'-UTR forms of AS mRNA, containing an uORF, mediates a trans effect, suppressing overall endothelial AS expression and causing a corresponding suppression of endothelial NO production. This suppression of AS expression requires a functional, out-of-frame uORF represented in the 5'-UTR regions of the co-expressed extended forms of endothelial AS mRNA (Pendleton, L. C. et al. *J Biol Chem,* 2002, 277:25363-25369). The uORF AUG was shown to be functional both in vitro and in vivo. When the uAUG was put in-frame with the downstream AUG by inserting a nucleotide, two in vitro translated $^{35}$S-labeled products were evidenced by electrophoretic SDS-polyacrylamide gel analysis. The larger AS species (~49 kDa) was initiated from the uAUG, while the smaller (~47 kDa) species represented the translation product initiated from the normal, downstream reading frame encoding AS. Interestingly, the ratio of products in this case favored use of the uAUG. Moreover, when the context of this uAUG was altered to better match the Kozak consensus initiation sequence (Kozak, M. *Gene,* 1999, 234: 187-208), translation significantly improved from the uAUG. To demonstrate that this uORF, when positioned out-of-frame, was still translated, two putative stop codons for the uORF were mutated to allow production of a larger, more easily identifiable translation product (~21 kDa). Although the difference in methionine content did not permit a quantitative comparison by $^{35}$S-labeling, the results clearly demonstrated a 21-kDa product, confirming the functionality of the uORF in its natural context.

With the support of in vitro results, we then assessed the in vivo functionality of the uORF in endothelial cells using a luciferase reporter assay. Expression of luciferase from the uAUG demonstrated that the context of the uAUG is sufficient to support initiation of translation. Moreover, when the AS uAUG start codon was positioned in-frame, in the context of the entire 5'-UTR and preceding the normal start codon for a luciferase gene, our results again demonstrated functionality. In this case, two luciferase products were identified by Western blot analysis consistent with the interpretation that both the uAUG and the downstream luciferase AUG are recognized in endothelial cells.

Previous work from our laboratory suggested that AS mRNA species containing the uORF in the extended 5'-UTR sequence do not express AS well, either in vitro or in vivo, due to cis effects of the uORF (Pendleton, L. C. et al. *J Biol Chem,* 2002, 277:25363-25369). In this paper, we have clarified not only the functionality of the uORF, but also its trans-mediated effects, showing that overexpression of this uORF resulted in a dramatic decrease in AS expression in endothelial cells. This result suggested that the co-expression of the extended 5'-UTR forms of AS mRNA, containing an out-of-frame uORF, may play a role in suppressing the overall expression of endothelial AS. Additionally we showed that NO production is significantly reduced when the AS uORF is overexpressed, further linking the requirement for AS expression to NO production in endothelial cells. The fact that AS expression was not suppressed when the uORF was rendered nonfunctional, via loss of an operational start codon, or by overexpression of ASuORF containing either a frameshift mutation, or altered start or stop codons, demonstrated that the entire sequence of the uORF is required to mediate the trans effects that decrease endothelial AS expression and NO production. Furthermore, a direct effect was observed that related expression of the translational product encoded by the uORF to the suppression of endothelial AS expression.

When expression of the endothelial extended 5'-UTR AS mRNA species were specifically silenced by siRNA treatment, expression of AS increased dramatically (~2-fold), despite the fact that these species represent less than 7% of the total AS mRNA. Consistent with the rate-limiting role of AS in recycling citrulline to arginine and in maintaining the essential arginine for NO production, knockdown of the extended 5'-UTR AS mRNA species containing this uORF resulted in an increased capacity of endothelial cells to produce NO. Thus, the overall results suggest that the uORF found in the extended 5'-UTR forms of endothelial AS mRNA is functional, and as such expresses a protein product that acts to suppress expression of the predominant short form of the AS mRNA.

In summary, a small protein produced through expression of the uORF of the extended 5'-UTRs of two minor forms of AS mRNA, unique to endothelial cells, suppresses AS expression. The overall effect of this suppression of AS expression is to decrease NO production in endothelial cells by limiting the availability of the substrate arginine. These results provide evidence for a novel mechanism for the regulation of endothelial AS protein expression and further support the essential role of the citrulline-NO cycle in endothelial NO production.

EXAMPLE 9 siRNA Designed to Silence Human Extended 5'-UTR AS mRNAs

As discussed above, RNAi is a cellular process wherein short double-stranded RNAs (siRNAs) direct the degradation of transcripts containing sequence complementary to at least one of the siRNA strands (Fire A. et al., *Nature*, 1998, 391 (6669):8061 1; Tuschl T. et al., *Genes Dev.*, 1999, 13(24): 31917). siRNAs induce RNA degradation through the protein complex known as the RNA Induced Silencing Complex (RISC) (Zamore P. D. et al., *Cell*, 2000, 101(1):2533). Much evidence indicates that the RISC contains only one of the two siRNA strands, suggesting that there is a step prior to, or during, the incorporation of the siRNA into the RISC by which the one of the siRNA strands is removed (Martinez J. et al., 2002, *Cell*, 110(5):56774; Nykanen A. et al., *Cell*, 2001, 107(3):30921). Either siRNA strand can be taken up by the RISC, but the complex can only direct degradation of cellular RNAs that are complementary to the bound siRNA (Elbashir S. M. et al., 2001, *EMBO J.*, 20(23):687788). Recent research suggests that strand selection can be affected by the nucleotide composition of the siRNA (Schwarz D. et al., *Cell*, 115(2): 199208; Khvorova A. et al., 2003, *Cell*, 115(2):20916). On this basis, it is possible to select siRNA target sites that favor incorporation of the antisense siRNA strand into the RISC to increase the percentage of RISCs containing the correct targeting siRNA strand, resulting in improved efficacy and specificity of the RNA. Several publicly available siRNA design algorithms have emerged reporting high success rates for silencing human genes. Some siRNA design programs have shown success rates of 50-60% in generating siRNAs that can yield over 70% silencing of target mRNA levels in HeLa cells after 48 hours. In collaboration with AMBION, CENIX BIOSCIENCE conducted an analysis of the CENIX algorithm's success rate. The analysis revealed that when three CENIX designed siRNAs per gene were tested, one or more of the siRNAs achieved over 70% silencing for over 93% of tested genes, over 80% silencing for nearly 80% of tested genes, and over 90% silencing for approximately half of tested genes (data available on AMBION web site). On a per siRNA basis, approximately 80% of the individual siRNAs showed greater than 70% silencing of their target.

There are several methods for preparing siRNA, such as chemical synthesis, in vitro transcription, siRNA expression vectors, and PCR expression cassettes. Irrespective of which method one uses, the first step in designing a siRNA is to choose the siRNA target site, which in this case is the extended 5'-UTR AS mRNA. AMBION's online target finder may be used to identify potential sequences based on the design guidelines published by Tuschl, Elbashir et al. (*EMBO J.*, 2001, 20:6877-6888), Editors of *Nature Cell Biology* (Whither RNAi, 2003, 5:489-490), and others. The target mRNA sequence is simply pasted into the window and the AMBION program will scan the sequence for AA dinucleotides. A report is generated indicating the position of the AA dinucleotide, the 21 base target and the corresponding sense and antisense siRNA oligonucleotides. siRNA targets can then be sent directly to a kit-specific design tool or subjected to a BLAST search by clicking the appropriate link below the target of interest. Alternatively, the Whitehead Institute of Biomedical Research at MIT has a publicly available siRNA design tool that incorporates additional selection parameters and integrates BLAST searches of the human and mouse genome databases.

siRNA Hairpin Design

Researchers initially reporting the use of siRNA expression vectors to induce RNAi had different design criteria for their inserts encoding the expressed siRNA. Most of these designs had two inverted repeats separated by a short spacer sequence and ending with a string of T's that served as a transcription termination site. These designs produce an RNA transcript that is predicted to fold into a short hairpin siRNA as shown in FIG. 11 (AMBION web site). The selection of siRNA the target sequence, the length of the inverted repeats that encode the stem of a putative hairpin, the order of the inverted repeats, the length and composition of the spacer sequence that encodes the loop of the hairpin, and the presence or absence of 5'-overhangs, vary with different reports (Brown D. et al., AMBION *TechNotes*, 2002, 9(1):3-5; Sui G. et al., *Proc. Natl. Acad. Sci. USA*, 2002, 99(8):5515-5520; Lee N. S. et al., *Nature Biotechnology*, 2002, 20:500-505; Yu J.-Y. et al., *Proc. Natl. Acad. Sci. USA*, 2002, 99(9):6047-6052; Paul C. P. et al., *Nature Biotechnology*, 2002, 20:505-508; Brummelkamp T. R. et al., *Science*, 2002, 296:550-553; Jacque J.-M. et al., *Nature*, 2002, 418:435-438; Miyagishi M. et al., *Nature Biotechnology*, 2002, 20:497-500; Paddison P. J. et al., *Genes Devel.*, 2002, 948-958).

For screening, multiple siRNA sequences (e.g., four sequences) can be tested per target, spacing the siRNA sequences down the length of the gene sequence to reduce the chances of targeting a region of the mRNA that is either highly structured or bound by regulatory proteins. Because constructing and testing multiple siRNA expression plasmids per target can be time-consuming, potential siRNA sequences can be screened using PCR-derived siRNA expression cassettes (SECs). SECs are PCR products that include promoter and terminator sequences flanking a hairpin siRNA template and can be prepared using commercially available kits (e.g., AMBION SILENCER Expression Kit). This screening strategy also permits the rapid identification of the best combination of promoter and siRNA sequence in the system. SECs found to effectively elicit gene silencing can be readily cloned into a vector for long term studies. Preferably, siRNA sequences to be expressed in vivo should not contain a run of 4 or 5 A's or T's, as these can act as termination sites for Polymerase III.

Figure 13:
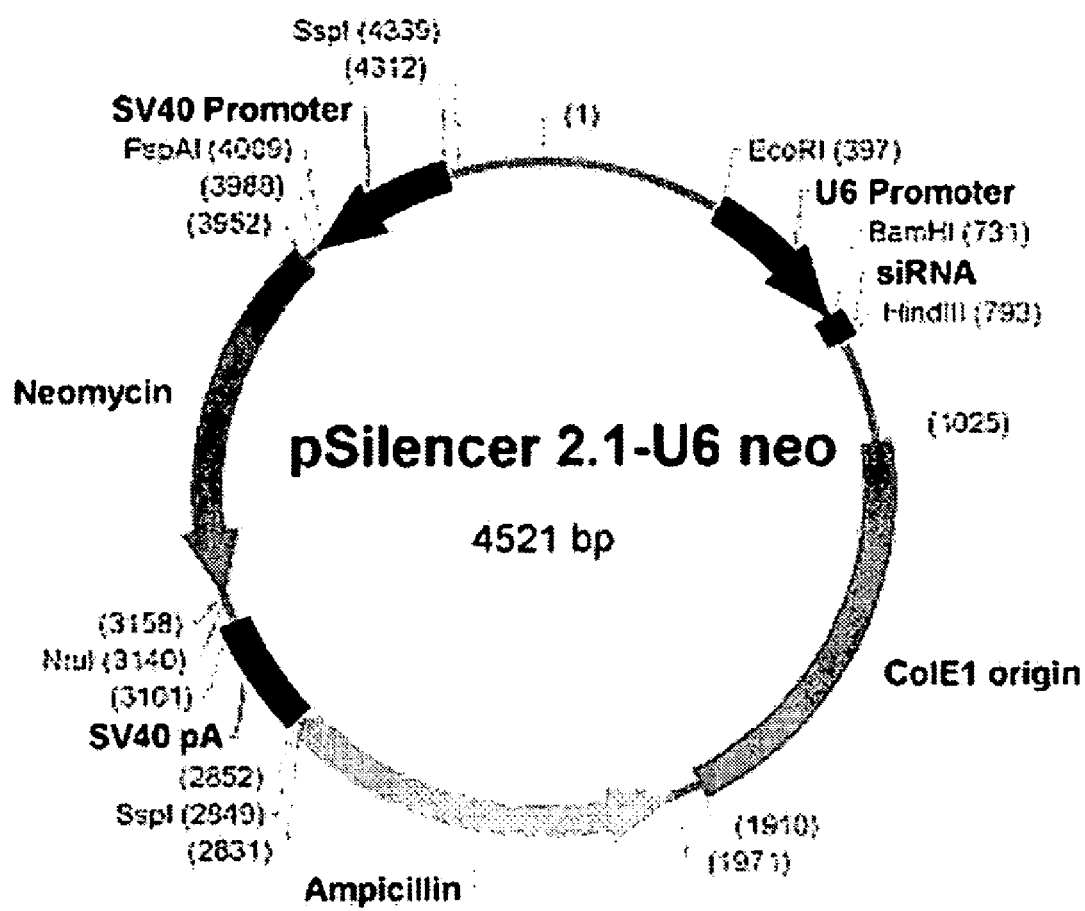
FIG. 13 shows a pSILENCER 2.1-U6neo vector map (AMBION website). U6 promoter: 397-731; SV40 early promoter: 3988-4312; neomycin: 3158-3952; SV40 early pA signal: 2852-3101; ampicillin: 1971-2831; ColE1 origin: 1025-1910.

For traditional cloning into vectors (e.g., pSILENCER vectors), two DNA oligonucleotides that encode the chose siRNA sequence are designed for insertion into the vector (as shown in FIG. 12). In general, the DNA oligonucleotides comprise a 19-nucleotide sense siRNA sequence linked to its reverse complementary antisense siRNA sequence by a short spacer. Scientists have successfully used a 9-nucleotide spacer (TTCAAGAGA), although other spacers can be designed. 5-6 T's are added to the 3' end of the oligonucleotide. In addition, for cloning into the pSILENCER 1.0-U6 vector, for example, nucleotide overhangs to the EcoR I and Apa I restriction sites are added to the 5' and 3' end of the DNA oligonucleotides, respectively. In contrast, for cloning into the p9Silencer 2.0-U6, 2.1-U6, 3.0-H1, or 3.1-H1 vectors, nucleotide overhangs with BamH I and Hind III restriction sites are added to the 5' and 3' end of the DNA oligonucleotides, respectively, as shown in FIG. 12. The resulting RNA transcript is expected to fold back and form a stem-loop structure comprising a 19 base pair (bp) stem and 9 nucleotide (nt) loop with 2-3 U's at the 3' end, as shown in FIG. 11. In FIG. 12, the * denotes that this non-complementary base pair should be included only if the following base on the op strand (the +1 position of the siRNA) is a T or a C; if the +1 position is a G or an A, it should not be included. A vector map of the pSILENCER 2.1-U6neo vector is shown in FIG. 13.

In addition to the algorithm developed by CENIX, and AMBION's suggested procedure for selecting siRNA targets by scanning an mRNA sequence for AA dinucleotides and recording the 19 nucleotides immediately downstream of the AA, two other methods have been employed by other researchers. In the first method, the selection of the siRNA target sequence is purely empirically determined, as long as the target sequence starts with GG and does not share significant sequence homology with other genes as analyzed by BLAST search (Sui G. et al., *Proc. Natl. Acad. Sci. USA*, 2002, 99(8):5515-5520). The second method for selection of siRNA target sequences is more elaborate, exploiting an observation that any accessible site in endogenous mRNA can be targeted for degradation by the synthetic oligodeoxyribonucleotide/RNase H method (Lee N. S. et al., *Nature Biotechnology*, 2002, 20:500-505). Any accessible site identified in this fashion can then be used as an insert sequence in the U6 promoter-driven siRNA constructs.

Typically, a hairpin siRNA expression cassette is constructed to contain the sense strand of the target, followed by a short spacer, then the antisense strand of the target, in that order. However, researchers have found that reversal of the order of sense and antisense strands within the siRNA expression constructs did not affect the gene silencing activities of the hairpin siRNA (Yu J.-Y. et al., *Proc. Natl. Acad. Sci. USA*, 2002, 99(9):6047-6052). Another group of researchers has found that similar reversal of order in another siRNA expression cassette caused partial reduction in the gene silencing activities of the hairpin siRNA (Paul C. P. et al., *Nature Biotechnology*, 2002, 20:505-508). Presently, it is still advised to construct the siRNA expression cassette in the order of sense strand, short spacer, and antisense strand.

There is some degree of variation in the length of nucleotide sequence being used as the stem of siRNA expression cassettes. Several groups have used 19 nucleotide-long sequences as the stem (Yu J.-Y. et al., *Proc. Natl. Acad. Sci. USA*, 2002, 99(9):6047-6052; Paul C. P. et al., *Nature Biotechnology*, 2002, 20:505-508; Brumnmelkamp T. R. et al., *Science*, 2002, 296:550-553; Jacque J.-M. et al., *Nature*, 2002, 418:435-438; Miyagishi M. et al., *Nature Biotechnology*, 2002, 20:497-500). Other groups have used siRNA stems ranging from 21 nucleotides-long (Sui G. et al., *Proc. Natl. Acad. Sci. USA*, 2002, 99(8):5515-5520; Lee N. S. et al., *Nature Biotechnology*, 2002, 20:500-505) to 25-29 nucleotides-long (Paddison P. J. et al., *Genes Devel.*, 2002, 948-958). It has been found that hairpin siRNAs with these various stem lengths function well in gene silencing studies.

Research groups have reported successful gene silencing results using hairpin siRNAs with loop sizes ranging from between 3 to 23 nucleotides (Sui G. et al., *Proc. Natl. Acad Sci. USA*, 2002, 99(8):5515-5520; Yu J.-Y. et al., *Proc. Natl. Acad. Sci. USA*, 2002, 99(9):6047-6052; Paul C. P. et al., *Nature Biotechnology*, 2002, 20:505-508; Brummelkamp T. R. et al., *Science*, 2002, 296:550-553; Jacque J.-M. et al., *Nature*, 2002, 418:435-438; Paddison P. J. et al., *Genes Devel.*, 2002, 948-958). Most research groups did not use a 5' overhang in their hairpin siRNA construct. However, one research group included a 6-nucleotide 5' overhang in the hairpin siRNA constructs (Jacque J.-M. et al., *Nature*, 2002, 418:435-438). These hairpin siRNAs with 5' overhangs were shown to be functional in gene silencing. Early indications suggest that a great deal of latitude is possible in the design of the loop.

Design of siRNA for AS 5'-UTR Extended Forms

An siRNA can be designed to silence (e.g., partially or completely reduce expression) of extended 5'-UTR AS mRNAs.

```
siRNA seq:
AACCCGGGATGCGCGCCGAAA                      (SEQ ID NO:22)

Top Strand:
5'-GATCCGCCCGGGATGCGCGCCGAAATTCAAGAG (SEQ ID NO:23)
ATTTCGGCGCGCATCCCGGGTTTTTGGAAA-3'

Bottom Strand:
5'AGCTTTTCCAAAAAACCCGGGATGCGCGCCGAAA (SEQ ID NO:24)
TCTCTTGAATTTCGGCGCGCATCCCGGGCG-3'
```

The two strands are annealed, leaving overhangs ready for cloning directly into the pSilencer 2.1U6neo vector, the vector map for which is shown in FIG. 13 (AMBION, catalog #5764).

Design of siRNA from Human Sequence

FIG. 14 shows the human sequence for AS 5'-UTR extended form from GenBank accession no. NM_054012, which is incorporated herein by reference in its entirety. When this sequence is entered into the siRNA Target Finder program on the AMBION web site, using the recommended (default) parameters, the following target sequence is selected: AACCTGGGATGGGCACCCCTG (SEQ ID NO:25), which starts exactly in the same location as the bovine siRNA, relative to the upstream AUG. In one embodiment, the siRNA target differs by 1, 2, or 3 nucleotides from AACCTGGGAUGGGCACCCCTG (SEQ ID NO:25). In one embodiment, the siRNA sequence comprises AAC-CCGGGATGCGCGCCGAAA (SEQ ID NO:22), or a sequence having a substitution and/or deletion of 1, 2, or 3, nucleotides anywhere in the sequence. Deletions or substitutions of 2 or 3 nucleotides can be consecutive within the sequence or incremental (with one or more nucleotides between the deletion or substitution).

EXAMPLE 10

Do AS mRNA Polysome Profiles Change with Overexpression or Knockdown of the uORF?

Figure 15:
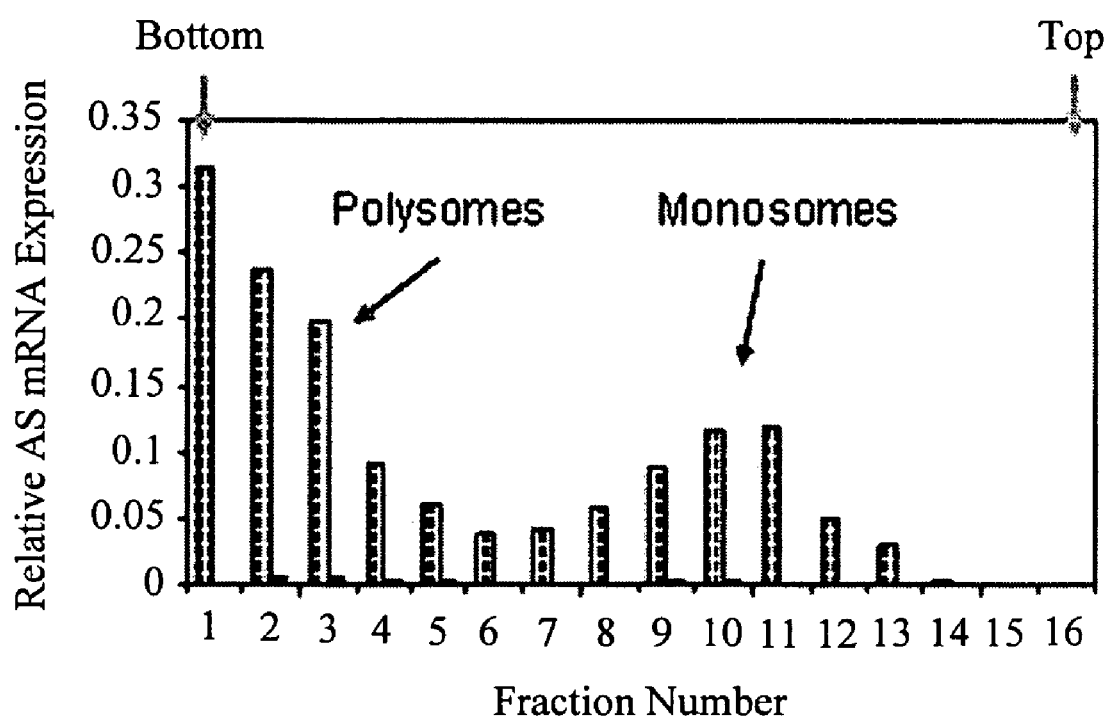
FIG. 15 shows gradient fractionation, 15%-50% Sucrose, of cytosolic fractions. The solid bars represent the relative amounts of AS mRNA from ASuORF transfected cells. The checked bars represent the relative amounts of AS mRNA from the non-functional frame shift uORF transfected cells.

Polysome profile analyses will be utilized from uORF overexpressed, uORF knockdown, and control endothelial cells to determine whether changes in eAS expression correlate with a redistribution of eAS transcript in polysomes. The polysome profile for the housekeeping gene β-Actin will be used as a control for non-specific effects on translation. Briefly, cytoplasmic fractions from cultured endothelial cells are centrifuged through a 15-50% linear sucrose gradient following. The gradient polysome profile is generated by monitoring absorbance at 260 nm, and RNA from each fraction is isolated. The distribution of eAS mRNA along the profile is quantitated by real time-RT PCR. Results of preliminary experiments, shown in FIG. 15, demonstrate a significant diminished distribution of eAS mRNA along the entire polysome profile as a consequence of the overexpression of a transfected uORF construct, whereas transfection with the non-functional frame shift uORF had no effect.

EXAMPLE 11

Do eAS mRNA Polysome Profiles Change in Response to Physiological Signals that Affect Endothelial NO Production?

The present inventors will examine whether the distribution of eAS mRNA in polysome profiles change in response to physiological signals that affect eAS expression such as TNF-α treatment, hypoxia, or FSS. If so, these results would provide evidence that physiological signals which alter endothelial NO production may mediate their response at multiple levels, including translation of the eAS mRNA.

EXAMPLE 12

How Does the uORF Encoded Protein Inhibit in vitro Translation of the 43nt Exon 1 eAS mRNA?

Figures 16A, 16B:
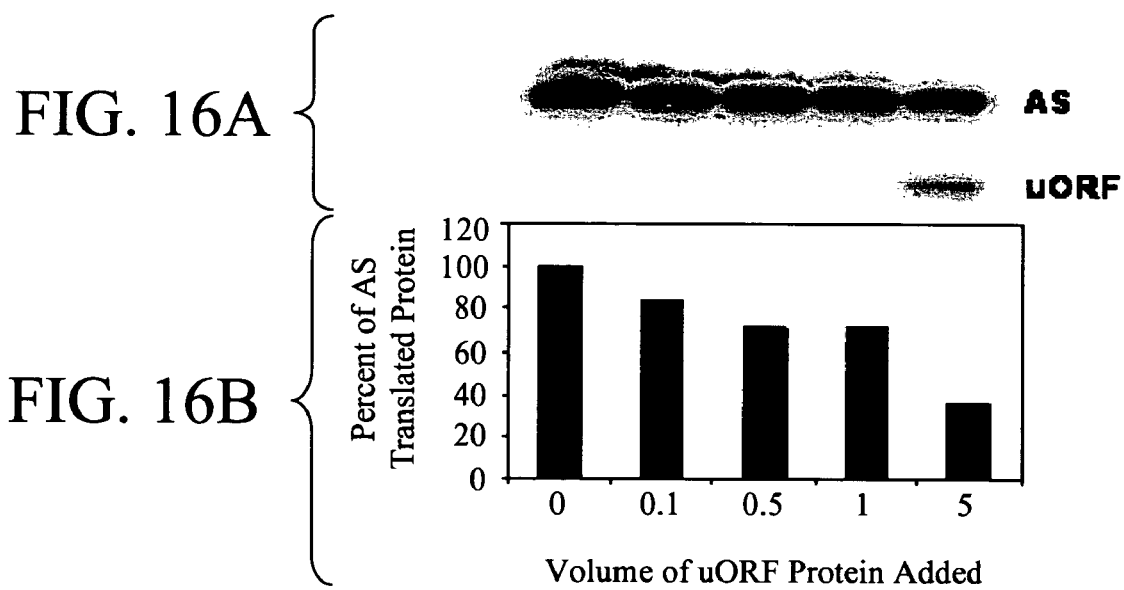
FIGS. 16A-16B show a Western blot analysis of in vitro translated AS in the presence of increasing amounts of in vitro translated uORF protein. Both proteins contain a V5 tag; therefore, detection is done with a V5 antibody.

To address the question of how the uORF encoded protein inhibits in vitro translation of the 43 nt Exon 1 eAS mRNA, the 43 nt exon 1 eAS mRNA will be translated in the presence of various levels of uORF protein to ascertain whether it can directly inhibit translation in vitro. As shown in FIGS. 16A and 16B, preliminary evidence suggests that translational inhibition in vitro can be observed directly. To determine whether there is direct binding of the uORF encoded protein to the 43 nt exon 1 eAS mRNA, ribonucleoprotein immunoprecipitation assays (RIP) will be carried out. Briefly, overexpressed uORF protein tagged with V5 will be immunoprecipitated with a V5 antibody from transfected endothelial cell lysates. Messenger RNA bound to the immunoprecipitates will be extracted and characterized by real-time RT-PCR, cloning and sequencing.

All patents, patent applications, provisional applications, accession numbers, and publications referred to or cited herein are incorporated by reference in their entirety, including all figures and tables, to the extent they are not inconsistent with the explicit teachings of this specification.

---

We claim:

1. An isolated polynucleotide that targets an out-of-frame, upstream, overlapping open reading frame within the extended 5'-untranslated region (5'-UTR) of argininosuccinate sythase (AS), wherein said polynucleotide reduces expression of two messenger RNA molecules having initiation sites at nucleotide −92 and nucleotide −66 relative to nucleotide 117 of SEQ ID NO:33.

2. The polynucleotide of claim 1, wherein said polynucleotide is an interfering RNA, anti-sense oligonucleotide, or ribozyme.

3. The polynucleotide of claim 1, wherein said polynucleotide is an interfering RNA that targets nucleotides −65 to −47 relative to nucleotide 117 of SEQ ID NO:33.

4. The polynucleotide of claim 1, wherein said polynucleotide is an interfering RNA that targets AACCTGG-GATGGGCACCCCTG (SEQ ID NO:25).

5. The polynucleotide of claim 1, wherein said polynucleotide is an interfering RNA comprising AAC CCG GGA UGC GCG CCG AAA (SEQ ID NO:22).

6. The polynucleotide of claim 1, wherein said polynucleotide is an interfering RNA comprising CCC GGG AUG CGC GCC GAA AUU (SEQ ID NO:1).

7. The polynucleotide of claim 1, wherein said polynucleotide is an siRNA.

8. The polynucleotide of claim 1, wherein said polynucleotide is an shRNA.

9. The polynucleotide of claim 1, wherein said extended 5'-UTR AS mRNA mammalian mRNA.

10. The polynucleotide of claim 1, wherein said extended 5'-UTR AS mRNA mammalian mRNA.

11. A composition comprising the isolated polynucleotide of claim 1, and a pharmaceutically acceptable carrier.

12. The polynucleotide of claim 1, wherein said polynucleotide increases endothelial AS production, and increases endothelial nitric oxide production.

13. The polynucleotide of claim 11, wherein said extended 5'-UTR AS mRNA mammalian mRNA.

14. The composition of claim 11, wherein said polynucleotide is an interfering RNA that targets nucleotides −65 to −47 relative to nucleotide 117 of SEQ ID NO:33.

15. The composition of claim 11, wherein said polynucleotide is an interfering RNA that targets AACCTGG-GATGGGCACCCCTG (SEQ ID NO:25).

16. The composition of claim 11, wherein said polynucleotide is an interfering RNA comprising AAC CCG GGA UGC GCG CCG AAA (SEQ ID NO:22).

17. The composition of claim 11, wherein said polynucleotide is an interfering RNA comprising CCC GGG AUG CGC GCC GAA AUU (SEQ ID NO:1).

18. The polynucleotide of claim 11, wherein said extended 5'-UTR AS mRNA mammalian mRNA.

19. The composition of claim 11, wherein said polynucleotide increases endothelial AS production, and increases endothelial nitric oxide production.

20. A method of increasing expression of endothelial argininosuccinate synthase (AS) in mammalian endothelial cells, comprising administering an effective amount of the polynucleotide of claim 1 to the cells to increase AS expression.

21. The method of claim 20, wherein said administering is carried out in vivo.

22. The method of claim 21, wherein the mammal is human.

23. The method of claim 20, wherein the polynucleotide increases endothelial nitric oxide production.

* * * * *

UNITED STATES PATENT AND TRADEMARK OFFICE
CERTIFICATE OF CORRECTION

PATENT NO. : 7,718,625 B2
APPLICATION NO. : 11/341177
DATED : May 18, 2010
INVENTOR(S) : Duane C. Eichler, Larry P. Solomonson and Laura C. Pendleton It is certified that error appears in the above-identified patent and that said Letters Patent is hereby corrected as shown below:

Column 3,
Line 13, "Zarnore et al.," should read --Zamore *el al.,*--.

Column 8,
Line 66, "3.0-Hi" should read --3.0-H1--.
Lines 66-67, "(SEQ ID NOs:30-3 1)." should read --(SEQ ID NOs:30-31).--.

Column 27,
Line 62, "(Brumnmelkamp et al.," should read --(Brummelkamp *et al.,*--.

Column 33,
Line 52, "Chemilmager" should read --ChemiImager--.

Column 43,
Lines 31-32, "391(6669):8061 1;" should read --391(6669):80611;--.

Column 45,
Line 60, "Brumnmelkamp" should read --Brummelkamp--.

Column 63,
Line 56, "mRNA mammalian mRNA." should read --mRNA is mammalian mRNA.--.
Line 58, "mRNA mammalian mRNA." should read --mRNA is human mRNA.--.

Column 64,
Line 31, "The polynucleotide of" should read --The composition of--.
Line 32, "mRNA mammalian mRNA." should read --mRNA is mammalian mRNA.--.
Line 45, "The polynucleotide of" should read --The composition of--.
Line 46, "mRNA mammalian mRNA." should read --mRNA is human mRNA.--.

Signed and Sealed this

Nineteenth Day of October, 2010

David J. Kappos
*Director of the United States Patent and Trademark Office*